(12) United States Patent
Prewer

(10) Patent No.: US 9,290,862 B2
(45) Date of Patent: Mar. 22, 2016

(54) DUAL MOBILE PHASE APPARATUS AND METHOD

(75) Inventor: Andrew Richard Russell Prewer, Rockland-St-Mary (GB)

(73) Assignee: Swedish Biomimetics 3000 Limited, Epsom, Surrey (GB)

( * ) Notice: Subject to any disclaimer, the term of this patent is extended or adjusted under 35 U.S.C. 154(b) by 1053 days.

(21) Appl. No.: 12/683,272

(22) Filed: Jan. 6, 2010

(65) Prior Publication Data

US 2010/0120636 A1  May 13, 2010

Related U.S. Application Data

(63) Continuation-in-part of application No. 12/667,519, filed as application No. PCT/GB2008/002288 on Jul. 3, 2008.

(60) Provisional application No. 61/143,092, filed on Jan. 7, 2009.

(30) Foreign Application Priority Data

Jul. 3, 2007 (GB) .................................. 0712922.4

(51) Int. Cl.
  *C07K 1/04* (2006.01)
  *C40B 60/14* (2006.01)
  (Continued)

(52) U.S. Cl.
  CPC ............. *C40B 60/14* (2013.01); *B01J 19/0046* (2013.01); *B82Y 30/00* (2013.01); *B01J 2219/0059* (2013.01); *B01J 2219/00274* (2013.01);
  (Continued)

(58) Field of Classification Search
  CPC .......... C07K 1/042; C07K 1/045; C07K 1/047
  USPC ................................................ 436/44; 422/66
  See application file for complete search history.

(56) References Cited

U.S. PATENT DOCUMENTS 4,272,506 A    6/1981  Schwarzberg
4,915,812 A *  4/1990  Parce et al. ................. 204/403.1
(Continued)

FOREIGN PATENT DOCUMENTS

CN    1079786 A    12/1993
CN    1578865 A     2/2005
(Continued)

*Primary Examiner* — Jan Ludlow
(74) *Attorney, Agent, or Firm* — Morgan, Lewis & Bockius LLP

(57) ABSTRACT

An apparatus and system for contacting a mobile elongate solid phase, e.g. a ribbon with a flowing fluid phase, and a method for using the same in, for example solid phase synthesis. A particular apparatus comprises (i) a conduit which is of circular or non-circular transverse cross section and which defines a lumen to contain both the flowing fluid phase and the mobile elongate solid phase; (ii) fluid phase ports in communication with the lumen to allow the fluid phase to enter the lumen, flow through it and exit it; and (iii) solid phase ports in communication with the lumen to allow the mobile solid phase to enter the lumen, move through it and exit it, the apparatus being adapted to prevent fluid egress from its interior through the solid phase ports.

Also provided is a continuous process for synthesizing and screening molecules, comprising passing an elongate solid phase through successive treatment stations where different stages of a solid phase synthesis are performed, and screening the synthesized molecules for activity.

29 Claims, 19 Drawing Sheets

(51) Int. Cl.
*B01J 19/00* (2006.01)
*B82Y 30/00* (2011.01)

(52) U.S. Cl.
CPC ............ *B01J2219/00331* (2013.01); *B01J 2219/00454* (2013.01); *B01J 2219/00497* (2013.01); *B01J 2219/00515* (2013.01); *B01J 2219/00518* (2013.01); *B01J 2219/00527* (2013.01); *B01J 2219/00596* (2013.01); *B01J 2219/00605* (2013.01); *B01J 2219/00655* (2013.01); *B01J 2219/00675* (2013.01); *B01J 2219/00686* (2013.01); *B01J 2219/00725* (2013.01); *B01J 2219/00871* (2013.01); *C07K 1/042* (2013.01); *C07K 1/045* (2013.01); *C07K 1/047* (2013.01)

(56) References Cited

U.S. PATENT DOCUMENTS

| 5,420,047 A * | 5/1995 | Brandt et al. ............... 435/7.9 |
| 5,429,925 A | 7/1995 | Vanderlaan et al. |
| 6,319,722 B1 | 11/2001 | Litwin et al. |
| 7,273,589 B2 | 9/2007 | Stimpson et al. |
| 7,300,798 B2 | 11/2007 | Perbost et al. |
| 2002/0001544 A1 | 1/2002 | Hess |
| 2003/0119193 A1* | 6/2003 | Hess et al. ............... 436/44 |
| 2007/0090104 A1 | 4/2007 | Collins et al. |

FOREIGN PATENT DOCUMENTS

| DE | 102004008319 A1 | 8/2005 |
| DE | 10-2004-008319 A1 | 9/2005 |
| EP | 0385433 A | 5/1990 |
| EP | 0 385 433 A2 | 9/1990 |
| EP | 0 569 940 B1 | 11/1993 |
| EP | 1 304 162 A2 | 4/2003 |
| EP | 1304162 A | 4/2003 |
| GB | 2274843 A | 8/1994 |
| JP | 354051883 A | 4/1979 |
| JP | 357063866 A | 10/1982 |
| JP | 2003066021 A | 3/2003 |
| WO | WO 02/13961 | 2/2002 |
| WO | WO 02/13961 A2 | 2/2002 |
| WO | WO 03/38183 A1 | 5/2003 |
| WO | WO 2009/004344 | 1/2009 |

* cited by examiner

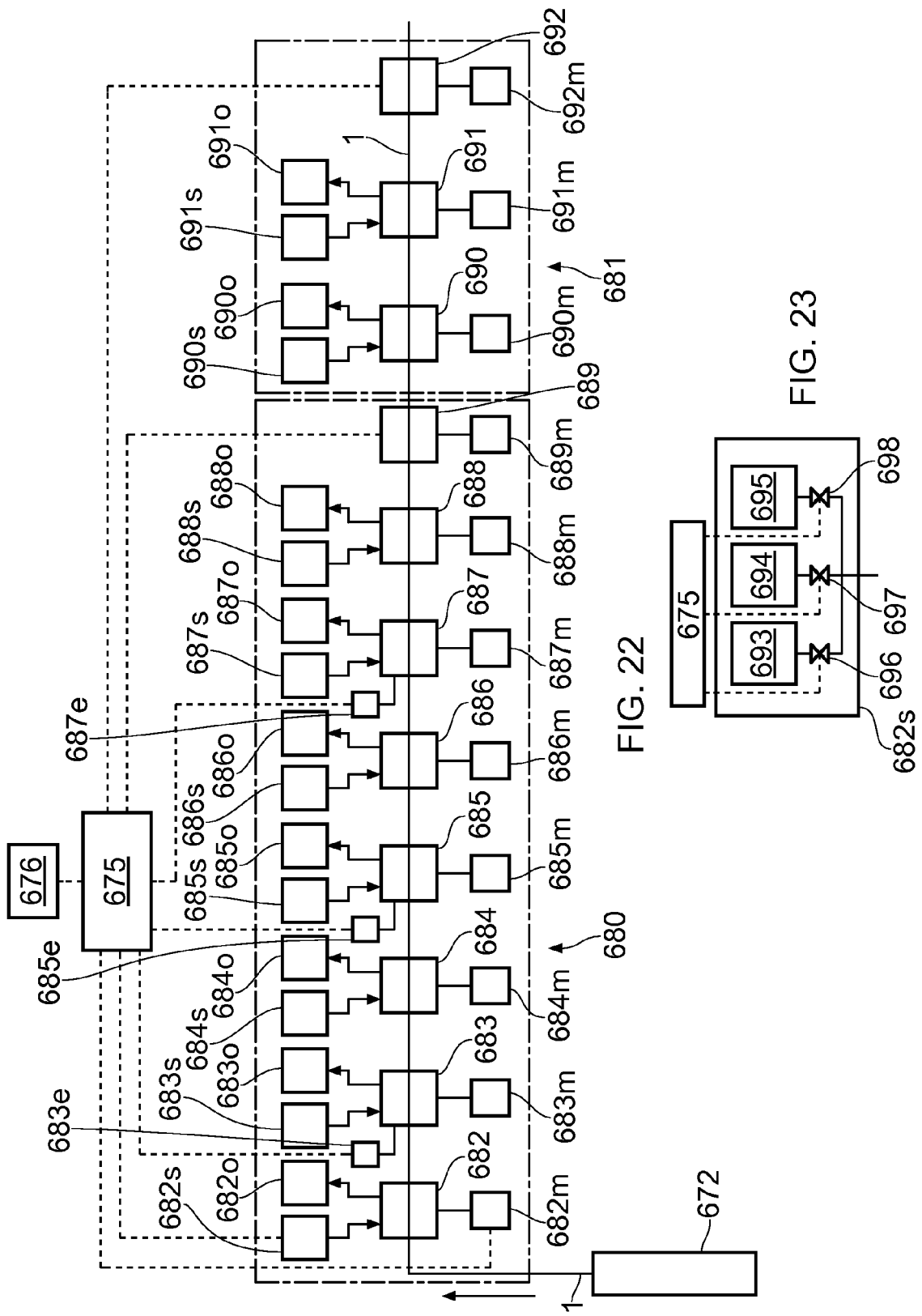

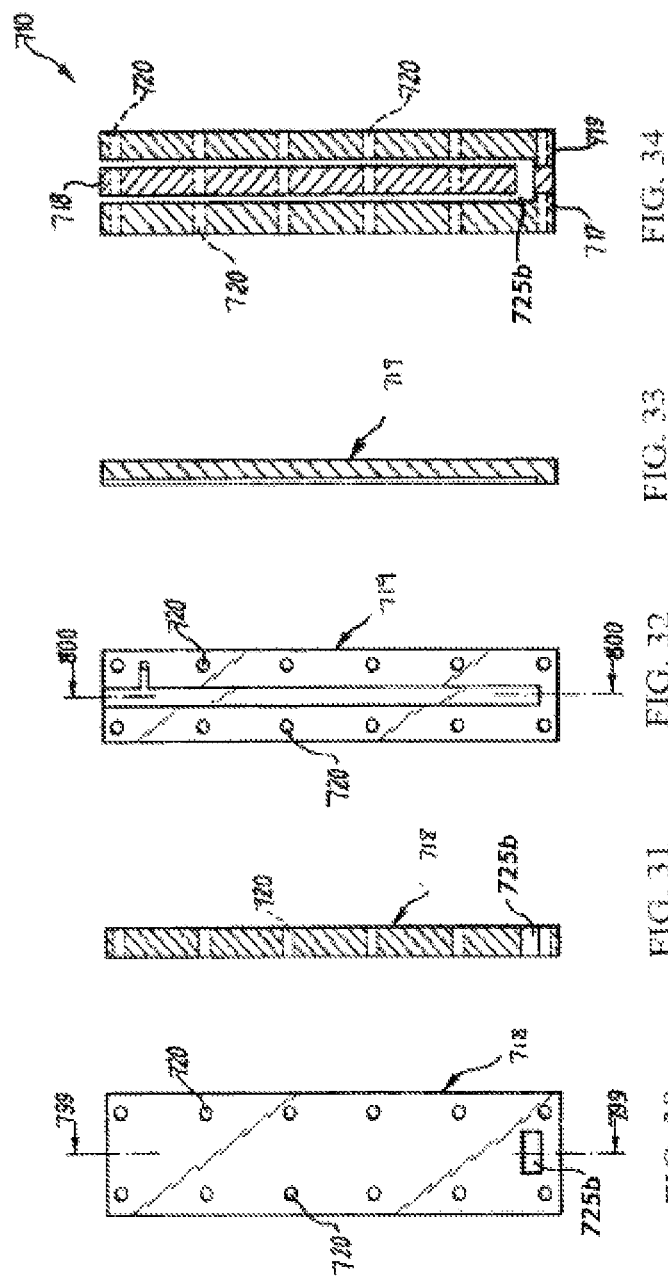

DUAL MOBILE PHASE APPARATUS AND METHOD

This application is a Continuation-in-Part of U.S. application Ser. No. 12/667,519, which is a U.S. National Phase of PCT/GB2008/002288 filed Jul. 3, 2008, which claims priority to GB Application No. 0712922.4 filed Jul. 3, 2007, which applications are incorporated herein by reference in their entirety for all purposes. This application also claims priority under 35 U.S.C. §119(e) to U.S. Provisional Patent Application No. 61/143,092 filed Jan. 7, 2009 which is incorporated herein by reference in its entirety for all purposes.

The present invention relates to methods which involve a mobile solid phase and a mobile fluid phase. It also relates to apparatuses and systems for performing treatments involving a mobile solid phase and mobile fluid phase, and to processes, apparatuses and systems for synthesising, screening and/or assaying molecules as well as to other subject matter. Amongst other things, the invention is concerned in some embodiments with solid phase synthesis, for example the synthesis of arrays of biological or other polymers on cellulose and other solid phase materials.

BACKGROUND

There will first be described prior art describing the chemistry of solid phase synthesis.

A useful review of the preparation of cellulose-bound peptide arrays is Hilpert K et al, Cellulose-bound peptide arrays: Preparation and applications, *Biotechnol. Genet. Engineer. Rev.* 2007, 24:31-106. Hilpert et al teach that cellulose is a polysaccharide with free hydroxy groups and that, since these hydroxy groups are less reactive than amino groups, the direct attachment of amino acids often leads to low yields. To make the cellulose suitable for the synthesis of peptides, the cellulose surface is modified to change the functionalisation from hydroxy to amino groups. It is further taught that modification of the cellulose often involves insertion of a spacer molecule permitting better access to the amino groups on the cellulose. After functionalisation, the amino acids are taught to be coupled either as an active ester (e.g. pentafluorophenyl ester) solution or as in situ activated mixtures. In situ activation is described as mostly carried out with DIC (N,N'-diisopropyl carbodiimide) and HOBt (N-hydroxybenzotriazole) shortly before coupling. Pages 34-42 of Hilpert et al are referred to here in particular as describing pre-treatment of the cellulose and peptide synthesis. Techniques for screening peptide arrays are described later in the same paper. Hilpert et al mention also non-cellulosic substrates (on page 33) and the synthesis of non-peptidic compounds (on page 43).

Mutulis F et al, *J. Comb. Chem.* 2003, 5:1-7 describe a method for producing non-random peptide libraries using cotton discs. The discs were activated in (25 v/v % in DCM) TFA (to protonate the hydroxy groups of the cotton). To enable peptide synthesis a handle was attached to the cotton to provide access to reagent molecule and a linker was then attached to the handle to provide a reactive site for Fmoc solid phase synthesis. The handle was 6-aminocaproic acid ($H_2N$—$(CH_2)_5$—COOH) and the linker was Fmoc Rink linker 4-[(2,4-dimethoxyphenyl)(Fmoc-amino)methyl]-phenoxyacetic acid. Peptides having different amino acid sequences were then synthesised on different discs.

The synthesis of oligonucleotide arrays on cellulose is described by Frank W et al, *Nucl. Acids. Res.* 1983, 11:4365-4377. Paper discs were pretreated by coupling protected nucleoside-3'-succinates were coupled to the discs by condensation of their carboxylic functions with the hydroxy groups of the cellulose in the presence of MSNT (1-(mesitylene-sulfonyl)-3-nitro-1,2,4,-triazole). After deprotection, a dimethoxy-tritylated base protected phosphodiester is coupled to the pretreated paper disc and further dimethoxy-tritylated base protected phosphodiester building blocks are linked step by step to form the completed oligonucleotide.

Fromont C et al, *Chem. Commun.* 2000, 283-284 describes the use of triple branching symmetrical dendrimers to increase the loading of a solid phase in the form of resin beads. The authors describe the synthesis of a tri-branching symmetrical dendrimer on the solid phase with an 18-fold amplification of loading. The tri-functional dendrimer monomers were prepared in bulk by alkylation of tris with acrylonitrile followed by nitrile hydrolysis in a saturated solution of HCl in dry MeOH to give the methyl ester. The hindered amino group of the methyl ester was converted to the corresponding isocyanate by treatment with $Boc_2O$ and DMAP as described by Knölker to give a stable symmetrical monomer (Knölker H-J et al, *Angew. Chem., Int. Head. Engl.* 1995, 34: 2497) an amino methyl polystyrene resin was directly derivatised with the isocyanate. The methyl ester was displaced by propane-1,3-diamine. The process was repeated to give Generation 2.0 dendrimer beads. The use of glass as a substrate for attachment of analytes or biological molecules is well known. For example, Millipore Data Sheet "DNA Nucleoside Controlled Pore Glass (CPG®) media" describes the use of DNA-CPG products for the solid phase synthesis of oligonucleotides using phosphoramidite chemistry. The data sheet is identified as Lit. No. DS0010EN00 Rev. A 03/06.

Shenoy N R et al, *Protein Sci.* 1992, 1: 58-67 describes the use of carboxylic acid-modified polyethylene as a solid phase support for polypeptides. The peptides are attached by coupling the N-terminal amino group of the peptides to the activated carboxyl groups of the film. The carboxylic acid-modified polyethylene (PE-COOH film) was provided by the Pall Corporation of Long Island, N.Y. The highest yields of covalently attached peptide were obtained when 1,3-dicyclohexylcabrodiimide (DCC) was used as an activating agent.

It is also known to use so-called "CLEAR" resins (Cross-Linked Ethoxylate Acrylic Resin) as supports for solid phase peptide synthesis. Such CLEAR products are described in U.S. Pat. Nos. 5,910,554 and 5,656,707 and are produced by Peptides International, Inc.

Sanghvi Y S et al, *Pure and Applied Chemistry*, 2001, 73: 175-180 describe reusable solid support chemistries for oligonucleotide synthesis. The reusable solid support technology is based on the use of a hydroquinone diacetic acid spacer arm between the 3'-end of the first nucleoside and the hydroxyl-functionalised support. Details of the chemistry have been published in Pon R T et al, *Nucleic Acids Research*, 1999, 27: 15-31.

For a review article relating to developments in solid phase synthesis supports see Sucholeiki, *Molecular Diversity*, 1999, 4: 25-30. The new solid phase synthesis supports described include cross-linked polyoxyethylene-polystyrene and polyoxyethylene-polyoxypropylene and polyamidoamine dendrimers attached to TentaGel support.

The solid phase PEGylation of a protein has been described by Lee B K et al in *Bioconjugate Chem.*, 2007, 18: 1728-1734. Recombinant interferon α-2a was absorbed to a cation exchange resin and PEGylated at the N-terminus by mPEG aldehydes through reductive alkylation using $NaBH_3CN$ as reducing agent.

An increasingly important class of polymer is organic semiconductor polymers. Turner D et al, *Mat. Res. Soc. Symp. Proc.*, 2003, 771: L8.8.1-L8.8.5 describes a solid phase synthetic strategy for the production of organic semiconductors.

The strategy uses a germanium-based linker and Suzuki-type cross-coupling protocols and has been demonstrated for the iterative synthesis of both a regio-regular oligo-3-alkylthiophene and an oligoarylamine. Turner et al is included herein in its entirety for all purposes, as are references 1, 2, 3 and 4 of Turner et al.

For further information on solid phase synthesis techniques, reagents and substrates see *Organic Synthesis on Solid Phase: Supports, Linkers, Reactions*, Florencio Zaragoza Dörwald, Wiley-VCH, Second Edition, 2002, ISBN 352730603X.

There will be described next prior art relating to methods performed using a mobile solid phase.

EP 0385433A2 discloses a method and apparatus for continuous synthesis on a solid carrier. The solid carrier, for example in the form of a band or thread, has functional groups and is passed through successive reaction and processing zones in a sequence corresponding to the reaction and processing steps of the synthesis concerned. The reaction and processing zones are in the form of baths of liquid, and the carrier coming from the preceding synthetic step is pressed between a pair of rollers to remove most of the liquid from the preceding step.

EP 1304162A2 discloses a method and apparatus for the preparation of polymer arrays on the surface of a flexible elongate web. The apparatus includes a dispensing head and optionally other treatment stations including reagent baths and water baths, the latter being for rinsing. A detection station may be included for detecting fluorescence. The web is driven through these various stages of the apparatus for successive treatments to be carried out at successive stages.

US 2002/0001544A1 discloses a system and method for high throughput processing of droplets. The droplets are dispensed onto a moving surface from one or more reagent addition stations through which the moving surface moves. A combinatorial synthesis may be accomplished and assays can be performed directly on the chemical reaction products on the moving surface.

All the above prior art documents are included herein by reference in their entirety for all purposes.

BRIEF SUMMARY OF THE DISCLOSURE

This specification contains disclosures of apparatuses, systems and methods for use in processing a mobile elongate solid phase.

In one aspect, there is provided an apparatus for contacting a mobile elongate solid phase with a flowing fluid phase, comprising: a conduit which is of circular or non-circular transverse cross section and which defines a lumen to contain both the flowing fluid phase and the mobile elongate solid phase; fluid phase ports in communication with the lumen to allow the fluid phase to enter the lumen, flow through it and exit it; and solid phase ports in communication with the lumen to allow the mobile solid phase to enter the lumen, move through it and exit it. The apparatus may be adapted to prevent fluid egress from its interior through the solid phase ports.

In one embodiment, the conduit comprises a region in which the conduit undergoes a change in direction. In another embodiment, the conduit does not undergo a change in direction.

The fluid may be a liquid. The fluid may be a flowable foam or a flowable gel. Alternatively, the fluid may be a gas.

The conduit may be configured to accommodate a solid phase in the form of a ribbon having a width of at least 10 mm, e.g. of about ¾ inch (about 19 mm) or more, optionally about 22 mm or more and often of no more than about 30 cm, e.g. no more than about 20 cm. In embodiments, the conduit is configured to accommodate a ribbon having a width of no more than about 10 cm, e.g. no more than about 5 cm. The conduit may provide a small clearance (e.g. from about 1 mm to about 5 mm, especially from about 2 mm to about 4 mm) beyond the width of a ribbon as just mentioned. The conduit may therefore have a longest cross sectional dimension which is at least about 10 mm, for example at least about 11 mm, and optionally of about 20 mm or more, as in the case of about 22 mm or more. In embodiments, the conduit may have a longest cross sectional dimension of no more than about 30 cm, e.g. no more than about 20 cm or more and optionally of no more than about 10 cm, as in the case of no more than about 5 cm, for example. In particular embodiments, the conduit has a longest cross sectional dimension which is from about 20 mm to about 25 mm, e.g. which is about 20 mm, about 21 mm, about 22 mm, about 23 mm, about 24 mm or about 25 mm.

In embodiments, the conduit is generally rectangular in cross section and has a height (shortest cross sectional dimension) of between about 1 mm and about 5 mm, and optionally at least about 1.2 mm, for example at least about 1.4 mm. The height may be no more than about 4 mm, e.g. no more than about 3 mm; often the height is no more than about 2.5 mm, e.g. no more than about 2.3 mm. In embodiments, the height is no more than about 1.8 mm. The height may therefore be from about 1.2 mm to about 2.5 mm, e.g. from 1.2 mm to 2.3 mm, optionally of about 1.5 mm or about 2 mm or intermediate those two values.

Included are embodiments in which the length of the lumen in which the solid and fluid phases are in contact is from about 25 cm to about 500 cm, e.g. about 25 cm to about 300 cm, about 50 cm to about 500 cm, about 50 cm to about 300 cm, for example about 50 cm to about 200 cm, such as about 70 cm to about 150 cm, for example.

In some embodiments, the apparatus includes a structure defining the conduit which structure comprises a first plate having a face on which an open channel is defined and, in engagement with the first plate, a second plate closing the perimeter of the channel. The first and second plates may be releasably held in engagement. In embodiments, the plates engage indirectly through a sealing material, for example a solid gasket or a "liquid gasket", i.e. a grease or paste. In embodiments, at least one of the first and second plates has provided thereon or therein a sensor arranged to determine a parameter of a fluid phase contained in the channel, an energy source arranged to expose the channel to energy, or both The lumen may contain an elongate solid phase. The elongate solid phase may comprise a species selected from a polymer and one or more synthetic building blocks for a polymer attached to a substrate; the polymer may be a biological polymer or a non-biological polymer. In embodiments the polymer is not a poly(amino acid). The solid phase may comprise a small organic molecule attached to a substrate.

Included in the disclosure are embodiments in which the apparatus is not as described in PCT/GB2008/002288, in particular in which the apparatus does not comprise a sealing material between plates. Another embodiment in which the apparatus is not as described in PCT/GB2008/002288 is one in which the apparatus does not comprise three cuboidal blocks engaging one another in face-to-face arrangement such that two of the blocks occupy end positions and the third block occupies a central position, each end block having defined in its face engaging the central block a channel which communicates with the channel in the other end block via a through aperture in the central block. Accordingly, there is disclosed apparatus which includes a conduit-defining structure which comprises a first plate having a face on which an open channel is defined and, in engagement with the first plate, a second plate closing the perimeter of the channel, but wherein the apparatus is not as described in PCT/GB2008/002288.

Further included in the invention is an apparatus for performing a process involving a mobile elongate solid phase and defining (i) a conduit to contain the solid phase and optionally to contain also a flowing fluid phase in contact with the solid phase, and (ii) solid phase ports in communication with the interior of the conduit to allow the mobile solid phase to enter the conduit, move through it and exit it, the apparatus comprising three plates, each comprising two opposed faces, the plates being releasably interconnected in face-to-face relationship such that there is an intermediate plate between first and second end plates, the interconnected plates forming a unit having a first end and a second end, the intermediate plate having an aperture defined therein towards the second end of the unit to define a channel between its two faces, the aperture optionally having a roller rotatably arranged therein, and wherein:

the first end plate and the intermediate plate define therebetween a first arm of the conduit;

the second end plate and the intermediate plate define therebetween a second arm of the conduit;

the first and second arms extend in a direction from the first end of the unit to the second end of the unit and each terminate at, and in fluid connection with, the aperture; and at least one of the plates comprises: a sensor arranged to determine a parameter of the solid phase; a sensor arranged to determine a parameter of the fluid phase; an energy source to expose the interior of the conduit to energy; and a deposition device for depositing a substance onto the solid phase.

The unit may have fluid phase ports in communication with the interior of the conduit to allow the fluid phase to enter the conduit, flow through it and exit it. The first and second arms may each have a region towards the first end of the unit which region is in communication with the solid phase ports and the fluid phase ports, the solid phase port of each arm being spaced further towards the first end of the unit than the fluid phase port of the arm.

A process of the invention for treating a mobile elongate solid phase with a flowing fluid phase comprises moving the solid phase and the fluid phase through a lumen of a conduit in which lumen the two phases come into mutual contact. In embodiments, the solid and liquid phases are moved through an apparatus as described herein for contacting a mobile elongate solid phase with a flowing fluid phase; more particularly, such a process may comprise moving the solid phase through a first solid phase port of the apparatus into the lumen of the apparatus, though the lumen and out through a second solid phase port of the apparatus; causing a fluid phase to enter the lumen of the apparatus through a first fluid phase port, flow through the lumen and leave through a second fluid phase port.

A further aspect of the invention resides in system for subjecting a longitudinally mobile elongate solid phase to a plurality of successive treatments, comprising a plurality of phase contact devices for contacting the mobile elongate solid phase with a flowing fluid phase, each phase contact device comprising (i) a conduit which is circular or non-circular in transverse cross-section and defines a lumen to contain both the flowing fluid phase and the mobile elongate solid phase, (ii) fluid phase ports in communication with the lumen to allow the fluid phase to enter the lumen, flow through it and exit it, and (iii) solid phase ports in communication with the lumen to allow the mobile solid phase to enter the lumen, move through it and exit it, the phase contact device being adapted to prevent fluid egress from its interior through the solid phase ports, wherein: the system is arranged for a solid phase pathway to be defined between successive phase contact devices such that the solid phase may move through the successive phase contact devices one after another; a first phase contact device and a second phase contact device are disposed in succession along the pathway and are arranged to receive fluid from a common first fluid source; and a third phase contact device along the pathway is arranged to receive fluid from a second fluid source.

Additionally included in the invention is a system for carrying out a heterogeneous process, comprising: a treatment apparatus configured to contain a flowing fluid phase and a longitudinally moving elongate solid phase in mutual contact; a controllable drive device for moving the solid phase through the treatment apparatus; a controllable fluid metering device for providing a controlled fluid phase flow to the treatment apparatus; a sensor arranged to detect a parameter of the solid phase after the solid phase has passed through the treatment apparatus; a processor adapted to be in signal communication with the sensor and with at least one of the drive device and the fluid metering device to receive an input signal from the sensor and send an output signal to the at least one of the drive devices and the fluid metering device, the processor being programmed to control the at least one of the drive device and the fluid metering device responsive to the detected parameter.

Another embodiment of the invention resides in a modular system for carrying out a heterogeneous process, comprising: a plurality of treatment assemblies for contacting a longitudinally mobile elongate solid phase with a flowing fluid phase, the assemblies being provided in a modular arrangement and each assembly defining a lumen to contain the mobile solid phase and the flowing fluid phase in contact with each other, and each assembly being capable of being releasably connected on a first side to a portion of a second said assembly and on a second side to a portion of a third said assembly to form a treatment zone comprising three said assemblies in succession and defining a continuous pathway for an elongate solid phase to move through the treatment assemblies comprised in the treatment zone.

Also included in the invention is a process for synthesising and screening molecules, comprising: moving an elongate solid phase through sequential treatment stations, each for performing a respective stage of a solid phase synthesis, at least one of the treatment stations being adapted to spatially address synthetic building blocks onto the solid phase, whereby to form on the solid phase at the end of the synthesis an array of spatially distinct areas, each area occupied by end product molecules of a respective predetermined structure; moving the solid phase on which the array is formed through a treatment station where it is contacted with an agent which, when it contacts an analyte having a predetermined property, undergoes a process specific to such analyte to create a measurable response; measuring the amount of the measurable response of each spatially distinct area; and identifying an end product molecule structure resulting in a highest measurable response. In some optional embodiments, at least one other of the treatment stations comprises an apparatus of the present disclosure for contacting a mobile elongate solid phase with a flowing fluid phase; such an apparatus may be used for washing the elongate solid phase or to contact the solid phase with a chemical or biological agent.

Further provided by the invention is an apparatus for use in synthesising and screening molecules, the apparatus providing a pathway for an elongate solid phase to move along and comprising disposed along the pathway in a direction from upstream to downstream: sequential treatment stations, each for performing a respective stage of a solid phase synthesis, at least one of the treatment stations comprising plural deposition devices for spatially addressed deposition of synthetic building blocks onto the solid phase; a treatment station for contacting the solid phase with an agent which, when it contacts an analyte having a predetermined property, undergoes a process specific to such analyte to create a measurable response; and a measuring station for measuring the amount of the measurable response of each spatially distinct area, the apparatus further comprising a computer which is adapted to be in signal communication with, or which is in signal communication with, the measuring station and programmed to identify the highest measurable response and to determine the corresponding end product molecule structure from data available to the computer.

The invention also includes an apparatus for use in synthesising and screening molecules, the apparatus providing a pathway for an elongate solid phase to move along, the apparatus comprising disposed along the pathway in a downstream direction: sequential treatment stations, each for performing a respective stage of a solid phase synthesis, at least one of the treatment stations comprising plural deposition devices for spatially addressed deposition of synthetic building blocks onto the solid phase and at least one of the treatment stations comprising an apparatus of the present disclosure for contacting a mobile elongate solid phase with a flowing fluid phase; a treatment station for contacting the solid phase with an agent which, when it contacts an analyte having a predetermined property, undergoes a process specific to such analyte to create a measurable response; and a measuring station for measuring the amount of the measurable response of each spatially distinct area.

Also to be mentioned as falling within the invention is a method of treating a moving elongate solid phase with a flowing fluid phase, comprising causing the fluid phase to flow in a countercurrent direction to, and in contact with, the solid phase. The two phases may be maintained in contact in a conduit having a closed perimeter. The method may be a method of washing the solid phase with a liquid phase, or a method of causing or allowing a chemical or biological agent comprised in the fluid phase to bind to the solid phase or react with the solid phase, or both.

The fluid may be a gas or liquid and is more often a liquid than a gas.

Aspects and embodiments of the invention are disclosed in the following description and claims.

BRIEF DESCRIPTION OF THE DRAWINGS

Embodiments of the invention are further described hereinafter with reference to the accompanying drawings, in which:

FIG. 22 is a schematic plan of a system of the invention comprising multiple treatment zones; and FIG. 23 is a schematic plan of a fluid source featured in FIG. 22;

FIG. 30 is a front elevational view of the central glass block of the reactor shown in FIGS. 28 and 29;

FIG. 31 is a cross-sectional view of the central glass block taken along the line 99 of FIG. 30;

FIG. 32 is a front elevational view of the rear glass block of the reactor shown in FIGS. 28 and 29;

FIG. 33 is a cross-sectional view of the rear glass block taken along the line 100 of FIG. 32; and FIG. 34 is a cross-sectional view of the glass reactor taken along the line 101 of FIG. 29 but of the reactor in assembled form.

DETAILED DESCRIPTION

Figure 1:
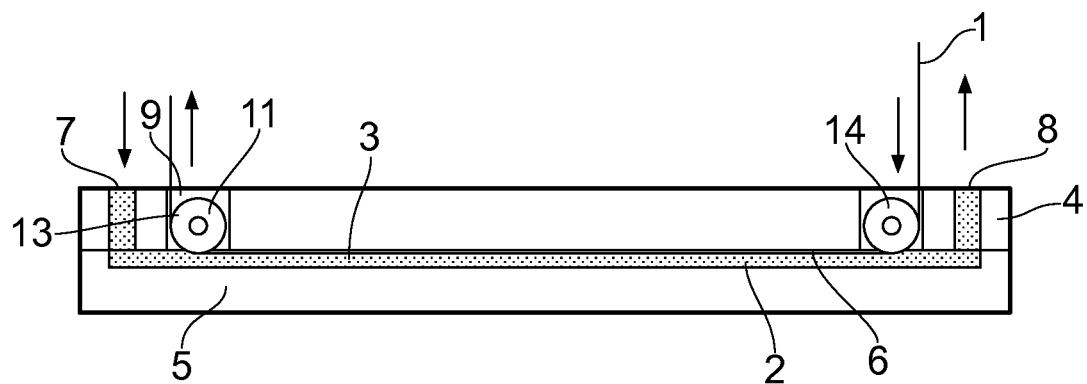
FIG. 1 is a longitudinal cross section through an apparatus according to a first embodiment of the invention.
Figure 2:
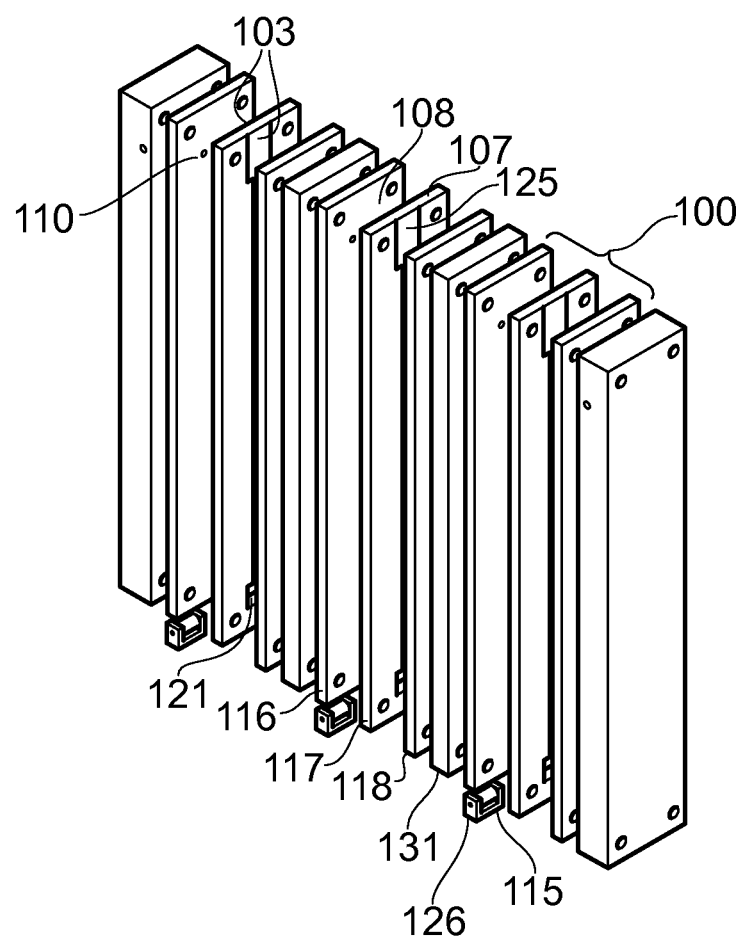
FIG. 2 is an exploded perspective view of plates and roller bearings forming a combination of apparatuses according to a second embodiment of the invention.
Figure 3:
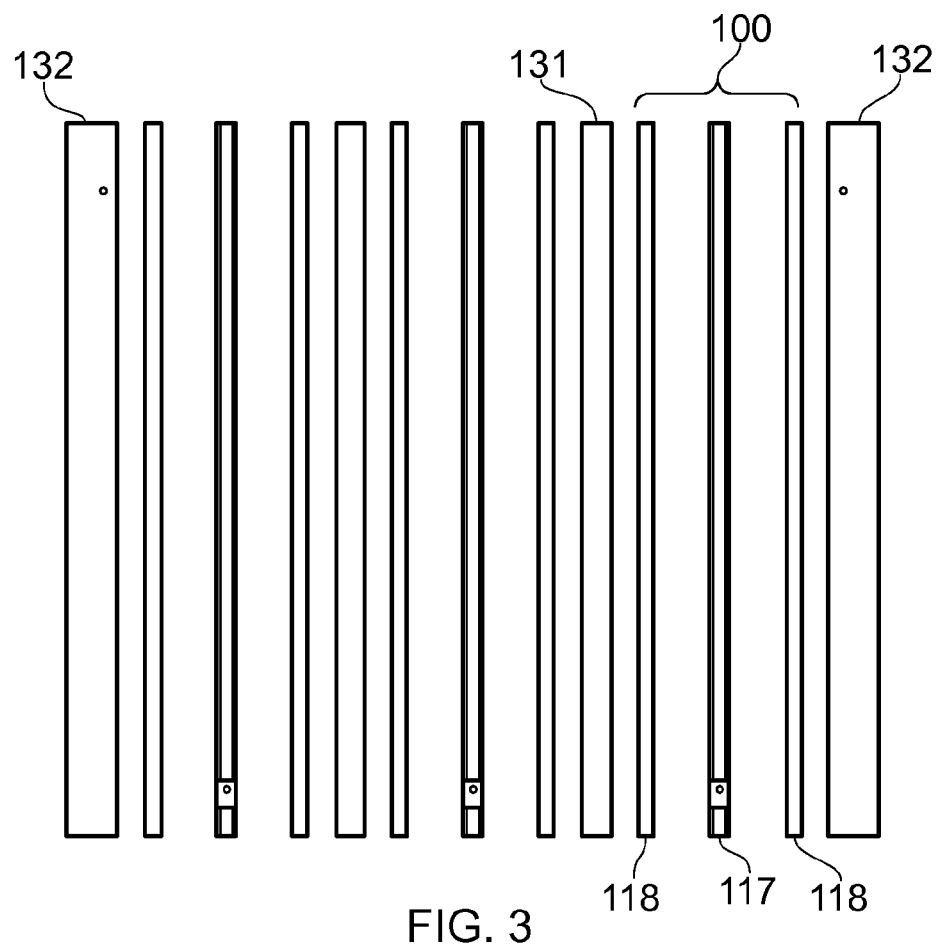
FIG. 3 is a side view of the plates and roller bearings of FIG. 2.

Throughout the description and claims of this specification, the words "comprise" and "contain" and variations of them mean "including but not limited to", and they are not intended to (and do not) exclude other moieties, additives, components, integers or steps.

Throughout the description and claims of this specification, the singular encompasses the plural unless the context otherwise requires. In particular, where the indefinite article is used, the specification (which term encompasses both the description and the claims) is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

Included in the invention are apparatuses and methods for use in solid phase synthesis. Solid phase chemistry will require no elucidation for the skilled reader but, nonetheless, the reader is directed to the publications mentioned under the heading "Background" for further information on materials and methods which may be used in solid phase synthesis.

As used herein the term "plate" is used to refer a member which defines a face or faces as the context of the term requires. The term "plate" does not imply that the member is thin, i.e. has one dimension markedly less than its other two dimensions; thus, for example, no distinction can be made between the terms "plate" and "block", since in this specification both terms have the same meaning. Nonetheless, to save material costs a plate may be thin but this is not a mandatory technical requirement and thinness is not a feature of the invention, despite being a feature of plates of some embodiments of the invention. A typical plate is generally cuboidal in shape but this is not a mandatory technical requirement and a cuboidal shape is not a feature of the plates used in the invention, despite being a feature of plates of some embodiments of the invention.

The present invention relates to processes involving a mobile solid phase, as well as to systems and apparatuses for use in such methods. Sub-parts of such methods, apparatuses and systems are also included in the scope of the invention.

The invention generally relates to any process which involves contacting a mobile solid phase with a mobile fluid phase. During the process, therefore, the solid phase moves or is able to move; for example the movement of the solid phase may be a movement which would for practical purposes be considered continuous (including continuous movement driven by a stepper motor, which in fact rotates in high frequency steps). In some embodiments, the solid phase is stationary during performance of a process and then moved on to another apparatus to be subjected to another process. In other embodiments, the solid phase moves intermittently during performance of a stage of a process. The fluid phase flows during at least part of a process of the disclosure and it may flow continuously. Thus, the invention includes embodiments in which the solid phase is contacted with, e.g. surrounded by, a stream of fluid during part or all of a process. A fluid may flow continuously during a process but in some embodiments fluid flow is discontinuous. In many embodiments, both the solid phase and the fluid phase move continuously between the beginning and the end of a process.

As will become apparent, a fluid is typically a liquid but may be a gas. For the purpose of this disclosure, the term "liquid" includes liquid-like materials, for example foams or gels.

The solid phase is elongate in form, for example an elongate flexible web or a cord. It comprises a substrate, for example a natural or synthetic polymer, of which cotton and other cellulosic materials are an example. Alternative materials are described later in this specification as well as previously herein under the heading "Background". The process may serve to modify the substrate, for example activate it, functionalise it or change its functionality, in any of those cases typically to prepare the solid phase for attaching a substance to it. Thus, the solid phase may have a substance attached to it, often covalently but sometimes non-covalently. Non-covalent attachment may be adsorption; it may involve hydrogen bonding, ionic bonding or van der Waals forces, or a combination thereof. A substance may be a spacer or a linker, or a combination thereof, whose function is to enable or facilitate tethering, e.g. covalent bonding, of a second substance to the solid phase. A substance attached to a substrate may comprise a starting material or an intermediate in a synthetic process, for example a monomer, oligomer or intermediate polymer formed as an intermediate in the preparation of an end product polymer. An end product may therefore comprise a substance having repeating units; the smallest such substance is a dimer, e.g. a dipeptide; more often the number of repeating units is greater than two and an end product may be a polymer, e.g. a biological polymer or a non-biological polymer. A substance having repeating units may be a poly(amino acid). As biological polymers may be mentioned polypeptides, polynucleotides and polysaccharides. As non-biological polymers may be mentioned organic semiconductor polymers.

Particular polymers which may be made are organic semiconductor polymers, for example made following the procedure of Turner et al (see above). A suitable substrate is functionalized with hydroxy groups which are further functionalised to provide a reactive germyl linker (see Scheme 3 of Turner et al).

The application of the apparatus and methods of the disclosure to the synthesis of organic semiconductor molecules is included in the invention. The invention therefore includes an organic semiconductor polymer attached to an elongate solid phase. The solid phase may be as described herein.

Included amongst synthetic processes are those in which a substance attached to a substrate is subjected to a process comprising synthetic modification. For example, a biological or non-biological molecule, e.g. biological oligomer or biological polymer, may be modified by attaching one or more saccharides, e.g. to provide an amino acid, polypeptide or lipid with an attached group comprising one or a plurality of saccharides. A molecule, e.g. completed polymer, for example a completed PEG or polysaccharide, may be coupled directly or indirectly to a substance (e.g. a polypeptide) attached to a substrate; one example of indirect coupling is through a poly(amino acid) which includes a sequence cleavable by a protease. Such a cleavable poly(amino acid) may be used to couple a lipid, for example a fatty acid, to another molecule, e.g. a polypeptide.

A substance attached to a substrate may be a starting material or intermediate in a synthetic process for forming a molecule not comprising repeating units, e.g. a small organic molecule having a molecular weight of, for example, less than 1000, optionally less than 500.

Where a solid phase is an intermediate or starting material for a synthesis attached to it, the solid phase is subjected to a solid phase synthesis process. In other processes, a substance attached to a solid phase is not intended for synthetic use but for another process, for example performance of an assay. Typically, an assay involves exposing a substance to a further substance and monitoring for, and optionally measuring, an interaction between the two; for example, the interaction may be binding or it may comprise a reaction or other change of state, as in the case of an enzyme and a substrate. An assay may involve exposing a substance to two or more further substances, for example to a first biological structure, e.g. molecule, and a second biological molecule which is able to interact with the first biological structure; in this case, the assay may involve monitoring for, and optionally measuring, any inhibition in the interaction caused by the substance attached to the substrate. A substance attached to a substrate for use in an assay may be a biological structure, e.g. biological molecule, or a synthetic molecule intended for use in an assay involving a biological structure or a structure having, at least in a qualitative sense, an activity of a biological structure, as in the case of a molecule comprising a fragment of a protein which fragment has, at least qualitatively, a binding activity of the protein.

A process of the disclosure, or using an apparatus of the disclosure, may comprise synthesising a molecule and then subject it to an assay. Alternatively, a process may comprise a synthesis after which the synthesised molecule is cleaved from the substrate, or it may comprise assaying a pre-synthesised substance (whether synthesised chemically or in a biological cell or living organism) which is attached to the substrate. It is re-emphasised that the disclosure is not limited to processes which comprise a synthesis and/or an assay, since any process comprising treatment of a solid phase with a fluid phase is encompassed by the disclosure. It will be understood, of course, that the process typically requires the solid phase to be presented in flexible and elongate form.

FIG. 1, therefore, illustrates a process for treating a mobile elongate solid phase 1 with a flowing fluid phase 2, comprising moving the solid phase 1 and the fluid phase 2 through a lumen of a conduit 3 in which the two phases 1 and 2 come into mutual contact. Also illustrated by FIG. 1 is an apparatus for use in performing the just-mentioned method, comprising a conduit 3 which defines a lumen to contain both the flowing fluid phase 2 and the mobile elongate solid phase 1. The apparatus necessarily includes fluid phase ports 7, 8 in communication with the lumen to allow the fluid phase to enter the lumen, flow through it and exit it as well as solid phase ports in communication with the lumen to allow the mobile solid phase to enter the lumen, move through it and exit it. These ports will be further described later. In use, fluid phase ports are respectively in communication with a fluid source and a fluid outflow line; typically, the fluid phase ports of an apparatus of the invention are connected to tubing or piping, optionally connected to the port by a connector (not shown in FIG. 1) which is integral with or firmly coupled to the apparatus. Inlet tubing or piping may be coupled directly or indirectly to a fluid source or fluid reservoir whilst outlet tubing or piping may be coupled directly or indirectly to, for example, a drain or to processing equipment for reprocessing the fluid (e.g. removing unwanted species) for reuse. The shape of the conduit in transverse cross-section is not critical to the invention, and may therefore be circular or non-circular. Where the solid phase 1 is in the form of a ribbon, the conduit may have a relatively long dimension to accommodate the width of the ribbon perpendicular to a relatively short dimension, for example the conduit may be generally rectangular in cross-section. However, the disclosure includes embodiments in which the solid phase is in the form of a ribbon and the conduit has a circular or square cross-section. As has already been mentioned, the cross-sectional shape of the conduit is not critical to the invention and is not limited to the individual shapes just mentioned.

The process for treating the solid phase 1 with the liquid phase 2 is to contact the two phases together to perform a desired process. The present invention is not limited as to the nature of the process which is performed but, in many cases, the process will comprise: a stage of a solid phase synthesis; a stage of an assay; or, whether as part of a solid phase synthesis or of an assay or otherwise, washing of the solid phase.

The invention is not limited as to the identity of the solid phase 1 or the liquid phase 2. The identities of the two phases are at least in part determined by the process being performed. The elongate solid phase 1 typically comprises a flexible elongate web or ribbon. A ribbon-shape increases the surface area to volume ratio and is considered to be advantageous, but the invention also includes other solid phase formats, for example it may be a cord or thread.

The solid phase 1 comprises a substrate and may optionally comprise a substance bonded thereto. The substrate material may comprise a woven or non-woven web, or another fibrous material, for example a cord or thread comprising multiple fibers. Exceptionally, the solid phase may be a mono-filament. In more frequent embodiments, the substrate may comprise a polymer film, for example in the form of a ribbon.

Where the solid phase 1 is being used for solid phase synthesis, it is often convenient for the substrate to comprise cotton or another cellulosic material, since cellulose materials are porous, hydrophilic, flexible, stable in many organic solvents and has hydroxy groups which are useful functional groups through which substances may be attached to the cotton. As an alternative to cotton, another cellulosic material may be used, although ordinary paper materials are unlikely to have sufficient strength. The use of cotton ribbon, i.e. a representative cellulosic solid phase, is described in more detail later in the specification.

As an alternative to cellulosic materials, may be mentioned synthetic polymers, for example a polymer film or a fibrous web. Polymer films may comprise single layer films or multilayer films having a surface suitable for attachment of a substance to be treated. Exemplary synthetic polymers which may form the solid phase or a surface of the solid phase include carboxylic-modified polyethylene "CLEAR" resin as described in U.S. Pat. Nos. 5,910,554 and 5,656,707 and re-usable solid supports.

A further alternative substrate is a glass fiber web or ribbon.

The fluid phase may be a gas phase comprising a reactive gas, for example ozone. As an example of the use of ozone may be mentioned the cleavage of sulfone linkers triggered by ozonolysis, to release a product from a solid phase support, as taught by Chang Y-F et al, *Tetrahedron Letters,* 2008, 49: 543-547. More usually, the fluid phase is a liquid phase. The liquid may consist of an aqueous liquid or a non-aqueous liquid, or it may comprise a mixture of miscible liquids. The liquid may be a solvent. Alternatively, the liquid may be a solution, comprising one or more solutes in a solvent, for example water or an organic solvent, or a mixture of solvents. The liquid phase may comprise an emulsion or a dispersion. The liquid may contain at least one reagent for undergoing a chemical reaction with the solid phase, for example a stage of a solid phase synthesis, for example the addition of a protecting group, the removal of a protecting group, the activation of a functional group or the addition of a synthetic building block such as, for example, an amino acid, nucleotide, saccharide or other biological polymer-forming unit (often, but not always, a monomer). Where the process performed in the lumen defined by the conduit 3 is a washing process, the liquid phase typically consists of a solvent, for example a single solvent compound or a mixture of solvent compounds.

The conduit suitably has surfaces made of a material substantially inert to the fluid phase. For example, the surface defining lumen may be made of a material inert to the reagents used in solid phase peptide synthesis, solid phase nucleic acid synthesis or solid phase polysaccharide synthesis. Exemplary are glass, polytetrafluoroethylene (PTFE), a ceramic material, or an inert metal material, for example stainless steel, a titanium alloy or a nickel alloy. Inert metal alloys are commercially available under the registered trade mark Hastelloy. Glass and PTFE, for example, are inert to all chemical agents encountered in normal use. The surface defining the lumen may be formed of a combination of inert materials. More usually, a single inert material is used. The inert material or materials may form the entirety of the device defining the conduit or a coating on at least the surface which defines the lumen.

Reverting now to FIG. 1, it will be noted that the conduit 3 does not undergo a change in direction, since it is in the form of a straight conduit or channel; this is a feature of some embodiments of the invention.

The conduit 3 of FIG. 1 is formed in apparatus comprising opposed plates, namely a first plate 4 and a second plate 5 which are disposed in opposed face-to-face relationship, the opposed faces having defined between them a length of conduit extending in a direction parallel with the pair of plates. The plates 4 and 5 may be releasably interconnected, in order to facilitate the assembly of the apparatus for cleaning and its reassembly. At least one of the first and second plates 4 and 5 has in its face facing the other plate a channel 6 which is open in a direction facing the opposed plate, such that the channel may be closed, except for the necessary ports for entry and exit of the solid phase and the fluid phase, when the first and second plates 4 and 5 engage each other. In the illustrated embodiment, just one of the two plates has such a channel formed therein, namely the second plate 5 which is disposed to the bottom of the apparatus when the apparatus is in its operative orientation.

As previously mentioned, the apparatus shown in FIG. 1 includes fluid phase ports 7 and 8 in communication with the lumen 3 to allow the fluid phase to enter the lumen, flow through it and exit it. The apparatus also includes solid phase ports 9 and 10 in communication with the lumen 3 to allow the mobile solid phase to enter the lumen, move through it and exit it. The two phases should be substantially separated outside the lumen and, for that reason, the apparatus of FIG. 1 is operated with its fluid outlet port under suction. In other embodiments the apparatus may be adapted to prevent fluid egress from its interior from lumen 3 (in this particular case) through the solid phase ports 9 and 10. For example, the apparatus may be for use with a fluid phase in the form of a liquid and egress of the liquid phase through the solid phase ports 9 and 10 may be prevented by positioning the solid phase ports 9 and 10 spaced above the fluid phase ports 7 and 8, when considering the apparatus in use. In FIG. 1, the solid phase ports 9 and 10 are defined at the upper ends of respective port channels 11 and 12 which are formed in the first (upper) plate 4.

It will be appreciated that, in the apparatus of FIG. 1, the solid phase 1 must undergo a change of direction at the juncture between the two port channels 11, 12 and the conduit 3; guide rollers 13 and 14 area provided for the purpose of guiding the solid phase 1 through each change of direction. The two guide rollers may be freely rotatable. Typically, the solid phase 1 engages a drive roller which serves to move the solid phase and at least one of the guide rollers 13, 14 may be a drive roller. Any drive roller is suitably coupled to an electric motor or other drive apparatus (not shown).

It is advantageous for the interfacing faces of the plates 4 and 5 to be as flat as possible in order to reduce or prevent liquid leakage. Additionally or alternatively, a solid gasket or a so-called "liquid gasket" may be provided at the interface between plates. The liquid gasket may be a grease insoluble in the solvent to be used in the treatment device. In one example, a silicone grease is used as a liquid gasket, e.g. is smeared over the mating surfaces of the plates. A solid gasket may be a PTFE sheet. A dual containment system may be used which has two gaskets, e.g. two solid gaskets or a solid gasket and a liquid gasket. One class of embodiments of the invention comprises apparatuses for contacting a mobile solid phase with a flowing fluid phase which include a conduit defined by plates having faces which directly or indirectly engage each other; the features mentioned in this paragraph may be applied to any such apparatus of the disclosure.

The solid phase may move through the apparatus in either direction, as may the fluid phase. As shown by the arrows in FIG. 1, the fluid phase 2 may move in counter current to the solid phase 1, i.e., the two phases may move in opposite directions through the conduit 3. Alternatively, the two phases may move co-currently, i.e. in the same direction through the conduit 3, whether at the same or different speeds. The movement of the solid phase may be intermittent or continuous, continuous movement being envisaged as more common (in this context, movement driven by a stepper motor is considered to be continuous). Similarly, continuous liquid flow is envisaged as normal but the invention includes the use of an intermittent fluid flow. Typically, both the solid phase and the fluid phase move continuously.

After a solid phase has exited an apparatus of the invention, it may move on to one or more further process stations, for example as described later in this specification, at each of which there is performed a process involving the solid phase. Finally, after all processes involving the mobile solid phase have been completed, the solid phase may be reused, suitably after processing for this purpose, cut into lengths and subject to batch processing, e.g. to cleave molecules attached to the solid phase, or disposed of.

Prior art apparatus for treating a mobile solid phase with a liquid phase has, with the exception of an embodiment of PCT GB/2008/002288 (to which priority is claimed), passed the solid phase through a tank of the liquid phase instead of a conduit. The use of a conduit has significant benefits. In particular, the composition of a liquid in a tank and the variation of composition throughout the tank is not controllable. Thus, as a solid phase moves through a tank of liquid reagent or washing liquid, the liquid composition will change as it undergoes reaction or washes unbound substances from the solid phase; moreover, the composition of the liquid phase will change not only in time but also in space, since liquid volumes remote from the solid phase will be relatively unchanged compared to those close to the solid phase. Even if fresh liquid phases continuously charged into a tank, and a corresponding flow discharged, this will not result in adequate control of the liquid composition in the tank, since there will be a complex liquid flow in the tank resulting in different rates of replacement of the liquid in different volumes of the tank. In contrast, the use of a flowing fluid stream permits close control over the composition and continuous refreshing of the fluid. The fluid flow and/or the solid phase movement may be regulated to adjust the conditions in the conduit, for example if monitoring of solid phase which has been through the conduit reveals that the process performed in the conduit has been carried out insufficiently, then the liquid flow rate may be increased. Optionally, this regulation may be automatically under the control of an automated monitoring and control system.

In the same way that the reagent composition in the conduit may be highly responsive to changes in fluid flow, the temperature of liquid in the conduit may be highly responsive to temperature changes of the inflowing fluid.

A particular advantage of the method and apparatus described with reference to FIG. 1 are that they enable counter current movement of the solid phase and the fluid phase. Such counter current treatment ensures that solid phase about to exit the conduit is contacted with the freshest fluid phase which contains the highest concentration of reagent or, in the case of a washing liquid, is at least substantially free from the impurities to be washed from the solid phase. Such counter current processes therefore enable the quality of the solid phase leaving the conduit to be maximized.

FIGS. 2-10 of the drawings illustrate a second embodiment of the apparatus for contacting a mobile elongated solid phase with a flowing fluid phase. It will be recalled that the apparatus comprises a conduit which defines a lumen to contain both the flowing fluid phase and the mobile elongate solid phase as well as fluid phase ports and solid phase ports, both in communication with the lumen and to allow the respective phases to enter the lumen, move through it and exit it, the apparatus being adapted to prevent fluid egress from its interior through the solid phase ports. The apparatus of FIGS. 2-10 is more particularly for use with a fluid phase which is a liquid phase.

FIGS. 2-10 further illustrate another aspect of the invention, namely a modular system for carrying out a heterogeneous process, comprising: a plurality of treatment assemblies 100 for contacting a longitudinally mobile elongate solid phase 1 with a flowing fluid phase, the assemblies 100 being provided in a modular arrangement and each assembly defining a lumen to contain the mobile solid phase and the flowing fluid phase in contact with each other, and each assembly being capable of being releasably connected on first side to a portion of a second said assembly 100 and on a second side to a portion of a third said assembly 100 to form a treatment zone comprising three said treatment assemblies in succession and defining a continuous pathway for an elongate solid phase to move through the treatment assemblies comprised in the treatment zone. The modular arrangement may comprise a module containing a plurality of the treatment assemblies, e.g. arranged in series whereby the assemblies in combination serve to provide a solid phase pathway. The modular arrangement may comprise the individual assemblies 100, or one or more of them, being provided as a module.

It is a feature of apparatuses of the invention, therefore, that they provide a solid phase pathway. Such a pathway may include one or more guide rollers for guiding the solid phase along the pathway, for example for guiding the solid phase outside treatment devices as well as, optionally, within treatment devices. A guide roller may be freely rotating or it may be coupled to a motor for driving the roller and thus the solid phase. One or more guide rollers of an apparatus or system of the invention may be drive rollers in this way.

A modular system for carrying out a heterogeneous process may further comprise one or a combination of: a drive module comprising a controllable drive device for the direct or indirect application of force to the solid phase to move it along the pathway, the system being adapted for the drive module to be mounted such that it remains in fixed position relative to the treatment assemblies during operation of the system; a metering module comprising a controllable fluid metering device for providing a controlled fluid phase flow to the treatment devices, the system being adapted for the fluid metering module to be mounted such that it remains in fixed position relative to the treatment assemblies during operation of the system; a sensor module comprising a sensor arranged to detect a parameter of the solid phase after the solid phase has passed through the treatment zone, the system being adapted for the sensor module to be mounted such that it remains in fixed position relative to the treatment assemblies during operation of the system; a sensor module comprising a sensor arranged to detect a parameter of the fluid phase after the fluid phase has passed through the treatment zone, the system being adapted for the sensor module to be mounted such that it remains in fixed position relative to the treatment assemblies during operation of the system; a processor adapted to be in signal communication with the sensor and with at least one of the drive device and the fluid metering device to receive an input signal from the sensor and send an output signal to the at least one of the drive device and the fluid metering device, the processor being programmed to control the at least one of the drive device and the fluid metering device responsive to the detected parameter. In embodiments the modular system does not include the drive device.

The modular system may further include a framework on which the treatment assemblies, the drive module, the metering module and the sensor module are adapted to be mounted. At least some of the treatment assemblies may be arranged in one or more treatment device stacks, the or each stack being a module comprising a housing in which are accommodated a plurality of treatment assemblies which are coupled together and which are in, or are capable of being put in, fluid communication with a common fluid source for the treatment devices of that stack, the or each stack being adapted to be mounted on the framework.

Included in the disclosure is a modular system for carrying out a heterogeneous process, the system comprising a plurality of treatment devices 100 for contacting a longitudinally mobile elongate solid phase with a flowing fluid phase. Each device 100 may be described as constituting a unit and, in any event, defines a lumen to contain the mobile solid phase and the flowing fluid phase in contact with each other. The devices are held together as a module or "stack" comprising the plurality of modules. The plurality of treatment devices 100 define a continuous pathway for an elongate solid phase to move through successive devices of the plurality in an upstream to downstream direction.

More particularly, FIGS. 2-10 illustrate a modular system for carrying out a heterogeneous process which comprises a plurality of such treatment devices 100, in which each device is adapted for releasable connection on an upstream site to a second such device 100 and a downstream site of third said device 100 to form a treatment zone defining a continuous pathway for an elongate solid phase to move through successive devices in an upstream to downstream direction. Such a modular system enables assembly of stacks comprising any desired number of individual treatment devices, i.e. whilst providing modules or stacks of treatment devices 100, the system enables complete flexibility as to the chosen size of such stacks.

It will be understood that, in the embodiment illustrated by FIGS. 2-10, each treatment device 100 constitutes an apparatus for contacting a mobile elongate solid phase with a flowing fluid phase as previously mentioned. More particularly, the fluid phase is a liquid phase. As will be described in greater detail later, the apparatus is adapted such that, when it is in an upright orientation, the solid phase ports 107, 108 are spaced above the fluid phase ports 109, 110.

As will also be explained in more detail later, FIGS. 2-10 are illustrative of a class of embodiments in which the conduit 103 comprises a region in which it undergoes a change of direction. More particularly, FIGS. 2-10 illustrate members of this class of embodiment in which the conduit 103 comprises two arms which are inter-connected by the region in which the conduit undergoes a change in direction, the apparatus being configured for the two arms to be upright and in fluid interconnection at lower ends thereof when the apparatus is in its operative configuration (is in use). FIGS. 2-10 also illustrate members of the class of embodiments in which the conduit comprises a region in which it undergoes a change in direction in which the region comprises a roller 115 whose axis of rotation is transverse to the direction and movement of the solid phase and which is arranged to guide the solid phase through its change of direction.

Similarly to FIG. 1, the embodiment of FIGS. 2-10 discloses an apparatus in which the conduit 103 is defined by a plurality of releasable interconnected plates, the plates comprising a pair of plates in opposed face-to-face relationship and the opposed faces having defined between them a length of the conduit extending in a direction parallel with the pair of plates. More particularly, each treatment device or apparatus 100 illustrated in FIGS. 2-10 is shown to comprise three plates 116, 117 and 118. The plates 116, 117 and 118 are typically of generally cuboidal shape and, irrespective of their shape, they each comprise two opposed faces. The three plates of each device are interconnected in face-to-face relationship, the interconnection normally being releasable as illustrated in the figures, to facilitate disassembly of each device, for the purpose of cleaning or dismantling. The three plates are interconnected such that there is an intermediate plate 117 between a first end plate 116 and a second end plate 118, the interconnected plates forming a unit having an upper end 119 which is disposed to the top of the unit when the unit is in use and a lower end 120 which is disposed to the bottom of the unit when the unit is orientated for use. The intermediate plate 117 has an aperture 121 defined therein towards the lower end 120 of the unit to define a channel between the two faces of the intermediate plate 117. The aperture 121 has the roller 115 rotatably arranged therein.

The first end plate 116 and the intermediate plate 117 define between them a first arm of the conduit, whilst the second end plate 118 and the intermediate plate 118 define between them a second arm of the conduit, the two arms extending in a direction from the top of the unit to the bottom of the unit and each terminate at, and in fluid connection with, the aperture 121. The two arms of the conduit each have an upper region in communication with the solid phase ports 107,108 and with the fluid phase ports 109,110, the solid phase port of each arm being spaced upwardly from the fluid face port of the arm. Normally, the two solid phase ports of each unit are spaced upwardly from the two fluid phase ports of each unit. It will be observed in the illustrated embodiment that both of the solid phase ports 109 and 110 are spaced above both of the liquid phase ports 107 and 108, which is a feature of certain embodiments of the invention which are adapted for use with a fluid phase which is liquid. The apparatus of FIGS. 2-10 therefore uses gravity to separate the solid phase from the liquid phase and, as previously mentioned, this is a feature of many embodiments of the invention. As an alternative to using gravity to separate the liquid phase from the solid phase in apparatuses of the invention, suitable seals may be used, and this is a feature of apparatuses adapted for use with fluid phases which are gaseous.

Figure 4:
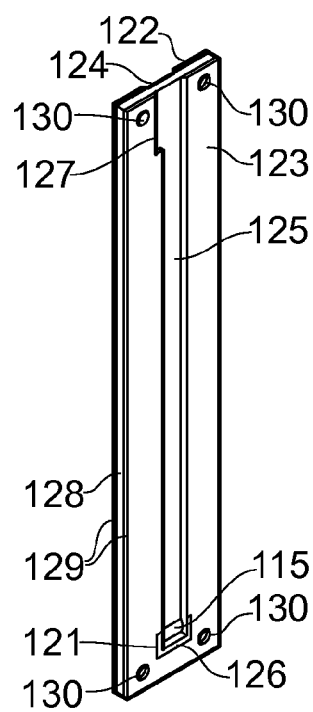
FIG. 4 is a perspective view of a central plate featured in FIG. 2.
Figure 5:
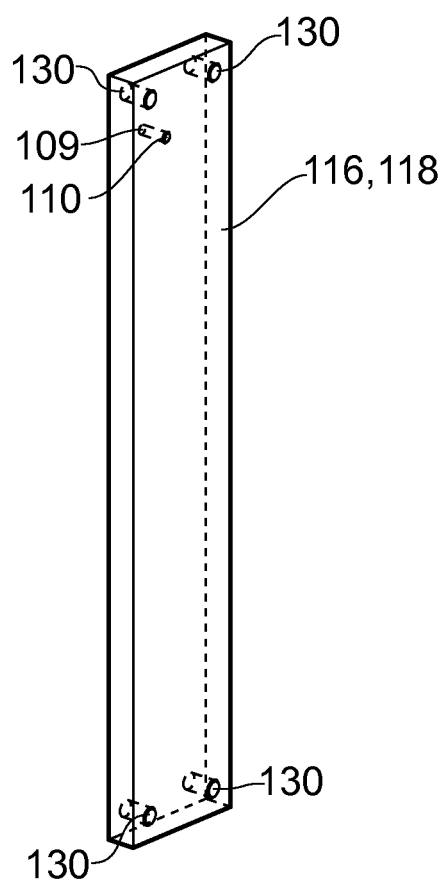
FIG. 5 is a perspective view of end plates featured in FIG. 2.

Looking more particularly at the embodiment of FIGS. 2-10, an intermediate plate 117 is depicted in FIG. 5. It will be seen that the intermediate plate 117 has opposed faces 122 and 123. Each of the opposed faces 122 and 123 has defined therein a respective channel 124,125. The channels 124,125 extend from the upper end of the intermediate plate 117 to the through aperture 121 which defines a channel between the two opposed faces 122,123 of the intermediate plate 117. A portion of the aperture 121 is occupied by the roller 115 and, in the illustrated embodiment, a bearing 126 in which the roller 115 is rotatably mounted. The bearing 126 fits snugly in the aperture 121 in the illustrated embodiment. In some embodiments, fastening means are provided to hold the bearing 126 in the aperture 121. In any event, the centre plate 117 normally, but not always, has a roller 115 mounted in the aperture 121. It will be noted that a channel for passage of the solid phase and the liquid phase is defined between the roller 115 and the bearing 126; irrespective of the design of the aperture 121 and any associated roller and optional bearing, it is a feature of the illustrated embodiment that the intermediate plate 117 in the completed unit 100 has defined therein a through channel for passage of both the solid phase and the liquid phase from one side of the intermediate plate 117 to the other.

The two end plates 116 and 118 are conveniently of identical design, in order to reduce the number of different components. This is not a requirement of the invention, however.

As described in relation to FIG. 1, it is advantageous for the interfacing faces of the three plates 116, 117, 118 to be as flat as possible in order to reduce or prevent fluid leakage. Additionally or alternatively, and as also described in relation to FIG. 1, a solid gasket or a so-called "liquid gasket" may be provided at the interface between plates. As a liquid gasket may be used a grease insoluble in the solvent to be used in the treatment device. In one example, a silicone grease is used as a liquid gasket, e.g. is smeared over the mating surfaces of the plates. As a solid gasket may be mentioned a PTFE sheet. A dual containment system may be used which has two gaskets, e.g. two solid gaskets or a solid gasket and a liquid gasket.

Each of the opposed faces 122 and 123 of each intermediate plate 117 therefore provides a respective channel 124 or 125 which, in the completed apparatus, is open in a direction facing the respective end plate 116 or 118. It will be recalled that, in the completed apparatus, the first end plate 116 is in face-to-face relationship with a respective face 122,123 of an intermediate plate 117. The channel 124 and its facing end plate 116 define the first arm of the conduit of apparatus 100 whilst the channel 125 and its facing end plate 118 define the second arm of the conduit. The two arms of the conduit are in communication with each other through the aperture 121, and in the illustrated embodiment more specifically through the free volume formed between the optional roller 115 and its optional bearing 126.

As can be seen most clearly in FIG. 4, the channel 125 has a widened upper region 127 and the opposed channel 124 is of mirror image construction. It will therefore be seen that FIG. 4 illustrates embodiments of the invention in which the first and second arms have an upper region of greater cross-sectional area than the remainder of the channel. The lower and narrower region of the channel 125, which occupies a majority of its length, is in the illustrated embodiment designed as a snug fit for an elongate solid phase in the form of a ribbon. This is illustrative of an optional feature of the invention that the lumen of a conduit accommodates a solid phase in a relatively snug fit; for example, this may avoid any risk of static volumes of fluid forming. In the illustrated embodiment, the channel 125 is in the form of a trough having three walls arranged as three walls of a rectangle. In the illustrated embodiment, the longer wall of the rectangle, i.e. the base of the trough, has a width of 22 mm or a little more than 22 mm (e.g. 23-24 mm), in order to snugly accommodate a ribbon having a width of 22 mm. The depth of the trough (the height of the shorter walls) is conveniently from 1.2 mm to 2.5 mm, e.g. 1.5 mm to 2 mm. It has been found that, in the case of a channel in the form of a trough-cross-sectional dimensions of 22 mm×2 mm, there can be a risk of the moving solid phase (moving ribbon) tending to pull a meniscus at the top of the liquid phase out of the top of the channel 125, to cause spillage of liquid. It has been found that provision of an upper region whose width is increased from 22 mm to 27 mm significantly reduces the risk of liquid spillage. It is believed that, in general terms, where an apparatus of the invention has a conduit comprising an upstanding region terminating at its upper end at an open solid phase port, any risk of liquid spillage from the solid phase port can be reduced by increasing the cross-sectional are of an upper region of the channel adjacent to the solid phase port. It is further believed that many factors will affect the risk of spillage through liquid being pulled out of a solid phase port, including the running speed of the solid phase, the identify of the solid phase material, the composition of the liquid phase and the dimensions of the conduit, and it is therefore not possible to specify in what circumstances apparatus would benefit from having a conduit region of enlarged cross-sectional area adjacent an upward facing solid phase port. Nonetheless, it can be stated in general terms that the provision of such a region of increased cross-sectional area adjacent an upward facing solid phase port will reduce any risk of liquid spillage out of the solid phase port.

As has already been described, each of the opposed faces 122, 123 of the intermediate plate 117 is engaged by a respective end plate 116,118 to close the outward facing opening of the respective channel. In order to reduce the number of different component designs, it is convenient, but far from essential, that the first end plate 116 and the second end plate 118 share a common design. Accordingly, FIG. 5 illustrates an end plate 116 and an identical end plate 118. The end plate 116 has defined therein a fluid phase port 109 which in use is in fluid communication with the conduit arm defined by the channel 125 of a facing intermediate plate 117 and the end plate 116. Similarly, the end plate 118 has defined therein a fluid phase port which communicates with the conduit arm defined by the channel 124 of facing end plate 117. The fluid phase ports 109, 110 in use provide communication between the conduit of an apparatus and a fluid outflow line. In the embodiment of FIGS. 2-10 it happens that the fluid phase ports are defined as the openings of a through hole between opposed faces of the respective end plate 116,118.

In summary, each apparatus 100 of the embodiment of FIGS. 2-10 comprises a centre plate having opposed faces, each of which engages a corresponding face of an end plate. Each end plate and its engaging face of the intermediate plate define between them a conduit arm which, when the apparatus is orientated for use, extends from an upwardly facing solid phase port defined at an upper end of the apparatus to a through aperture between the two faces of the centre plate, the through aperture providing a volume through which the solid phase and the liquid phase may pass during use of the apparatus. The through aperture is typically arranged towards the lower end of the centre plate. Each arm of the conduit may be defined by a channel in the respective face of the centre plate in engagement with its adjacent end plate or, as depicted in PCT/GB2008/002288, each arm of the conduit may be defined between a channel formed in a face of each end plate and the engaging face of the centre plate. However, the invention is not restricted to these two arrangements and other constructions are contemplated, including the provision of channels in both faces of the centre plate and in the engaging faces of the end plates, as well as asymmetric arrangements in which one arm of the conduit is defined by a channel in the centre plate and an engaging planar face of an end plate whilst the other arm of the channel is defined by a planar face of the centre plate and a channel defined in the engaging face of the abutting end plate.

It will be noted that, in the centre plate illustrated in FIG. 4, the centre plate is of laminar construction, in comprising a centre panel and respective slotted laminas 129, the side walls of the slots defining the side walls of the trough-shaped channels 124 and 125. This is just one possible construction of the centre plate, since many other variants are possible, including a one-piece centre plate.

In use, the three plates of each device 100 are interconnected, whether permanently or releasably. In this regard, it is preferred for the interconnection to the releasable, to enable the device to be disassembled for cleaning or other purposes. Typically, the plates are releasably clamped together. Conveniently, such clamping may be performed by a releasable fastener, for example by a bolt and nut arrangement. To that end, the end plates 116 and 118 and the centre plate 117 have defined therein bolt holes. In the assembled unit 100, each bolt hole of each plate is in alignment with a corresponding bolt hole in the other two plates and each set of aligned bolt holes accommodates a bolt or other fastener.

Each device 100 illustrated in FIGS. 2, 3, 6, 7 and 8 is shown in those figures to be incorporated in a modular system comprising a plurality of treatment devices, the treatment devices forming a treatment zone defining a continuous pathway for an elongate solid phase to move through successive devices. The plural devices together form a device stack and, in the assembled stack, the individual devices are releasably connected to each other. Indeed, in the illustrated embodiment, the stack consists of individual plates fastened together to form the end plates and centre plates of respective devices. There is therefore illustrated a stack of treatment devices, the stack being comprised of a plurality of plates in face-to-face engagement to define respective treatment devices, each treatment device comprising a centre plate having opposed faces, each face being engaged with a respective end plate, each of the opposed faces of the centre plate and its engaged end plate defining there between an arm of a conduit and the two conduit arms are in communication whereby there is formed a conduit defining a lumen adapted to accommodate a mobile elongate solid phase and a flowing liquid phase in contact with each other. Access ports are provided to enable the solid phase and the liquid phase to enter and leave the conduit, the solid phase ports optionally being defined as an upwardly facing mouth of the two arms, the fluid phase ports being spaced below the solid phase ports to enable substantial separation of the two phases by gravity.

In the depicted embodiment, each device 100 comprises its own distinct set of three plates 116, 117 and 118. Positioned between the end plates of adjacent treatment devices 100 are spacer plates 130, one or more spacer plates 130 being disposed between adjoining end plates. In the illustrated embodiment, the spacer plates 130 are of similar design to the end plates 116 and 118 and include a through hole to provide a continuous liquid channel between the joining treatment devices 100, whereby, for example, liquid may leave a first device 100 through a fluid phase port 109 and then travel to a fluid phase port 110 of an adjacent second treatment device 100 via through holes in an end plate 116 of the first treatment device, the intercommunicating through hole of a spacer plate 131 and intercommunicating through hole of an engaging end plate 118 of the second treatment device 100. The spacer plates are provided to permit space for rollers to be positioned along the solid phase pathway between each device 100; such rollers are described later, in particular with reference to FIGS. 7 and 8.

Figure 6:
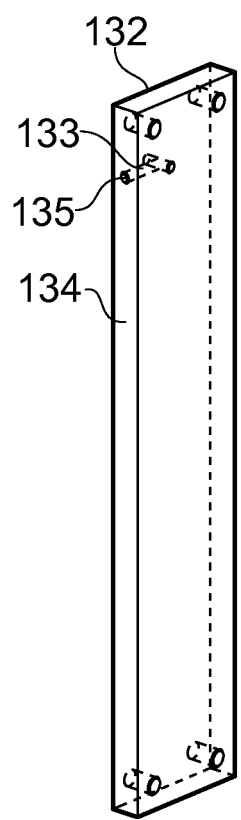
FIG. 6 is a perspective view of a terminal plate featured in FIG. 2.

In the illustrated embodiment, the stack of treatment devices has terminal plates 132 of different design to the spacer plates 131, although in other embodiments the terminal plates and spacer plates are of identical design. As illustrated by FIG. 6, the terminal plates 132 have a through hole which, in the assembled stack, is in liquid communication with a corresponding through hole in adjacent end plate 116 or 118, to provide for liquid to enter and leave the adjacent treatment device 100. In the Figures, the through hole 133 is shown to include a right angle bend so that it terminates at a side gate 134 of the terminal plate 132.

The treatment device stack illustrated by FIGS. 2-9 comprise a plurality of treatment devices which provide a continuous liquid flow path between a terminal liquid port 135 of a first terminal plate 132 to a second terminal fluid port 135 of a second terminal plate 132. The liquid ports of successive treatment devices 100 are therefore in liquid communication with each other to provide a liquid fluid path from one treatment device 100 to the next. In alternative embodiments, however, the spacer plates 131 do not contain a through hole to provide liquid communication between the successive treatment devices on either side of the spacer plate 131 but, instead, the spacer plates provide accessible liquid ports in an edge of the spacer plate to enable liquid to enter and leave the stack through the accessible liquid ports, each spacer plate suitably having a first accessible liquid access port in communication with a first treatment device 100 and a second accessible liquid port in communication with a fluid phase port of a second treatment device 100.

In some embodiments of the treatment device stacks of the invention, the spacer plates 131 are dispensed with entirely whereas, as previously mentioned, other embodiments include a plurality of spacer plates between successive treatment devices 100. The invention further includes stacks in which adjacent treatment devices 100 share common end plates, such that the stack comprises a plurality of centre plates 117, adjacent ones of which are separated by a single plate serving as an end plate for both of the successive treatment devices 100.

It will be recalled that the stack of treatment devices may define a single liquid flow path through the successive devices of the stack or, alternatively, the liquid flow path of each treatment device may be unconnected to the liquid flow path of each other treatment device or, as a yet further alternative, at least two successive treatment devices may lie along a common flow path whilst at least one other treatment device lies on an unconnected liquid flow path. However, a different situation applies in relation to the elongate solid phase, since all the treatment devices of a stack serve to provide a common treatment zone for the same solid phase. Accordingly, a solid phase pathway is defined between successive treatment devices, to allow the solid phase to leave the conduit of a first treatment device through a solid phase port thereof and enter a solid phase port of the next successive treatment device. To that end, guide rollers may be provided between successive treatment devices, as illustrated by way of example by FIGS. 7 and 8.

FIGS. 7-10 illustrate a treatment device stack 99 which includes, in addition to treatment devices 100 and any spacer plates 131 and terminal plates 132 a housing in which are accommodated the treatment devices and associated components, including guide rollers, as will next be described.

Figure 7:
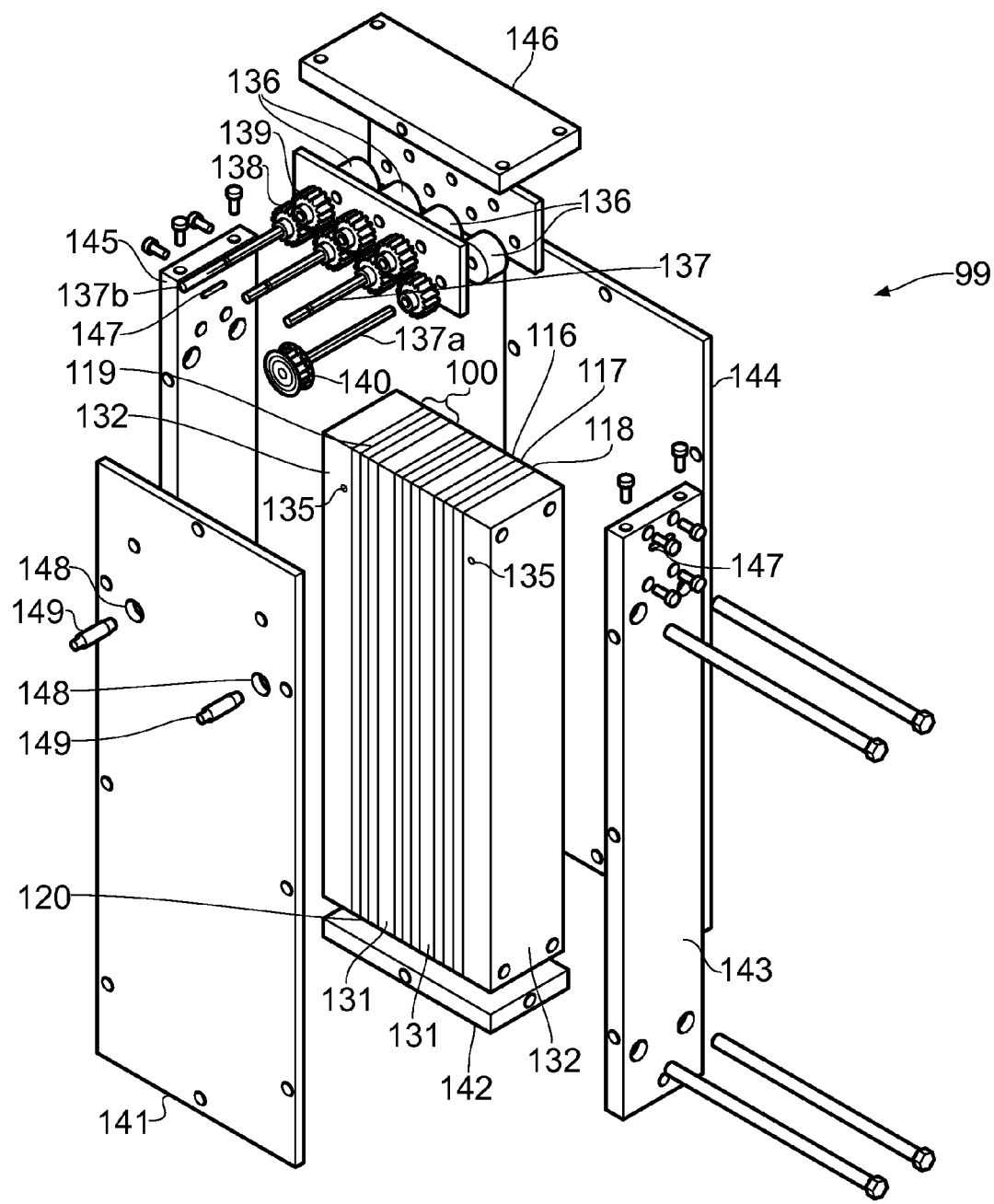
FIG. 7 is an exploded perspective view of a module incorporating a combination of apparatuses according to the second embodiment of the invention.

Accordingly, FIG. 7 shows a plurality of rotatable rollers 136 arranged to guide the solid phase along its pathway. Specifically, there are shown rollers 136 to guide the solid phase between treatment devices 100 (in this case the two middle rollers serve to guide the solid phase between the three treatment devices 100 of the illustrated stack) and also rollers 136 disposed to guide the solid phase outside the first and last treatment devices of the stack.

Figure 8:
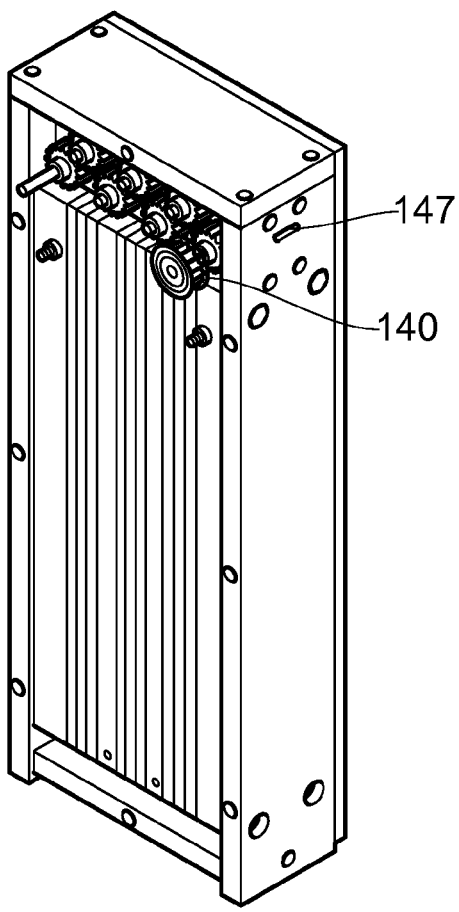
FIGS. 8 and 9 show the module of FIG. 7 respectively in partially and completely assembled form.

Each roller may be freely rotatable or it may be driven so that it may act as a drive roller to cause the solid phase to move. For example, there may be a single driven roller or a plurality of driven rollers and, as shown in FIGS. 7 and 8, all of the rollers may be driven. Thus, each roller 136 is mounted on an axle 137 and each axle 137 has a gear wheel 138 mounted on the axle for rotation therewith. In the illustrated embodiment, there are four rollers and, accordingly, four axles 137 and four associated gears 138, but FIGS. 7 and 8 illustrate just one arrangement amongst numerous other possibilities. The gear wheels 138 are coupled together through intermediate gear wheels 139 which freely rotate on respective axles (which are not shown for reasons of clarity). One of the roller axles 137, in this case the axle depicted 137*a*, is adapted to be driven by an electric motor or other suitable drive device, in this case by having mounted thereto for rotation therewith a wheel 140 to be engaged with a drive belt or drive chain (not shown). The driven axle 137*a* may alternatively be arranged to be driven by a motor directly or through one or more gears. It is emphasized again at this point that the precise arrangement of the rollers 136 is not of importance, whilst it will be borne in mind that FIGS. 7-9 are illustrative of embodiments in which at least one roller associated with the treatment device stack is a drive roller, adapted to be coupled to, or in the state of being coupled to, an electric motor or other drive apparatus.

In embodiments, the driven axle 137*a* is capable of being coupled to a motor or other drive apparatus through one or more intermediate stacks of treatment devices. It is a feature of some embodiments of the invention, therefore, that the treatment devices are arranged in modular stacks each comprising a drive system comprising a roller for moving the solid phase and wherein the stacks are adapted for the drive systems of adjacent stacks to be connected; in this way, a motor or other drive apparatus coupled to the drive system of a first stack may drive the drive systems of one or more further stacks through the intermediary of the first stack. In the embodiment of FIGS. 7-10, the stack includes a drive axle designated 137*b* which may be coupled to a second stack to drive the rollers of the second stack, for example via a wheel 140*b* (omitted from FIGS. 7-9 for clarity) mounted on the drive axle 137*b* for rotation therewith and a belt or chain coupling the roller with a driven wheel 140 of the second stack.

Figure 9:
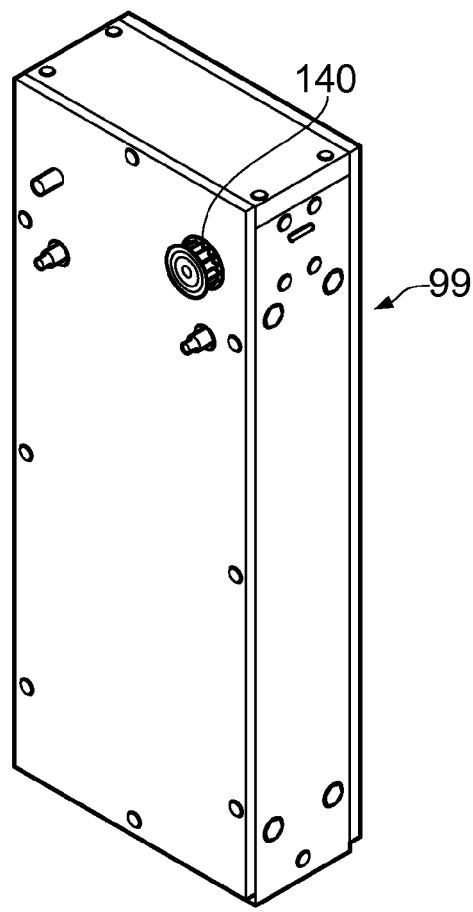

The remainder of the housing will not be described in detail, since its construction is readily apparent from FIGS. 7, 8 and 9. It will be seen that the housing in this case comprises six side panels 141-146 which may be bolted together to form the six sides of a cuboidal box. The drive belt wheel 140 remains exposed and access is provided for the elongate solid phase, in this case by slots 147. The housing defined by side panels 141-146 also provides access to a fluidics system (comprising a fluid source and a fluid outlet line), in this case by means of fluidics access holes 149 and optional connectors 150 which couple in liquid tight manner with terminal liquid phase port 135.

Figure 10:
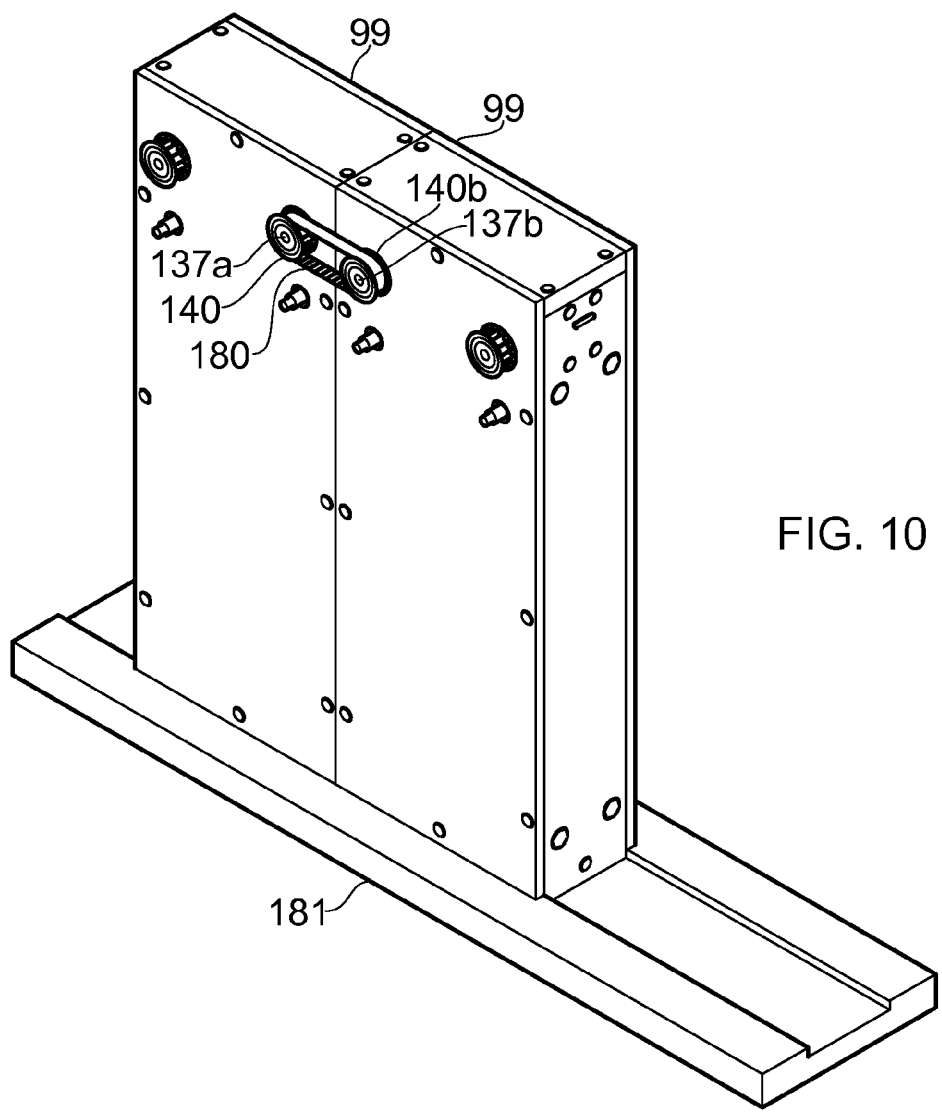
FIG. 10 is a perspective view of a portion of a framework showing two modules of FIG. 7 mounted on the framework, the two modules having respective roller drive systems which are coupled together.

FIG. 10 illustrates two modular treatment stacks mounted in a framework. The roller drive systems of the two stacks 99 are coupled together so that the roller drive system of one stack may be driven by the roller drive system of the other stack, which is in turn coupled to a motor or other drive. Specifically, a drive wheel 140b of a first stack is coupled by a belt 180 to a driven wheel 140 of a second stack. The modules 99 are adapted for mounting on a framework, represented by a rail 181.

An elongate solid phase may be threaded through a stack 99 when a panel thereof is removed, as illustrated for example by FIG. 8. In embodiments, a stack is adapted for automatic feeding of a solid phase through it.

Exemplary dimensions of a device of a conduit of a device of the disclosure have been described previously in this specification. Where the length of a conduit is insufficient for a process to be adequately completed in a single unit, a process may be carried out in a plurality of such units arranged in series, whereby the total length of conduit within which the process is performed is extended. It will be recalled that such plural units may conveniently be accommodated in a single module or stack, for which purpose all the devices within a module or stack are conveniently in fluid communication with a common fluid source, whether through one or more intervening treatment units or not.

In embodiments of the invention, an energy source is arranged to expose to energy at least part of the lumen of an apparatus for contacting a mobile elongate solid phase with a flowing fluid phase. The energy source may comprise an ultrasound transducer, a magnetron, a laser, a light emitting diode, a mercury vapour lamp or other UV source, or another source of electromagnetic radiation, or a heat source. It will be appreciated that a combination of energy sources may be provided to enable the lumen to be exposed to energy from more than one energy source, whether at the same time or separate times. Examples of apparatus incorporating such energy sources are provided by FIGS. 11, 12 and 13.

Figure 11:
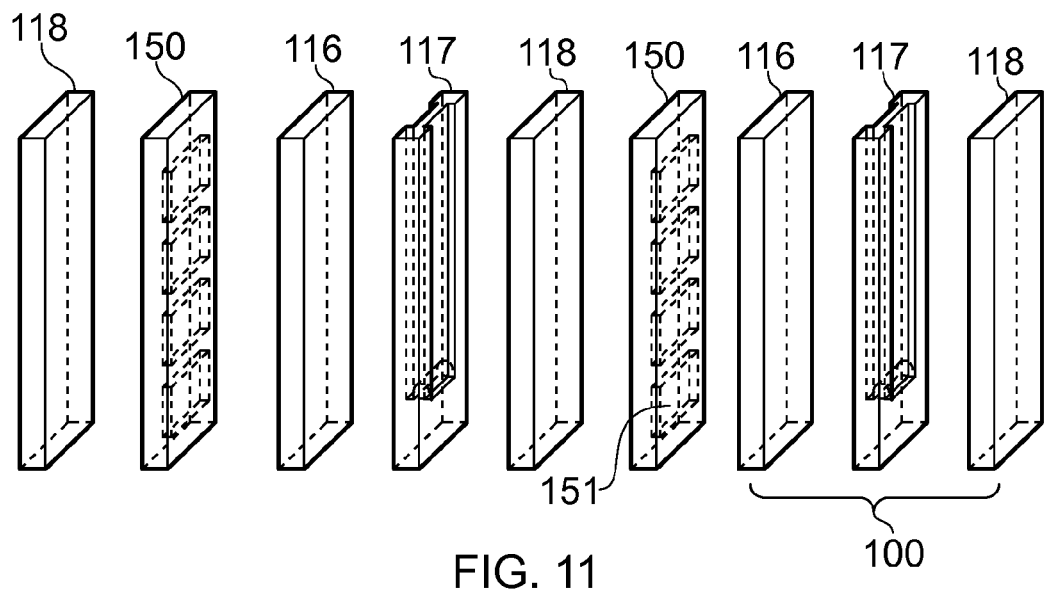
FIG. 11 is an exploded perspective view of plates and roller bearings forming a combination of apparatuses according to a third embodiment of the invention.

FIG. 11 is an exploded view of the plates constituting the treatment devices 100 of a treatment device stack which incorporates ultrasound transducers. As in the case of the embodiment of FIGS. 2-9, each treatment device 100 comprises a centre plate 117 and end plate 116,118 together defining a conduit and its associated ports. A spacer plate is provided between adjacent treatment device 100. In this case, the spacer plate is in the form of a transducer plate 150, comprising one or more ultrasound transducers 151 which may be coupled to a suitable electricity supply. As in the case of the embodiment of FIGS. 2-9, the transducer plates 150 may contain a through hole to provide liquid communication between the successive treatment devices 100, so that the treatment devices are arranged along a common liquid flow path. Alternatively, the liquid flow path of each treatment device may be unconnected to the liquid flow path of every other treatment device, or some of the treatment devices may be disposed along a common liquid flow path whilst at least one other device does not share the same liquid flow path. The transducers 151 may be replaced by, or supplemented by, another energy source, for example a source of electromagnetic radiation, for example ultraviolet or visible light. In this case, the end plates 116, 118 are made of a suitable material for the end plate to allow passage of the electromagnetic radiation.

Figure 12:
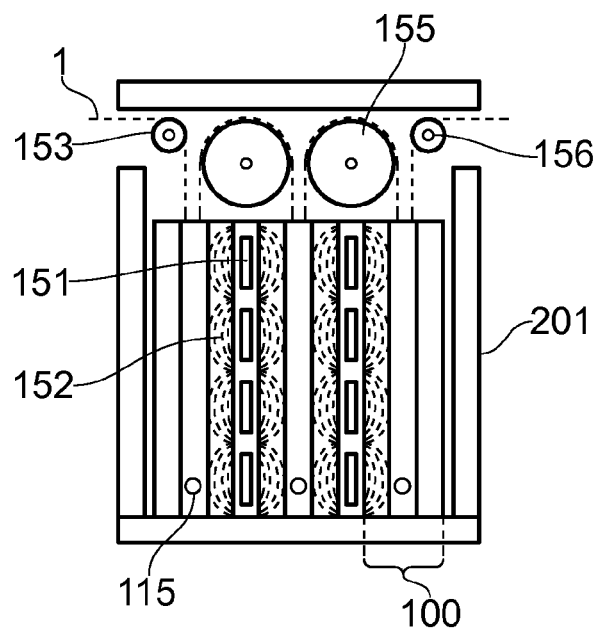
FIG. 12 is a diagrammatic side view of a module incorporation a combination of apparatuses according to the third embodiment of the invention.

In variants of the apparatus of FIGS. 11 and 12, the intermediate end plates 116, 118 between treatment devices are dispensed with, and the transducer plate 150 (or an alternative energy source plate containing one or more additional or alternative energy sources) acts as a common end plate for the treatment devices on the opposed sides of the transducer plate 150.

FIG. 12 illustrates the treatment device stack in operation. The ultrasound transducers 151 are shown to be emitting acoustic energy indicated by dotted lines 152 which enter a portion of the lumen of each treatment device to expose the solid phase and the contacting liquid phase to the ultrasound energy, in order to accelerate a reaction between a reagent in the liquid phase and a reagent attached to the solid phase. More particularly, an elongate solid phase 1, particularly a ribbon, is guided over a roller 153 and enters a first arm of a conduit. The solid phase 1 passes down the arm of the conduit to a roller 115 disposed in a through-aperture in the centre plate 117, passes over the roller and up a second arm of the conduit before being guided by a roller 154 into a second treatment device, after which the solid phase passes over a further roller 154 into a third treatment device, after leaving which the solid phase passes over a roller 154 before leaving the stack.

Figure 13:
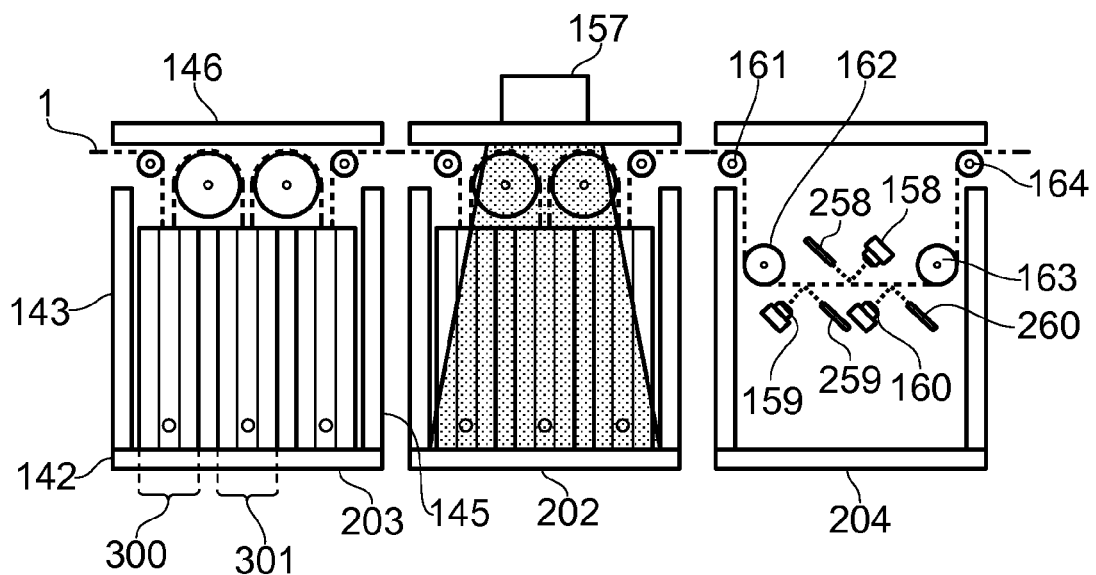
FIG. 13 is a diagrammatic side view of a part of dual mobile phase system according to the invention.

FIG. 13 illustrates a treatment device stack 202 in which a magnetron (microwave source) is provided above the treatment devices 100 to expose at least a portion of each lumen within the stack to microwave radiation.

FIG. 13 also illustrates an aspect of the invention which resides in a system for subjecting a longitudinally mobile elongate solid phase to apply to yield successive treatments, comprising a plurality of phase contact devices for contacting the mobile elongate solid phase with a flowing fluid phase. Each phase contactable device comprises (i) a conduit which is circular or non-circular in transverse cross-section and defines a lumen to contain both the flowing fluid phase and the mobile elongate solid phase, (ii) fluid phase ports in communication with the lumen to allow the fluid phase to enter the lumen, flow through it and exit it, and (iii) solid phase ports in communication with the lumen to allow the mobile solid phase to enter the lumen, move through it and exit it. In the illustrated embodiment, the phase content devices are represented by treatment devices 100. The systems arranged for a solid phase pathway to be defined between successive phase contact devices such that the solid phase may move through the successive phase contact devices one after another. A first phase contact device 300 and a second phase contact device 301 are disposed in succession along the pathway and are arranged to receive fluid from a common first fluid source. A third phase contact device 302 along the pathway is arranged to receive fluid from a second fluid source.

More particularly, FIG. 13 illustrates a system in which the first phase contact device 300 and the second phase contact device 301 are arranged to receive fluids from the first fluid source in that a fluid phase port of the first phase contact device 300 is in fluid communication with a fluid phase port of the second phase contact device whereby fluid is able to flow from the first phase contact device to the second phase contact device.

As illustrated in FIG. 13, the first phase contact device 300 and the second phase contact device 301 are releasably coupled together and, more particularly, are both disposed in the same phase contact device stack. Considering the system of FIG. 13 as a whole, it will be observed that it illustrates a system having successive phase contact devices in which at least some of the devices are arranged in one or more phase contact device stacks, the or each stack comprising a plurality of phase contact devices which are coupled together, and may be coupled together releasably. The phase contact devices of each module are typically in, or are capable of being put in, fluid communication with a common fluid source for the phase contact modules of that stack.

As illustrated by FIG. 13, each treatment device stack 202, 203 includes a housing, which in the illustrated embodiment includes side panels, including those identified as side panels 142,143,145 and 146. The housing of each stack accommodates the phase contact devices of that stack and is connected to rollers arranged to guide the solid phase along the solid phase pathway outside the phase contact devices. The stacks 202,203 illustrated by FIG. 13 are shown to include four rollers accommodated in the stack housing; the number of rollers is necessarily variable, depending upon the number of phase contact devices and the rollers connected to the housing may include one or more rollers arranged outside the housing, usually as well as one or more rollers inside the housing. Optionally, at least one roller of each stack (i.e. at least one of the rollers connected to the housing of a stack) is a drive roller connected with, or capable of being connected with, a drive device for causing the roller to rotate and drive the solid phase. The stack 202 may comprise a magnetron 157 for emitting microwaves or another energy source, to expose the interior of the conduit to energy. In this case, the energy comprises microwaves indicated by the stippled area generally under the magnetron 157.

FIG. 13 illustrates a solid phase pathway which comprises two treatment stacks, 202, 203 and, downstream from stack 202, a sensor module 204 comprising a sensor device (FIG. 13 illustrates a sensor module 204 containing three sensor devices) for determining a parameter of the solid phase as it moves along the pathway. It will therefore be noted that FIG. 13 illustrates a system as disclosed herein for subjecting a longitudinally mobile elongated solid phase to a plurality of successive treatments, which system includes a sensor device arranged outside successive phase contact devices of the system for determining a parameter of the solid phase as it moves along the solid phase pathway. The sensor device typically comprises a detector of electromagnetic radiation, for example this may detect fluorescence from one or more fluorescent labels, for example a fluorescent dye, semi-conductor nanocrystals or combinations thereof. The sensor may comprise a spectrometer, for example a UV spectrometer. The sensor may detect any other detectable label or any other detectable parameter of the solid phase. It is in particular contemplated that UV and/or IR spectrometers will be of value in forming a chemical analysis of any solid phase which has been used as a support for solid phase synthesis, as a tool to measure purity and/or whether a chemical reaction has gone to completion. In other embodiments, the sensor may be useful for detecting binding of a label substance to an analyte coupled to the solid phase; suitable labels for these and other purposes include radionuclides, fluorescent substances (e.g. dyes or semiconductor nanocrystals), luminescence substances and magnetic substances (e.g. magnetic particles).

In the particular arrangement illustrated in FIG. 13, three spectrometers 158, 159, 160 are arranged in a detection module 204. Each spectrometer comprises a radiation source 258, 259, 260 and a radiation detector 158, 159, 160. FIG. 13 schematically shows by broken lines radiation emitted from each source and reflected off the solid phase 1 to be received by the respective detector. Where a system comprises plural sensors arranged in a common detection zone, similar to the arrangement of FIG. 12, each sensor may be different from all the others or, alternatively, at least two of the plural sensors may be the same, for example serving for verification of the detected parameter.

As shown in FIG. 13, appropriate rollers are provided along the solid phase pathway outside the phase contact device stacks 202, 203, and in FIG. 13 these rollers outside the stacks 202, 203 comprise rollers 161-164 associated with the detection zone.

FIG. 13, similarly to FIGS. 9, 10 and 12, serves also to illustrate an additional feature of many embodiments of the disclosure, namely modularity. Modular systems and apparatuses comprise those in which at least a portion of the components are provided as modules, i.e. as self-contained components which can be interchanged, added to the system, removed from the system or combined to form at least part of the system without disassembly of the modules. Suitably, such a modular system comprises a framework (not shown) to which modular components of the system are releasably coupleable. A system of the disclosure for subjecting a longitudinally mobile elongate solid phase to a plurality of successive treatments may therefore be a modular system which comprises a framework on which modular phase contact devices and optionally one or more additional modular components of the system may be mounted, e.g. releasably coupled, along the solid phase pathway. Typically, at least some of the successive phase contact modules are arranged in one or more modular phase contact module stacks, although this is not an essential feature of such a modular system. Where a modular system includes modular stacks, each comprises a plurality of phase contact devices which are coupled together (e.g. by clamping) and which in some embodiments are in, or are capable of being put in, fluid communication with a common fluid source for the phase contact devices of that stack. Accordingly, in a system of the disclosure in which a first phase contact device and a second phase contact device are disposed in succession along the solid phase pathway and are arranged to receive fluid from a common first fluid source, the system typically comprises phase contact device stacks and the first and second phase contact devices are typically disposed in the same stack. As illustrated in FIG. 13, such a modular system may further include a modular sensor device, illustrated as module 204. In variants of the system, the modular sensor device 204 is replaced by, or supplemented with, a modular deposition device for depositing a reagent or solvent on the solid phase as it moves along the pathway. Such a modular deposition device may be similar to module 204 but have sensor devices 158,159,160 replaced by one or more deposition heads, for example inkjet heads, as described next.

Figure 14:
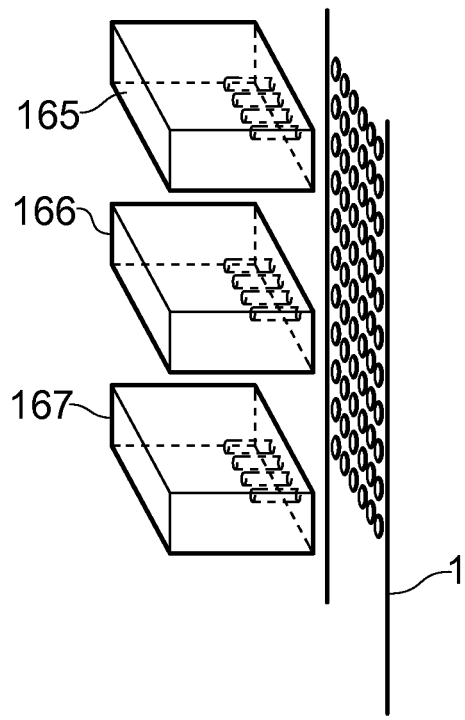
FIG. 14 is a diagrammatic perspective view of a deposition zone of a system according to the invention.

FIG. 14, therefore, illustrates a deposition zone of an apparatus or system of the disclosure, the deposition zone comprising at least one deposition device or head. In the case of FIG. 14 there are three deposition devices 165, 166 and 167. The or each deposition device is adapted to deposit a reagent onto the solid phase 1 as the solid phase moves along the pathway. It will be understood that the reagent deposited by deposition heads may include a combination of reagents, for example a synthetic building block and a catalyst or activator, and that the reagent (whether a single reagent or a reagent combination) will typically be deposited in solution or dispersion in a liquid vehicle. Exemplary deposition devices are single fluid piezoelectric dispensers or multifluid piezoelectric dispensers, similar to those used in inkjet printers. However, any controllable deposition device may be used.

Figure 15:
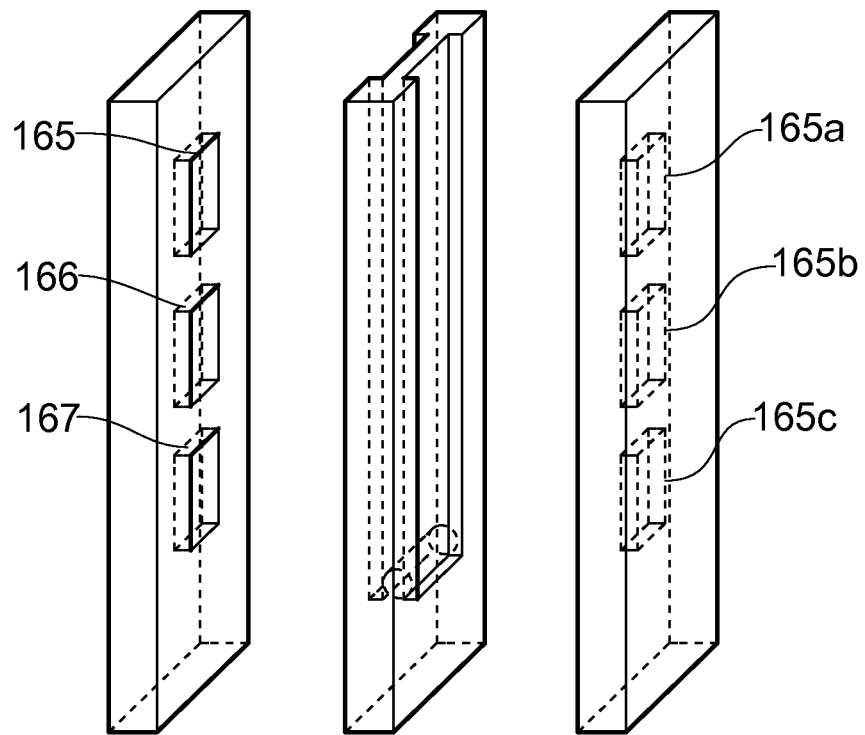
FIG. 15 is a diagrammatic perspective of a deposition assembly according to the invention.

Deposition devices, for example piezoelectric dispensers, may be provided in modular or non-modular form. As regards modular presentation of deposition devices, a number of options may be mentioned. As already described, the module 204 of FIG. 13 may be modified to replace the one or more detectors in it with one or more dispensing devices. In another modular variant, a treatment device 100 is modified to include one or more dispenser devices in one of the plates forming the device, typically an end plate 116,118. Optionally, one or more dispensing devices may be included in both end plates 116 and 118, as shown in FIG. 15, where the dispensing heads, e.g. piezoelectric dispensers, are indicated by reference numerals 165, 166, 167 and 165a, 165b and 165c. Advantageously, the or each dispensing device is coupled to a processor, for example a computer, which is programmed to control the dispensers for spatial addressing of the deposited materials. Thus, where there are multiple dispensing heads, each dispenser will in some embodiments deposit its reagent onto a spatially distinct area of the solid phase 1. This is useful for example in solid phase synthesis, where a different synthetic building block may be deposited from each of a plurality of different deposition heads. Thus, where a biological or other polymer (e.g. an organic semiconductor polymer) is being synthesised, each deposition head may deposit a different monomer or oligomer, for example a different amino acid or oligopeptide in the case of polypeptide synthesis, a different nucleotide or oligonucleotide in the case of nucleic acid synthesis and a different monosaccharide or oligosaccharide in the case of polysaccharide synthesis. In the case of solid phase synthesis, additional synthetic building blocks will be applied to the solid phase in preceding and/or succeeding steps to build up the completed molecule, e.g. completed polymer. Such additional steps may include deposition of a reagent from a deposition head, for example the deposition of multiple reagents in a further spatial addressing stage, or contacting the solid phase with a liquid phase as described herein, or a combination thereof.

In certain variants of FIG. 15, the apparatus is for contacting a mobile elongate solid phase with a flowing fluid phase and a plate may comprise one or more sensors for determining a parameter of the fluid phase contained in the apparatus instead of, or in addition to, one or more dispensing heads.

Also included in the disclosure are variants of FIG. 15 in which the apparatus is for contacting a mobile elongate solid phase with a flowing fluid phase and a plate may comprise one or more energy sources instead of, or in addition to, one or more dispensing heads and/or sensors.

The invention therefore also provides an apparatus for contacting a mobile elongate solid phase with a flowing fluid phase, comprising: a conduit which is of circular or non-circular transverse cross section and which defines a lumen to contain both the flowing fluid phase and the mobile elongate solid phase; fluid phase ports in communication with the lumen to allow the fluid phase to enter the lumen, flow through it and exit it; and solid phase ports in communication with the lumen to allow the mobile solid phase to enter the lumen, move through it and exit it, the conduit comprising: a sensor arranged to determine a parameter of a fluid phase contained in the lumen, an energy source arranged to expose the lumen to energy, or both. Further optional features of such apparatus may be as described elsewhere herein in relation to an apparatus for contacting a mobile elongate solid phase with a flowing fluid phase.

FIG. 15 and its variants are embodiments of an apparatus for performing a process involving a mobile elongate solid phase and defining (i) a conduit to contain the solid phase and optionally to contain also a flowing fluid phase in contact with the solid phase, and (ii) solid phase ports in communication with the interior of the conduit to allow the mobile solid phase to enter the conduit, move through it and exit it, the apparatus comprising three plates, each comprising two opposed faces, the plates being releasably interconnected in face-to-face relationship such that there is an intermediate plate between first and second end plates, the interconnected plates forming a unit having a first end and a second end, the intermediate plate having an aperture defined therein towards the second end of the unit to define a channel between its two faces, the aperture optionally having a roller rotatably arranged therein, and wherein: the first end plate and the intermediate plate define therebetween a first arm of the conduit; the second end plate and the intermediate plate define therebetween a second arm of the conduit; the first and second arms extend in a direction from the first end of the unit to the second end of the unit and each terminate at, and in fluid connection with, the aperture; and at least one of the plates comprises: a sensor arranged to determine a parameter of the solid phase; a sensor arranged to determine a parameter of the fluid phase; an energy source to expose the interior of the conduit to energy; and a deposition device for depositing a substance onto the solid phase. The unit may have fluid phase ports in communication with the interior of the conduit to allow the fluid phase to enter the conduit, flow through it and exit it. The first and second arms may each have a region towards the first end of the unit which region is in communication with the solid phase ports and the fluid phase ports, the solid phase port of each arm being spaced further towards the first end of the unit than the fluid phase port of the arm.

Figure 16:
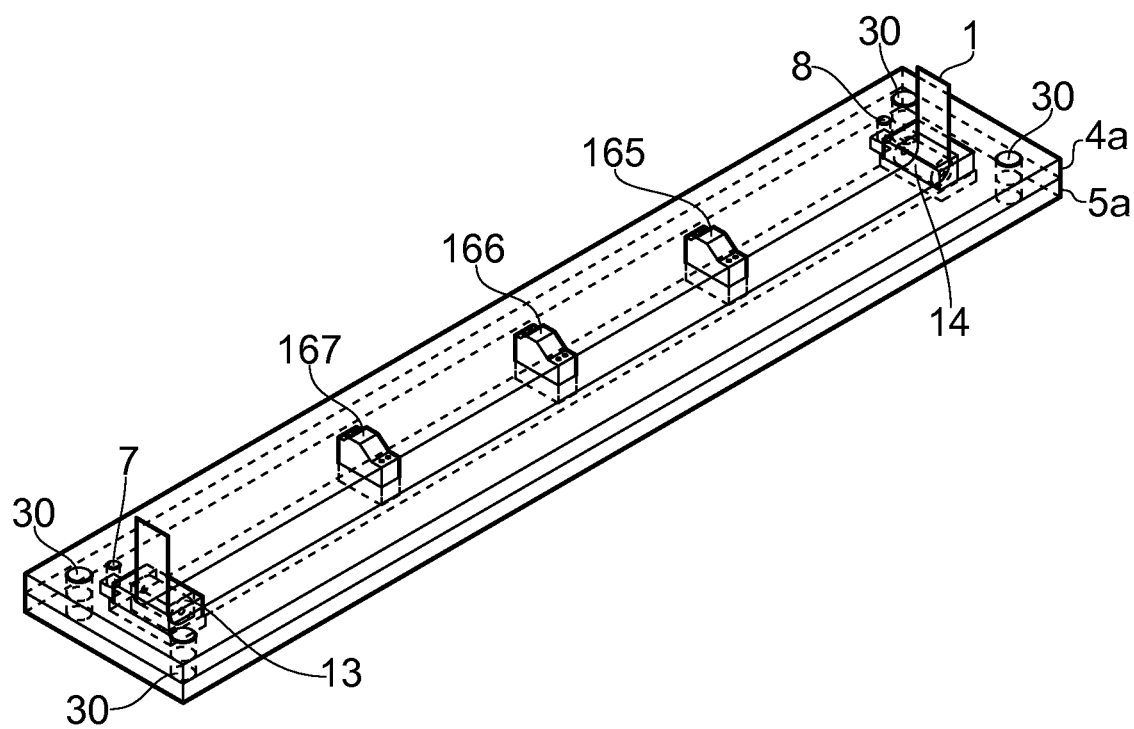
FIG. 16 is a perspective view of a second deposition assembly of the invention, comprising an upper plate and a lower plate.

An alternative modular deposition device is illustrated by FIG. 16, which comprises a variant of the apparatus of FIG. 1. Thus, the apparatus of FIG. 16 comprises a first or upper plate 4a in face-to-face engagement with a second or lower plate 5a. The two plates are connected together, e.g. releasably connected, for example by means of bolts accommodated in bolt holes 30.

Figure 17:
FIGS. 17 and 18 are side and, respectively, plan views of the upper plate of the deposition assembly of FIG. 16.
Figure 18:
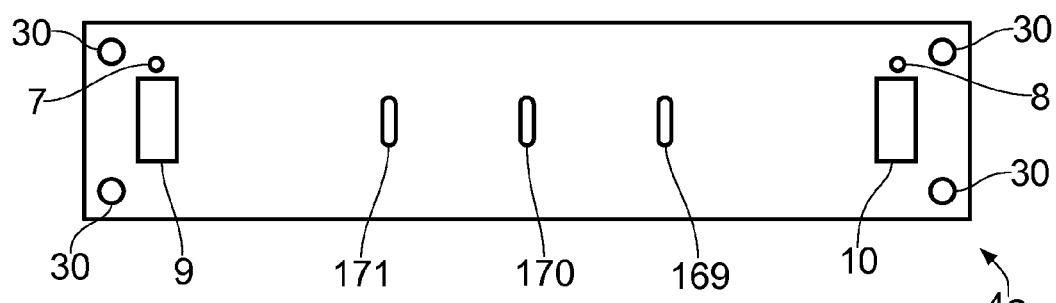

The structure of the first plate 4a is shown most clearly in FIGS. 17 and 18. It has defined therein solid phase ports 9 and 10 and, as will be explained later, optionally includes also liquid phase ports 7 and 8. Also defined in first plate 4a are one or more through holes in alignment with the solid phase pathway, to permit dispensers to be mounted above and/or in the through holes for dispensed reagents to contact the solid phase 1. In the illustrated embodiment, each of the three dispensing heads 165, 166, 167 is mounted above a respective through hole 169, 170, 171 as an alternative to each dispensing head being provided with an individual through hole, a common through hole or slot may be provided for all dispensing heads, in the case of an apparatus having plural dispensing heads.

Figure 19:
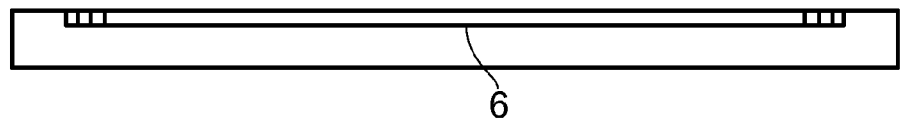
FIGS. 19 and 20 are side and, respectively, plan views of the lower plate of the deposition assembly of FIG. 16.
Figure 20:
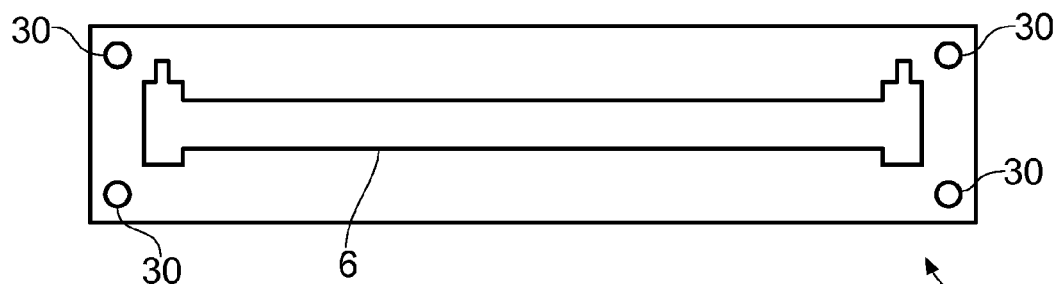

The second plate 5a may best be seen in FIGS. 19 and 20, where the second plate 5a can be seen to have defined therein a longitudinal channel 6, shown in the form of a hollow trough, to accommodate the solid phase 1.

As illustrated in FIG. 16, the deposition apparatus additionally includes rollers 13, 14 to guide the solid phase 1 into and out of the channel 6 via the solid phase ports 9 and 10. The rollers 13 and 14 may be accommodated in respective port channels 11 and 12 in communication with solid phase ports 9 and 10.

As previously mentioned, the apparatus of FIGS. 16-20 includes optional liquid phase ports 7 and 8. In this respect, the apparatus of FIGS. 16-20 may be adapted for use as apparatuses for contacting the mobile elongate solid phase 1 with a flowing liquid phase by removing the dispensing heads 165, 166, 167 and blocking through holes 169, 170, 171, for example by means of suitable plugs. The liquid phase ports 7 and 8 are in liquid communication with the channel 6 which, together with the first plate, forms a conduit defining a lumen to contain both a flowing liquid phase and the mobile elongate solid phase. The fluid phase ports 7 and 8 may therefore be connected to tubing (not shown) to supply a flowing liquid phase to the conduit and remove it from the conduit. Such an apparatus is similar to that of FIG. 1, in that it is not well adapted to prevent the liquid phase egressing the apparatus through the solid phase ports 9 and 10, and leakage of liquid phase through the solid phase ports is suitably prevented by removing the flowing liquid phase under suction.

Figure 21:
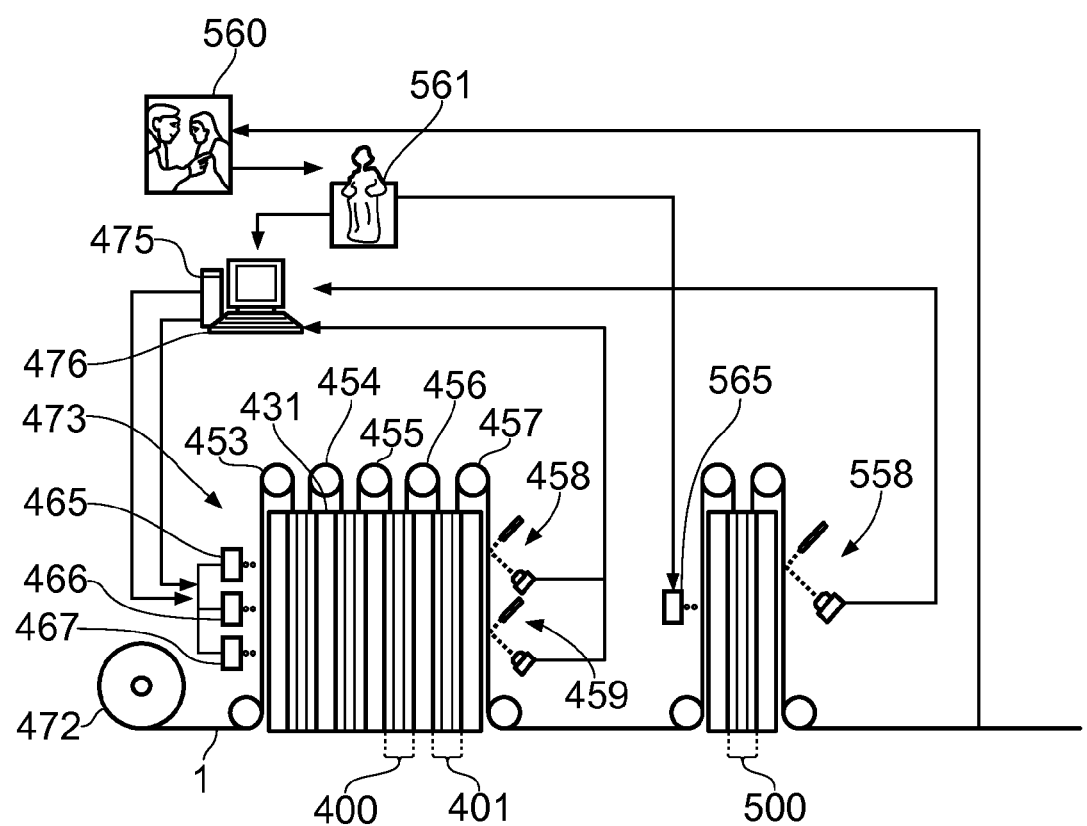
FIG. 21 is a schematic diagram of a system comprising apparatuses according to the second embodiment of the invention.

FIG. 21 is a diagrammatic illustration of a system comprising apparatus of the disclosure for contacting a mobile elongate solid phase with a flowing fluid phase. FIG. 21 is intended primarily to show different elements of a system, or a system section, of the disclosure and their interaction than to represent the specific apparatus of a practical system. Similarly to FIG. 13, one system of the disclosure illustrated by FIG. 21 comprises a plurality of phase contact devices, where the system is arranged for a solid phase pathway to be defined between successive phase contact devices such that the solid phase may move through the successive devices one after another, a first phase contact device for 100 and a second phase contact device for 101 being disposed in succession along the pathway and arranged to receive fluid from a common first fluid source, and a third phase contact device 500 along the pathway being arranged to receive fluid from a second fluid source. A fluid phase port of the first phase contact device 400 may be in fluid communication with a fluid phase port of the second phase contact device 401 to enable fluid to flow from the first phase contact device 400 to the second phase contact device 401; alternatively, the first 400 and second 401 phase contact devices may be arranged to receive fluid from the first fluid source in that both are arranged to communicate with the first fluid source via a flow path which does not include any said phase contact device. In this latter arrangement the first and second phase contact devices may be connected to a fluid source, for example a fluid reservoir, via tubing connected to a fluid phase port of the respective device which acts as a fluid inlet port.

The first 400 and second 401 phase contact devices may be releasably coupled together and, as shown in the illustrated embodiment, may be arranged in a stack of phase contact devices in which all the phase contact devices may be in, or capable of being put in, fluid communication with a common fluid source for all the phase contact devices of the stack. The stack may include a housing which accommodates the phase contact devices of the stack. For clarity, the housing is not shown in FIG. 21, suitable housing as being illustrated in FIGS. 7-9. The housing may be connected to rollers 453-457 arranged to guide the solid phase along the solid phase pathway outside the phase contact devices. As illustrated by FIGS. 7-9, at least one roller of the stack may be a drive roller in connection with a drive device for causing the roller to rotate and drive the solid phase 1.

The system illustrated in FIG. 21 further includes a deposition device arranged outside the successive phase contact modules, for depositing a reagent on the solid phase 401 as it moves along the pathway. In the case of FIG. 21, there are shown to be three deposition devices 165, 166 and 167, although it will be appreciated that in general terms there may be one deposition device or a plurality of deposition devices. Irrespective of the number of deposition devices, in some embodiments of the invention they are arranged in a modified treatment device as illustrated by, for example, FIG. 15 or FIG. 16, although this is not an essential feature of the invention.

The invention includes systems which comprise a deposition zone in which there are arranged a plurality of deposition devices, as in the case of the illustrated devices 465,466 and 467, for depositing reagents on the solid phase 1 in a spatially addressed manner.

The system illustrated by FIG. 21 is shown to include a sensor device arranged outside the successive phase contact modules for determining a parameter of the solid phase 1 as it moves along the pathway and, in the embodiment shown, two sensor devices 458 and 459 are illustrated as following the second phase contact device 401 along the solid phase pathway. It will therefore be seen that FIG. 21 illustrates a system having a solid phase pathway which has arranged along it in succession (i) a deposition device for depositing a reagent on the solid phase as it moves along the pathway; (ii) then a phase contact module; and (iii) then a sensor device for determining a parameter of the solid phase as it moves along the pathway. Considering now the system of FIG. 21 in more detail, it is shown to include a solid phase, particularly an elongate flexible web 1, for example a ribbon, moving along a solid phase pathway. The system includes a solid supply 472 which is shown as a reel in FIG. 21 but may alternatively be, for example, a cartridge or other container comprising ribbon or other solid phase freely folded in a compact, e.g. serpentine, arrangement. Such a container of folded solid phase advantageously permits the solid phase to be withdrawn from the solid phase supply 472 with application of a lesser force than might be required for withdrawal of the solid phase from a reel. The solid phase passes through a plurality of treatment stations, each for performing a respective stage of an overall process, for example a solid stage synthesis. In the illustrated embodiment, the first treatment station comprises a deposition zone containing one or more deposition devices, shown as deposition devices 465, 466, 467. Typically, the deposition devices are adapted to spatially address reagents onto the solid phase 1. For example, in the case of solid phase synthesis, each of the devices may spatially address a respective synthetic building block, whereby the deposition zone forms on the solid phase 1 an array of spatially distinct areas, each area being occupied by a different synthetic building block. At the end of the synthesis, there will therefore be formed on the solid phase an array of spatially distinct areas, each area occupied by end product molecules of a respective predetermined structure. For example, the solid phase synthesis may be a synthesis of a biological polymer, e.g. a polypeptide. In this case of spatially addressed deposition, each of a plurality of deposition devices in the deposition zone deposits a different amino acid, each to form the initial amino acid of the polypeptide to be grown from the initial amino acid.

After deposition of the first reagent, the solid phase is washed by passage through one or more treatment devices in which the solid phase is contacted, particularly in counter current, by a washing liquid. In the illustrated embodiment, the solid phase 1 passes through a stack 473 comprising a multiplicity of interconnected treatment devices, including the first and second treatment devices 400,401. Exemplary treatment devices are as illustrated by FIGS. 8 and 9. After passage through the stack 473, the solid phase is exposed to one or more sensors, illustrated as sensors 458,459 to determine the adequate completion of the first stage of synthesis. For example, one of synthesis 458 may be an ultraviolet spectrometer and the other of the sensors an infrared spectrometer, to enable the UV and IR spectra of the solid phase to be monitored to ensure that the amino acids or other synthetic building blocks previously deposited onto the solid phase have corrected coupled to the solid phase in their respective defined areas.

FIG. 21 is an abbreviated diagram and does not show the multiple treatment zones which would be required to complete a solid stage synthesis. Each treatment zone carries out a stage of the solid phase synthesis, so that overall the system performs the synthesis on the solid phase as it moves through the various treatment stages. A typical system for performing a solid phase synthesis may therefore comprise the following types of treatment zones:

1. A Pretreatment Zone.

A system may comprise at least one "pretreatment zone" for performing one or more initial pre-treatments before synthesis is commenced. A typical pretreatment serves to provide the solid phase with appropriate functional groups on which to start synthesis; as appropriate, spacers and/or linkers may be attached to the solid phase to facilitate attachment of synthetic building blocks. Unwanted functional groups may be capped to prevent reaction subsequently. In the case of a cotton or other cellulosic substrate, pretreatment may comprise an optional initial washing stage, followed by acid activation, attachment of a spacer, optional washing, capping, deprotection, optional washing and attachment of a linker, e.g. a Rink linker. Each of these stages will be carried out in a separate treatment zone and, in some embodiments each pretreatment comprises contacting the solid phase with a flowing fluid, for example using an apparatus of the disclosure. Each pretreatment zone typically comprises an apparatus of the invention for contacting a mobile solid phase with a mobile fluid phase. Each pretreatment zone may, independently of each other pretreatment zone, comprise a stack of devices as previously described.

A pretreatment zone may include an energy source as previously described.

2. A Synthesis Zone

A system for performing solid phase synthesis will comprise at least two synthesis zones in which the solid phase is contacted with synthetic building block, e.g. a monomer or oligomer of a biological polymer or a future part of another organic molecule. As monomers may be mentioned amino acids, nucleotides and monosaccharides. The synthetic building block is therefore contacted with the solid phase in a synthesis zone, and upon contacting the solid phase reacts with a reactive group to become bound to the substrate. A synthetic building block may be a first synthetic building block with which the solid phase is contacted, in which case it is coupled to the substrate either directly or via one or more intermediate moieties (e.g. a spacer and a linker). Alternatively, a synthetic building block may be a second or subsequent synthetic building block which reacts with a moiety already formed by one or more previous synthetic building blocks.

A synthetic building block may be contacted with the solid phase either via deposition from a deposition head or by contacting the solid phase with a flowing liquid phase, for example using an apparatus of the disclosure. In many embodiments for performing solid phase synthesis, at least one contacting stage comprises contacting the solid state with a flowing liquid phase, e.g. using an apparatus disclosed herein for contacting a mobile solid phase with a mobile fluid phase. A synthesis zone may comprise a stack of devices as previously described. In one class of embodiments, at least one stage involves deposition of a synthetic building block from a deposition head, for example in one stage a plurality of synthetic building blocks may be deposited into spatially distinct areas to provide an array of different molecules coupled to the substrate. The invention includes also systems comprising a synthesis zone that has a single deposition head, or plural deposition heads, for depositing a single synthetic building block. Some typical processes comprise (i) at least one synthetic stage in which a plurality of synthetic building blocks are spatially addressed onto the solid phase from deposition heads to form an array and (ii) at least one synthetic stage which a single synthetic building block is contacted with the solid phase, for example the entire area of an array may be contacted with the same synthetic building block; an example of such a process is one where an array of polypeptides is being synthesised and all the polypeptides have a common amino acid at one position in the sequence. Where a synthetic stage involves contacting the solid phase with a single synthetic building block (as opposed to contact with plural building blocks and form an array), the single synthetic building block may be deposited either from a deposition head or by contacting the solid phase with a flowing liquid phase, for example using an apparatus of the disclosure.

A synthesis zone may include an energy source as previously described, for example in order to accelerate the rate of the synthetic reaction.

3. A Washing Zone.

Frequently, a solid phase is washed after being contacted with a reagent, in order to remove unreacted reagent. Such washing steps may occur after addition of a synthetic building block, after contacting a solid phase with a ligand or analyte, or after contacting the solid phase with some other reagent, for example an agent to add or remove a protecting group or to activate a functional group. A washing zone contacts the solid phase with a flowing liquid phase, for example using an apparatus of the invention, e.g. a stack of treatment devices. The liquid phase (the washing liquid) may flow in the opposite direction to the direction of movement of the solid phase, i.e. the two phases may be in countercurrent. A washing zone may include an energy source as previously described, for example in order to increase solubility of an unwanted substance or accelerate its dissolution.

4. A Deprotection Zone

Solid phase synthesis may involve deprotection of a protected functional group of a moiety bound to the substrate prior to a synthesis step. Such deprotection is typically effected by contacting the solid phase with one or more reagents and, in such a case, a deprotection zone may contact the solid phase with a flowing fluid phase (usually a flowing liquid phase), for example using an apparatus of the invention, e.g. a stack of treatment devices. Deprotection may be effected or promoted by irradiation, for example with UV radiation; a deprotection zone may therefore include a UV or other radiation source arranged to expose the lumen to radiation. The fluid phase may flow in the opposite direction to the direction of movement of the solid phase, i.e. the two phases may be in countercurrent. A deprotection zone may include an energy source as previously described in order to accelerate the deprotection reaction. A solid phase pathway may comprise the following treatment zones in succession: a deprotection zone, a washing zone then a synthesis zone; in embodiments, the washing zone is dispensed with.

5. An Activation Zone

Solid phase synthesis may involve activation of a protected functional group of a moiety bound to the substrate prior to a synthesis step. Such activation is typically effected by contacting the solid phase with one or more reagents and, in such a case, an activation zone may contact the solid phase with a flowing fluid phase (usually a flowing liquid phase), for example using an apparatus of the invention, e.g. a stack of treatment devices. The fluid phase may flow in the opposite direction to the direction of movement of the solid phase, i.e. the two phases may be in countercurrent. An activation zone may include an energy source as previously described in order to accelerate the activation reaction. A solid phase pathway may comprise the following treatment zones in succession: an activation zone, a washing zone then a synthesis zone; in embodiments, the washing zone is dispensed with.

The above list of possible treatment zones is not exhaustive. For example, a synthesis system or synthesis section of a system may include a functional group transformation zone in which a functional group transformation is effected, for example by contacting the solid phase with one or more reagents using one or more deposition heads and/or an apparatus of the disclosure for contacting a mobile solid phase with a flowing fluid phase.

In addition to treatment zones, for example as mentioned above, a system for solid phase synthesis may comprise a sensor zone, as illustrated by sensors 458 and 459 in FIG. 21. One or more parameters of the solid phase are determined in a sensor zone. As desired, the solid phase may therefore be exposed to one or more sensors to determine at least one parameter of the solid phase. Parameters which are determined could include detection of, for example, one or more peaks of a UV or IR spectrum characteristic of a desired product or an undesired impurity. Additionally or alternatively for sensors to determine one or more parameters of the solid phase, a sensor zone may include one or more sensors arranged to determine one or more parameters of the fluid phase before or after its passage through a treatment zone.

The system illustrated by FIG. 21, therefore, includes a solid phase synthesis section, symbolised by the deposition zone comprising the one or more deposition heads 465, 466, 467, the treatment device stack 473 and the sensor zone comprising the one or more sensors 458, 459. In practice, a solid phase synthesis system or a solid phase section of a system, will include appropriate treatment zones to perform all the stages of a solid phase synthesis on a solid phase as it is moved through the system or section; it may also include one or more sensor zones. Typically, a sensor zone will be positioned downstream of a synthesis zone along a solid phase pathway; a washing zone may be positioned between the synthesis zone and the sensor zone. A system or system section may comprise a plurality of synthesis zones followed by respective sensor zones, or it may have a single sensor zone.

Downstream of the solid phase synthesis section in the direction of movement of the solid phase, FIG. 21 illustrates an assay section comprising a contact zone comprising for example a deposition head 565, a washing zone comprising the third phase contact device 500 and a sensor 558. In the contact zone the solid phase 1 is contacted with an agent which, when it contacts an analyte having a predetermined property, undergoes a process specific to such analyte to create a detectable response; accordingly, by further determining any detectable response, it can be determined if the solid phase 1 includes the analyte. The detectable response may be measured, if desired, to provide a quantitative aspect to the determination. The contact zone may comprise, for example, one or more deposition heads or one or more apparatuses of the disclosure for contacting a mobile solid phase with a flowing fluid phase.

The agent contacted with the solid phase in the assay section may comprise a binding partner for the analyte which binds to the analyte to form a conjugate. Conjugate formation is a detectable response in such an instance; in practice, the solid phase will often be washed to remove unbound binding partner before the detectable response is detected for. Thus, the conjugate may be detected by any suitable technique, for example by labelling the agent with a detectable label or by contacting the solid phase with a labelled detector binding partner, e.g. antibody, for the first-deposited binding partner. The agent may for example be a biological substance, e.g. biological molecule or receptor, or it may be a binding partner for a biological substance, e.g. an antibody to a physiologically active substance.

In other embodiments, the agent contacted with the solid phase in the assay section may comprise a substrate of the analyte which is acted on by the analyte to produce a detectable response. As examples may be enzyme substrates, for example chromogenic substrates.

In embodiments, the system is used to synthesise and screen compounds for useful biological activity, particularly for biological activity indicative of potential pharmaceutical use. The system may therefore be used to synthesise and screen potential drug candidates. For example, the agent contacted with the solid phase may comprise a drug target, for example an enzyme, a part of an enzyme, a receptor or a part of a receptor. The assay advantageously measures the strength of the interaction between one or more analytes which have been synthesised on the solid phase and the agent.

A typical system, or system section, for performing an assay may therefore comprise the following types of zones:

A. A Contact Zone.

A system may comprise at least one contact zone for contacting the solid phase with an assay agent, namely an agent which, when it contacts an analyte having a predetermined property, undergoes a process specific to such analyte to create a detectable response. A contact zone may comprise a deposition head, e.g. a plurality of deposition heads. A contact zone may comprise an apparatus of the disclosure for contacting a mobile solid phase with a flowing liquid phase, or it may comprise a plurality of such apparatuses. A contact zone may comprise a stack as herein described of devices for contacting a mobile solid phase with a flowing liquid phase.

A contact zone may include an energy source as previously described.

B. A Washing Zone.

A solid phase may be washed after being contacted with an assay agent, in order to remove agent which has not bound to the solid phase. Such washing is required where the assay uses the presence of the assay agent bound to the solid phase as an indicator of conjugate formation. A washing zone contacts the solid phase with a flowing liquid phase, for example using an apparatus of the invention, e.g. a stack of treatment devices. The liquid phase (the washing liquid) may flow in the opposite direction to the direction of movement of the solid phase, i.e. the two phases may be in countercurrent. A washing zone may include an energy source as previously described, for example in order to increase solubility of an unwanted substance or accelerate its dissolution.

C. A Detection Zone

After the solid phase has been contacted with an assay agent, and after any necessary or desired washing stage, the solid phase may move to a detection zone comprising a sensor, e.g. a plurality of sensors, to detect and/or measure the detectable response. For example, if the detectable response is conjugate formation and it is detected by binding of a labelled agent to any analyte which has been synthesised on the solid phase, the sensor will detect and/or measure the label.

The above list of possible zones in an assay system is not exhaustive.

It will be appreciated that, whilst FIG. 21 illustrates the assay section as downstream of a synthesis section, this arrangement is not necessary. For example, preformed analytes may be attached to a solid phase and then analysed using a mobile solid phase analysis system of the disclosure. A mobile solid phase analysis system therefore forms an aspect of the invention, whether as a system in its own right or as a subsystem of a larger system.

After synthesis or after assaying, a solid phase may be passed through a cleaving zone for cleaving attached molecules from the solid phase. Suitably, the cleaving is performed using a flowing liquid phase and/or an apparatus of the disclosure for contacting a mobile solid phase with a flowing fluid phase. Amongst other alternatives, the solid phase may be cut into sections and attached molecules may be removed by batch processing. A cleaving zone may be followed by an assay zone for determining the completeness of the cleavage process.

Identifiers

A system of the invention may include a device for applying one or more identifying indicia to the solid phase. In particular, an identifying index may be applied in association with each spatially distinct area of an array. Such an index may comprise any readable identifier, for example a barcode or a combination of semiconductor nanocrystals. The index may be applied directly, for example by printing, or indirectly, for example by application of a label. A system may further comprise one or more readers for such identifiers, for example a bar code scanner, to enable each area of an array to be identified. Such a system of identifiers and identifier readers may be useful to enable a predetermined area of an array to be identified for deposition thereon of a reagent from a deposition head. Additionally or alternatively, such a system of identifiers and identifier readers may be useful to enable a predetermined area of an array to be identified in connection with determination of a detectable response during performance of an assay; identification of the area will enable the substance contained in that area to be identified. A printer or other device for applying identifiers may be before, within or after a deposition zone; where a device for applying identifiers is positioned before a deposition zone along a solid phase pathway, the applied identifiers may be used to identify areas for deposition of one or more reagents within the subsequent deposition zone.

Non-spatial identifiers are used in some processes. For example, variable synthetic building blocks (i.e. those building blocks which may differ between different molecules of an array) may be labelled with identifiers, each identifier being specific for a predetermined building block (e.g. a predetermined amino acid, nucleotide or monosaccharide). A synthesised substance may be identified by identifying the identifiers of its variable building blocks.

Automation and Feedback

One or more elements of a system of the disclosure may in use be in signal communication with a computer or processor, as indicated at 475 in FIG. 20. The computer may include an operator interface, shown at 476 in FIG. 20 as a computer screen and keyboard. In some embodiments, the computer may display one or more measured parameters of the system to allow an operator to change one or more operating conditions through the operator interface. Additionally or alternatively, a computer may be programmed to change one or more operating conditions responsive to one or more measured parameters of the system.

Design of experiment methods are known in the art as a technique aimed at maximal information output (Maier W F et al, *Angew. Chem., Inst. Ed.,* 2007, 46: 6016-6067; Cawse J N, *Experimental Design for Combinatorial and High Throughput Materials Development*; Wiley InterScience: New York, 2003). Originally developed for drug discovery applications (Appell K et al, *Combinatorial Chemistry and High-Throughput Screening in Drug Discovery and Development.* In *Handbook of Modern Pharmaceutical Analysis*; Ahuja S and Scypinskis, Eds; *Separation Science and Technology*: San Diego, Calif., 2001; pp 23-56), these techniques have since been supplied to an ever increasing number of materials. An automation and feedback system of embodiments of the disclosure may be used in such design of experiment methods, in particular in the application of a genetic algorithm.

Similar to the principles of evolution and natural selection found in nature, genetic algorithms will iteratively generate successive generations of operating conditions by applying evolutionary operators, such as mutation and cross-over, in a fitness-proportional and self-adapted manner, in such a way that the created populations undergo a steady evolution so as to approach an optimal solution for the optimization problem ((a) Holena. Present Trends in the Application of Genetic Algorithms to Heterogeneous Catalysis. M. In *High-Throughput Screening in Chemical Catalysis*; Hagemeyer, A, Strasser, P, Volpe A P, Eds.; Wiley-VCH: Weinheim, Germany, 2004; pp. 153-174. (b) Cawse, J N *Acc. Chem. Res.* 2001, 34, 213-221. (c) Goldberg, D E *Genetic Algorithms in Search, Optimization and Machine Learning*; Addison-Wesley: Reading, Mass., 1989. (d) Holland J H, *Adaptation in Natural and Artificial Systems*, The University Press of Michigan: Ann Arbor, Mich., 1975.). Contrary to other design of experiment strategies, genetic algorithms allow the use of continuously variable parameters. They are furthermore not limited by the boundaries of the starting library and can thus escape local optima and enter new regions of the parameter space by themselves (see Maier W F et al, above). All the aforegoing publications relating to design of experiment methods and genetic algorithms are included herein by reference in their entirety for all purposes.

Operating conditions that may be subjected to automated feedback and control, e.g. a genetic algorithm, include: speed of solid state; interruptions in movement of solid state; speed of fluid state; interruptions in movement of solid state; composition of fluid state; operation of energy sources (on/off state and rate of energy production); and selection of deposited substances. This list is not exhaustive.

For the sake of clarity, FIG. 21 illustrates only a minority of possible processor interconnections. A somewhat more comprehensive illustration can be found in FIG. 22.

FIG. 22 illustrates a system of the invention comprising a solid phase synthesis section 680 and an assay section 681. An elongate solid phase 1, for example a ribbon or elongate flexible web, is moved through the system from a solid phase supply 672, for example a container containing freely folded solid phase or a reel. Each section of the system comprises the following zones in the illustrated embodiment:

The Synthesis Section 680:
a pretreatment zone 682
a synthesis zone 683
a washing zone 684
a deprotection zone 685
a washing zone 686
a synthesis zone 687
a washing zone 688
a sensor zone 689.
The Assay Section 681:
a contact zone 690
a washing zone 691
a detection zone 692.

It will be understood that the system of FIG. 22 is merely an example and that many variations in the number, type and/or order of zones and sections are possible.

Each zone except the sensor zone 689 and the detection zone 692 is included in a fluidic system and is in communication with a fluid supply and a fluid outlet. In FIG. 22, the fluid supply and fluid outlet for each zone is indicated by the reference numeral for the zone followed by the suffix "s" for the fluid supply and the suffix "o" for the fluid outlet, e.g. the fluid supply for the pretreatment zone 682 is designated 682$s$ and the fluid outlet for the pretreatment zone 682 is designated 682$o$. In the illustrated embodiment, therefore, each zone of the system comprises an apparatus of the disclosure for contacting a mobile solid phase with a flowing fluid phase. Such apparatus may be arranged in one or more stacks as previously described, although this is not a mandatory feature of the invention. Sometimes, a zone may include a device other than a said apparatus, for example it may include one or more deposition devices.

Each fluid source 682$s$-691$s$ comprises a controllable fluid metering device for providing a controlled fluid phase flow to the treatment apparatus or apparatuses comprised within the zone concerned. The controllable fluid metering device may comprise a controllable pump or a controllable valve, or both. A fluid source may comprise a fluid reservoir and a valve to control fluid flow from the fluid reservoir and/or a pump to pump fluid from the reservoir. FIG. 23 illustrates the structure of fluid source 685; the fluid source is shown to comprise a plurality of fluid reservoirs 693, 694, 695 each containing a fluid the same as or different from the fluid contained in the others and in communication with the pretreatment zone 682 through a line containing a respective valve 693,694 or 695. One reservoir may contain a solvent and the other(s) may contain a reagent or another solvent, but this is just one option amongst others. In any embodiment of the invention, therefore, fluid source may comprise a single fluid reservoir or a solid for mixing with a fluid, a mixer may be provided for mixing the solid with the fluid before the fluid is supplied to the treatment zone with which the fluid source is in communication.

Each outlet may, independently of each other outlet, be to a drain or, advantageously, the outlet fluid is where possible treated and recycled.

The system includes one or more drive devices for moving the elongate solid phase 1 through the system. The drive devices conveniently comprise a drive motor coupled to a drive roller. In the illustrated embodiment, each zone includes a drive roller coupled to a motor designated by the suffix "m", e.g. the drive motor for driving the solid phase through the pretreatment zone 682 is designated 682$m$. The drive motors are advantageously controllable, for example may be stepper motors.

The synthesis zone 683, the deprotection zone 685 and the synthesis zone 687 include an energy source as previously described. For ease of illustration, the energy sources are shown as outside but coupled to the respective zones as indicated at 683$e$, 685$e$ and 687$e$. It will be appreciated that energy sources may be incorporated in treatment zones as previously described or may be located outside treatment zones but that FIG. 22 is intended to provide a diagrammatic illustration of energy sources incorporated in treatment zones.

As previously mentioned, a system of the disclosure may contain a cleavage zone for cleaving molecules from the solid phase, optionally followed by an assay zone for checking completeness of the cleavage.

The system further comprises a processor 675 in communication with a processor interface 676. The processor may comprise a computer and the processor interface may comprise a keyboard and a video display screen. As indicated by the dotted lines in FIG. 22, the system comprises a communication pathway connecting the processor 675 with sensing elements of the system and controllable elements of the system. Controllable elements of the system in this case comprise: each fluid source and in particular a fluid metering device comprised in each fluid source, each motor, and each energy source. The sensor elements of the system of FIG. 22 comprise the sensors of the sensor zone 689 and of the detection zone 692. The controllable elements of the system are therefore in signal communication with the processor, or at least adapted to be in signal communication with the processor when the system is working. Where there is a cleaving zone, controllable elements associated with it as well as sensing elements of any subsequent assay zone are in signal communication with the processor, or at least adapted to be in signal communication with the processor when the system is working. The processor is programmed to control the controllable elements responsive to one or more parameters determined by the sensor elements. The processor may be programmed to control each controllable element responsive to one or more selected parameters independently of each other controllable element, or control of at least one controllable element may be dependent on or associated with control of at least one other controllable element. For example, the computer (processor) may be adapted to improve washing responsive to an unacceptable purity level being detected by a sensor; washing may be improved by, for example, increasing the liquid flow rate, decreasing the solid phase movement rate, or up-regulating an energy source of a washing zone. In embodiments, washing may be improved by modifying the washing liquid passing through a washing zone, for example the washing liquid may comprise a mixture of liquids and the relative proportions of the individual liquids may be changed. Any one or a combination of these measures may be adopted to improve washing.

The processor may be adapted to change the conditions of a reaction zone where a parameter detected by a sensor indicates that a reaction has not been driven sufficiently to completion, for example a sensor may detect the presence of a functional group which was present on the solid phase when it entered the reaction zone but should not have been present when the solid phase left the reaction zone, or an unacceptable amount of such a functional group. In such a case, the reaction zone may be an activation zone, a protection zone, a deprotection zone, a functional group transformation zone or a synthesis zone, for example. The computer may be adapted to (programmed to) alter the process conditions to drive the reaction further to completion by, for example, up-regulating an energy source, increasing the rate of liquid flow, increasing reagent concentration or changing another characteristic of the liquid (e.g. pH), or slowing the rate of movement of the solid phase.

A processor may be adapted to respond to parameters determined in a detection zone of an assay section by changing the washing conditions to improve washing, in the case that the parameter is indicative of the presence of an unwanted substance.

In embodiments, the invention uses an assay system (e.g. assay subsystem) in the screening of molecules, for example in biological screening for pharmaceutical or other purposes. In such a case, the assay system may comprise a contact zone where the solid phase is contacted with a test substance. In some embodiments, the contact zone may comprise a deposition device. In particular embodiments, the contact zone comprises an apparatus of the disclosure for contacting the solid phase with a flowing fluid. Whatever the structure of the contact zone it may comprise a plurality of test substances and be adapted to select one or more test substances for contacting with the solid phase. The processor may be adapted to change the selection of test substance(s). For example, the computer may be adapted to change test substance responsive to a parameter determined by a detection zone of the assay system and indicative of a level of interaction between the substance attached to the solid phase and the test substance falling below a threshold.

The invention includes embodiments in which the system contains a synthesis section 680 followed by an assay section 681, as diagrammatically illustrated in FIGS. 21, 22. In such a case, the processor 475, 675 may be adapted to change the substance being synthesised responsive to a parameter determined by the assay section. For example, the solid phase may have synthesised on it an array of compounds. The assay zone is adapted to measure a parameter indicative of an interaction between the synthesised compounds and a test substance contacted with the solid phase. The parameter may indicate, for example, affinity between the compounds and the test substance, an inhibitory effect of the compounds on the test substance or the susceptibility of the compounds to an enzymatic activity of the test substance. The processor is adapted to (programmed to) identify compounds of the array having a predetermined parameter. The predetermined parameter may, for example, be a parameter falling at or above a threshold value or it may be a highest value measured by the detection zone. The compounds which gave rise to the predetermined parameter may be identified by an identifier provided in the solid phase and identified by a reader comprised in the assay section. The processor 475, 675 may be adapted to change the structure of the synthesis compounds synthesised in the synthesis section responsive to the predetermined parameter.

In one example, the compounds being synthesised on the solid phase are biological polymers, for example polypeptides. The biological polymers are optionally labeled. The solid phase therefore has an array of biological polymers formed on it, the array comprising spatially distinct areas, each area being occupied by biological polymers of a respective predetermined sequence. The solid phase is then moved through a treatment station (e.g. a contact zone 690) where it is contacted with an agent which, when it contacts an analyte (i.e. biological polymer in this case) having a predetermined property, undergoes a process specific to such analyte to create a measurable response. The measureable response may comprise, for example, fluorescence or another measurable characteristic of a label comprised in the agent or it may be a visible label created as a result of an action of the analyte on the biological polymers. In any event, the amount of the measurable response of each spatially distinct area is measured whereby a polymer structure resulting in a predetermined measurable response may be identified. The processor may be adapted to take those identified structures and instruct the synthetic section of the system to change the structures of the polymers (e.g. to change one or more of the synthetic building blocks used in the synthesis of the polymers) to create an array of polymers representing defined modifications of the polymers identified as possessing the predetermined measurable response.

In other embodiments, the molecules synthesised on the solid phase are small organic molecules comprising a cyclic moiety having a substituent. A cyclic structure or structures having a predetermined measurable response are identified and the processor is adapted to change the instructions to the synthetic section of the system to change the substituents on the cyclic structure which it synthesises (e.g. add substituents, remove substituents or change substituents).

Included are embodiments in which the compound synthesised on the solid phase are small organic molecules having a functional group. The processor may be adapted to instruct the synthesis section to react the functional group of a molecule identified as having a predetermined response in order to form a plurality of different structures.

As described above, therefore, a system may be adapted to screen an array of compounds to identify those having a desired property, for example an affinity or a biological activity falling at or above a predetermined threshold. The library of molecules may then be expanded around those identified structures, and the expanded library may then be further screened to determine any additional compounds which have an enhanced property.

There is therefore disclosed a method which comprises synthesising a first library of compounds, identifying members of the first library having a predetermined property, generating structures of a second library of compounds by varying the structures of the identified compounds, and synthesising the second library of compounds. Such methods form an aspect of the invention. The predetermined property may be a binding activity, an inhibitory activity, an agonist activity, an antagonist activity or a substrate activity (i.e. an ability to act as a substrate). The predetermined property may be possession of such an activity at or above a threshold. The predetermined activity may be possession of the highest such activity possessed by the members of the first library. The libraries, or either one of them, may be synthesized by continuous synthesis on a mobile elongate solid phase; the synthesis process and/or apparatus may be, but is not required to be, as disclosed herein. The libraries, or either one of them, may be assayed for the predetermined property on a mobile elongate solid phase; the assay process and/or apparatus may be, but is not required to be, as disclosed herein.

The technology described with reference to FIGS. 21 and 22 includes a process for synthesising and screening molecules, comprising: moving an elongate solid phase through sequential treatment stations, each for performing a respective stage of a solid phase synthesis, at least one of the treatment stations being adapted to spatially address synthetic building blocks onto the solid phase, whereby to form on the solid phase at the end of the synthesis an array of spatially distinct areas, each area occupied by end product molecules of a respective predetermined structure; moving the solid phase on which the array is formed through a treatment station where it is contacted with an agent which, when it contacts an analyte having a predetermined property, undergoes a process specific to such analyte to create a measurable response; measuring the amount of the measurable response of each spatially distinct area; and identifying an end product molecule structure resulting in a predetermined measurable response. The predetermined measurable response may be a response at or above a specified threshold or it may be a highest response of the responses of all the spatially distinct areas. The process may further comprise the steps of: repeating the process to synthesise modifications of the structure resulting in a predetermined measurable response, each modification occupying a said spatially distinct area; and measuring the amount of the measurable response of the spatially distinct areas occupied by the modifications. Optionally, a computer programmed to identify the end product molecule structure resulting in the predetermined measurable response and to change at least one synthetic stage of the solid phase synthesis responsive to the identified structure causes the process to be repeated with a change of synthetic building block in at least one synthetic stage.

In some embodiments, the end product molecules are biologically active, for example comprise a polymer selected from a polysaccharide, a polypeptide and a polynucleotide, and the modification comprises changing the monomer sequence of the polymer. In other embodiments, the end product molecules comprise small organic molecules and the modification comprises changing the structure of at least one part of the molecule. For example, the end product molecules may comprise small organic molecules and the structure resulting in a predetermined detectable response comprises a cyclic moiety having at least one substituent and the modification comprises changing the structure of the substituent; in this way, the end product molecules may comprise a library of molecules each having a different cyclic moiety and one or more cyclic moieties having a predetermined detectable response indicative of a useful activity may be identified, and the substituent pattern of the cyclic moieties may then be varied to further optimise the molecular structure for the useful activity.

In other embodiments, the end product molecules comprise small organic molecules and the structure resulting in a predetermined detectable response comprises at least one functional group, and the modification comprises reacting the functional group to form a plurality of different structures; in this way, the end product molecules may comprise a library of molecules each having a different skeleton or scaffold moiety and one or more skeleton moieties having a predetermined detectable response indicative of a useful activity may be identified, and the one or more moieties may then be modified by derivatisation at one or more functional groups to further optimise the molecular structure for the useful activity.

In some processes, said agent comprises a labelled binding member and the measuring comprises washing the solid phase and then measuring a parameter indicative of the amount of label bound to the solid phase through the end product molecules; or said agent comprises an enzyme and an enzyme substrate, the enzyme substrate having a measurable parameter which is changed by the activity of the enzyme on the substrate, and the measuring comprising measuring said measurable parameter. The enzyme substrate may be chromogenic or fluorogenic, for example. The contacting with the agent may comprise sequentially contacting the solid phase with the enzyme and then the enzyme substrate.

Also illustrated by FIGS. 21 and 22 is an apparatus for use in synthesising and screening molecules, the apparatus providing a pathway along which an elongate solid phase may move and comprising disposed along the pathway in a direction from upstream to downstream: sequential treatment stations, each for performing a respective stage of a solid phase synthesis, at least one of the treatment stations comprising plural deposition devices for spatially addressed deposition of synthetic building blocks onto the solid phase; a treatment station for contacting the solid phase with an agent which, when it contacts an analyte having a predetermined property, undergoes a process specific to such analyte to create a measurable response; and a measuring station for measuring the amount of the measurable response of each spatially distinct area, the apparatus further comprising a computer which is adapted to be in signal communication with, or which is in signal communication with, the measuring station and programmed to identify the predetermined measurable response and to determine the corresponding end product molecule structure from data available to the computer.

Further illustrated by FIGS. 21 and 22 is an apparatus for use in synthesising and screening molecules, the apparatus providing a pathway for an elongate solid phase to move along, the apparatus comprising disposed along the pathway in a downstream direction: sequential treatment stations, each for performing a respective stage of a solid phase synthesis, at least one of the treatment stations comprising plural deposition devices for spatially addressed deposition of synthetic building blocks onto the solid phase and at least one of the treatment stations comprising the apparatus of the disclosure; treatment station for contacting the solid phase with an agent which, when it contacts an analyte having a predetermined property, undergoes a process specific to such analyte to create a measurable response; and a measuring station for measuring the amount of the measurable response of each spatially distinct area.

Reverting to FIG. 21, this diagrammatically illustrates the application of the invention to personalised medicine. Reference numeral 560 indicates a consultation between a patient and a medical practitioner. A sample is taken from the patient and a scientist indicated at 561 provides to the deposition head 565 a substance derived from the sample which is associated with the patient's disease. The substance may be a mutant cell receptor associated with a cancer, for example. The system is then operated to synthesise compounds and screen them for a specified interaction with the substance, for example binding affinity with it. An initial library is therefore prepared and screened, from which selected compounds having performance at a certain level are identified. The initial library is expanded around those selected compounds, to create a second library of compounds whose structures represent modification of the selected compounds. The expansion may be controlled entirely by the computer 475 using an appropriate algorithm with which it is programmed or it may involve at least partial human input as indicated by the dotted line in FIG. 21. The second library is screened to identify any compounds having enhanced performance and, as desired the procedure may be repeated one or more times to create third and optionally subsequent libraries until one or more compounds are identified as having properties satisfactory for use in treating the patient. Conceptually speaking, such compounds may be considered as derived from the system downstream of the sensor 558 and transferred to the medical practitioner for use in treating the patient in a further consultation 560.

To conclude in relation to FIGS. 21 and 22, they illustrate a system for carrying out a heterogeneous process, comprising: a treatment apparatus configured to contain a flowing fluid phase and a longitudinally moving elongate solid phase in mutual contact; a controllable drive device for moving the solid phase through the treatment apparatus; a controllable fluid metering device (a pump or a valve, or a combination thereof) for providing a controlled fluid phase flow to the treatment apparatus; a sensor arranged to detect a parameter of the solid phase after the solid phase has passed through the treatment apparatus; a processor adapted to be in signal communication with the sensor and with at least one of the drive device and the fluid metering device to receive an input signal from the sensor and send an output signal to the at least one of the drive device and the fluid metering device, the processor being programmed to control the at least one of the drive device and the fluid metering device responsive to the detected parameter. As already mentioned, the system may comprise a sensor arranged to detect a parameter of the fluid phase after the fluid phase has passed through the treatment apparatus, additionally or alternatively to the sensor arranged to detect a parameter of the solid phase; in such a case the processor is adapted to be in signal communication with the sensor to receive an input signal from the sensor and send an output signal to the at least one of the drive device and the fluid metering device.

The system may further comprises a controllable energy source (e.g. a heat source, an ultrasound transducer or a magnetron, laser, light emitting diode, mercury vapour lamp (UV source), or other source of electromagnetic radiation) which is arranged for energy to be supplied from the source at least to the fluid phase and the solid phase where they are in mutual contact, and which is in signal communication with the processor, the processor being programmed to control the energy source responsive to the detected parameter.

Scale Up

Apparatus of the invention may be scaled up for bulk or semi-bulk synthesis by providing plural, particularly multiple, synthesis systems performing the same synthesis. In other words, a plurality of identical synthesis systems may be provided in parallel.

Further Embodiments

Embodiments of the invention are described in the following clauses 1 to 83:

1. An apparatus for contacting a mobile elongate solid phase with a flowing fluid phase, comprising:
a conduit which is of circular or non-circular transverse cross section and which defines a lumen to contain both the flowing fluid phase and the mobile elongate solid phase;
fluid phase ports in communication with the lumen to allow the fluid phase to enter the lumen, flow through it and exit it; and
solid phase ports in communication with the lumen to allow the mobile solid phase to enter the lumen, move through it and exit it.

2. An apparatus of clause 1 which is adapted to prevent fluid egress from its interior through the solid phase ports.

3. An apparatus of clause 1 or clause 2 wherein the fluid phase is a liquid phase.

4. An apparatus of clause 3 which is adapted such that, when the apparatus is in an upright orientation, the solid phase ports are spaced above the fluid phase ports, whereby in use the liquid phase does not contact the solid phase ports.

5. An apparatus of any preceding clause wherein the conduit comprises a region in which the conduit undergoes a change in direction.

6. The apparatus of clause 5 wherein the conduit comprises two arms which are interconnected by said region, the apparatus being configured for the two arms to be upright and in fluid interconnection at lower ends thereof when the apparatus is in use.

7. An apparatus of clause 5 or clause 6 wherein the region comprises a roller whose axis of rotation is transverse to the direction of movement of the solid phase and which is arranged for the solid phase to run over a portion of its circumference as the solid phase changes direction.

8. An apparatus of any preceding clause, wherein the conduit is defined by a plurality of releasably interconnected plates, the plates comprising a pair of plates in opposed face-to-face relationship and the opposed faces having defined between them a length of the conduit extending in a direction parallel with the pair of plates.

9. An apparatus of clause 7 which is further as defined in clause 5 and which comprises three plates, each having two opposed faces, the plates being releasably interconnected in face-to-face relationship such that there is an intermediate plate between first and second end plates, the interconnected plates forming a unit having an upper end which is disposed to the top of the unit when the unit is in use and a lower end which is disposed to the bottom of the unit when the unit is in use, the intermediate plate having an aperture defined therein towards the lower end of the unit to define a channel between its two faces, the aperture having the roller rotatably arranged therein, and wherein:
the first end plate and the intermediate plate define therebetween a first arm of the conduit;
the second end plate and the intermediate plate define therebetween a second arm of the conduit;
the first and second arms extend in a direction from the top of the unit to the bottom of the unit and each terminate at, and in fluid connection with, the aperture; and
the first and second arms each have an upper region in communication with the solid phase ports and the fluid phase ports, the solid phase port of each arm being spaced upwardly from the fluid phase port of the arm.

10. An apparatus of clause 9 wherein the first and second arms extend to the upper end of the unit at which upwardly facing open ends of the arms define the solid phase ports.

11. An apparatus of clause 9 or clause 10 wherein each of the opposed faces of the intermediate plate provides a channel which is open in a direction facing the respective end plate facing that face of the intermediate plate, the first and second arms being defined by said channels and their respective end plates.

12. An apparatus of any of clauses 8 to 11 which is a first said apparatus and is in combination with a second said apparatus, and wherein a said plate of the first said apparatus is shared by the second said apparatus.

13. An apparatus of any preceding clause which further comprises a roller arranged to guide the solid phase before it enters or, as the case may be, after it exits a said solid phase port.

14. An apparatus of any preceding clause wherein an energy source is arranged to expose at least part of the lumen to energy, optionally wherein the energy source comprises an ultrasound transducer or a magnetron, laser, light emitting diode, mercury vapour lamp (UV source), or other source of electromagnetic radiation.

15. An apparatus of any preceding clause which further comprises outside the conduit a deposition device arranged for depositing a reagent on the solid phase, for example for spatially addressed depositing of a reagent on the solid phase.

16. An apparatus of any preceding clause which further comprises:
a controllable drive device for moving the solid phase through the conduit; and
a fluid metering device for providing a fluid phase flow to the conduit.

17. An apparatus of any of clauses 1 to 13 which further comprises:

a sensor disposed outside the conduit to determine a parameter of the solid phase after the solid phase has passed through the conduit;

a processor adapted to be in communication with the sensor; and at least one controllable device adapted to be in communication with the processor and selected from an energy source arranged to expose at least part of the lumen to energy, a drive device for moving the solid phase through the conduit, a fluid metering device for providing a fluid phase flow to the conduit, and a heater arranged to heat the fluid phase, the processor being adapted to control the at least one controllable device responsive to the determined parameter.

18. An apparatus of clause 13 which is a first said apparatus and which is in combination with a second said apparatus to provide a pathway along which the elongate solid phase moves out of a solid phase port of the first apparatus and into a solid phase port of the second apparatus via the roller.

19. An apparatus of clause 18 wherein a fluid phase port of the first said apparatus is in fluid communication with a fluid phase port of the second said apparatus.

20. An apparatus of clause 18 wherein the first said apparatus and the second said apparatus are not in fluid communication with each other.

21. An apparatus of clause 20 which further comprises a third said apparatus and wherein a fluid phase port of the third said apparatus is in fluid communication with a fluid phase port of the second said apparatus.

22. An apparatus of any of clauses 18 to 21 wherein at least one of the first said apparatus, the second said apparatus and the third said apparatus is as defined in any one or a permitted combination of clauses 14 to 17.

23. A system for subjecting a longitudinally mobile elongate solid phase to a plurality of successive treatments, comprising a plurality of phase contact devices for contacting the mobile elongate solid phase with a flowing fluid phase, each phase contact device comprising (i) a conduit which is circular or non-circular in transverse cross-section and defines a lumen to contain both the flowing fluid phase and the mobile elongate solid phase, (ii) fluid phase ports in communication with the lumen to allow the fluid phase to enter the lumen, flow through it and exit it, and (iii) solid phase ports in communication with the lumen to allow the mobile solid phase to enter the lumen, move through it and exit it, the phase contact device optionally being adapted to prevent fluid egress from its interior through the solid phase ports; wherein:

the system is arranged for a solid phase pathway to be defined between successive phase contact devices such that the solid phase may move through the successive phase contact devices one after another;

a first phase contact device and a second phase contact device are disposed in succession along the pathway and are arranged to receive fluid from a common first fluid source;

a third phase contact device along the pathway is arranged to receive fluid from a second fluid source.

24. A system of clause 23 wherein the first and second phase contact devices are arranged to receive fluid from the first fluid source in that a fluid phase port of the first phase contact device is in fluid communication with a fluid phase port of the second phase contact device whereby fluid is able to flow from the first phase contact device to the second phase contact device.

25. A system of clause 23 wherein the first and second phase contact devices are arranged to receive fluid from the first fluid source in that both are arranged to communicate with the first fluid source via a flow path which does not include any said phase contact device.

26. A system of any of clauses 23 to 25 wherein the first and second phase contact devices are releasably coupled together.

27. A system of any of clauses 23 to 26 wherein the first and second phase contact devices each comprise releasably interconnected plates, the plates comprising a pair of plates which are in opposed face-to-face relationship and which define between their opposed faces a length of the conduit extending in a direction parallel with the pair of plates, and wherein one plate of the pair of plates of the first phase contact device is shared by the second phase contact device to form one plate of the pair of plates of the second phase contact device.

28. A system of any of clauses 23 to 27 which further comprises at least one roller between each of the phase contact modules along the solid phase pathway, to guide the solid phase as it moves from one phase contact device to the next.

29. A system of any of clauses 23 to 28 wherein at least some of the successive phase contact devices are arranged in one or more phase contact device stacks, the or each stack comprising a plurality of phase contact devices which are coupled together and which are in, or are capable of being put in, fluid communication with a common fluid source for the phase contact devices of that stack, said first and second phase contact devices being disposed in the same stack.

30. A system of clause 29 wherein the or each stack further includes a housing which accommodates the phase contact devices and to which are connected rollers arranged to guide the solid phase along the solid phase pathway outside the phase contact devices.

31. A system of clause 30 wherein at least one roller of each stack is a drive roller in connection with a drive device for causing the roller to rotate and drive the solid phase.

32. A system of any of clauses 23 to 31 which further includes a deposition device arranged outside the successive phase contact modules for depositing a reagent on the solid phase as it moves along the pathway, the device optionally being disposed between two of the successive phase contact modules.

33. A system of clause 32 which comprises a deposition zone in which there are arranged a plurality of deposition devices along the pathway for depositing reagents on the solid phase, optionally in spatially addressed manner.

34. A system of any of clauses 23 to 33 which further includes a sensor device arranged outside the successive phase contact devices for determining a parameter of the solid phase as it moves along the pathway.

35. A system of any of clauses 23 to 32 wherein the pathway has arranged along it in succession:

a deposition device for depositing a reagent on the solid phase as it moves along the pathway; then a phase contact module; and then a sensor device for determining a parameter of the solid phase as it moves along the pathway.

36. A system of any of clauses 23 to 35 which further comprises a framework to which the phase contact devices and optionally one or more additional modular components of the system are releasably couplable along the pathway, at least some of the successive phase contact devices optionally being arranged in one or more modular phase contact device stacks, the or each stack comprising a plurality of phase contact devices which are coupled together and which are in, or are capable of being put in, fluid communication with a common fluid source for the phase contact devices of that stack, said first and second phase contact devices being disposed in the same stack.

37. A system of any of clauses 28 to 31 wherein the stacks are modular and the system further includes a framework to which the stacks and optionally one or more additional modular components of the system are releasably couplable along the pathway, the additional modular components comprising a modular deposition device for depositing a reagent on the solid phase as it moves along the pathway, or a modular sensor device for determining a parameter of the solid phase as it moves along the pathway, or both.

38. A system for carrying out a heterogeneous process, comprising:

a treatment apparatus configured to contain a flowing fluid phase and a longitudinally moving elongate solid phase in mutual contact;

a controllable drive device for moving the solid phase through the treatment apparatus;

a controllable fluid metering device for providing a controlled fluid phase flow to the treatment apparatus;

a sensor arranged to detect a parameter of the solid phase after the solid phase has passed through the treatment apparatus;

a processor adapted to be in signal communication with the sensor and with at least one of the drive device and the fluid metering device to receive an input signal from the sensor and send an output signal to the at least one of the drive device and the fluid metering device, the processor being programmed to control the at least one of the drive device and the fluid metering device responsive to the detected parameter.

39. The system of clause 38 which further comprises a controllable energy source which is arranged for energy to be supplied from the source at least to the fluid phase and the solid phase where they are in mutual contact, and which is in signal communication with the processor, the processor being programmed to control the energy source responsive to the detected parameter.

39. The system of clause 39 wherein the energy source comprises a heat source, an ultrasound transducer or a magnetron, laser, light emitting diode, mercury vapour lamp (UV source), or other source of electromagnetic radiation, and/or wherein the controllable fluid metering device comprises a pump or a valve, or a combination thereof.

41. The system of clause 39 wherein the sensor comprises a spectrometer or a fluorescence detector.

42. The system of any of clauses 37 to 41, wherein the fluid is a liquid and the treatment apparatus defines:

a closed channel;

at a first end portion of the channel and in communication therewith a first liquid port and a first solid port; and at a second end of the channel a second liquid port and a second solid port, whereby in use the liquid phase flows through the first liquid port, along the channel and out of the second liquid port and the solid phase moves through one of the first and the second solid ports, along the channel and then moves out of the other of the first and second solid ports, the apparatus being configured to prevent substantial passage of the liquid through the solid phase ports from the closed channel.

43. A modular system for carrying out a heterogeneous process, comprising:

a plurality of treatment assemblies for contacting a longitudinally mobile elongate solid phase with a flowing fluid phase, the assemblies being provided in a modular arrangement and each assembly defining a lumen to contain the mobile solid phase and the flowing fluid phase in contact with each other, and each assembly being capable of being releasably connected on first side to a portion of a second said assembly and on a second side to a portion of a third said assembly to form a treatment zone comprising three said treatment assemblies in succession and defining a continuous pathway for an elongate solid phase to move through the treatment assemblies comprised in the treatment zone.

44. A system of clause 43 which further comprises:

a drive module comprising a controllable drive device for the direct or indirect application of force to the solid phase to move it along the pathway, the system being adapted for the drive module to be mounted such that it remains in fixed position relative to the treatment assemblies during operation of the system;

a metering module comprising a controllable fluid metering device for providing a controlled fluid phase flow to the treatment devices, the system being adapted for the fluid metering module to be mounted such that it remains in fixed position relative to the treatment assemblies during operation of the system;

a sensor module comprising a sensor arranged to detect a parameter of the solid phase after the solid phase has passed through the treatment zone, the system being adapted for the sensor module to be mounted such that it remains in fixed position relative to the treatment assemblies during operation of the system;

a processor adapted to be in signal communication with the sensor and with at least one of the drive device and the fluid metering device to receive an input signal from the sensor and send an output signal to the at least one of the drive device and the fluid metering device, the processor being programmed to control the at least one of the drive device and the fluid metering device responsive to the detected parameter.

45. The system of clause 44 which further includes a framework on which the treatment assemblies, the drive module, the metering module and the sensor module are adapted to be mounted.

46. The system of clause 45 wherein at least some of the treatment assemblies are arranged in one or more treatment device stacks, the or each stack being a module comprising a housing in which are accommodated a plurality of treatment assemblies which are coupled together and which are in, or are capable of being put in, fluid communication with a common fluid source for the treatment devices of that stack, the or each stack being adapted to be mounted on the framework.

47. The system of any of clauses 43 to 46 wherein the fluid phase is a liquid phase and each said assembly and, in the case of clause 46, stack is mounted on the framework.

48. A process for treating a mobile elongate solid phase with a flowing fluid phase, comprising moving the solid phase and the fluid phase through a lumen of a conduit in which the two phases come into mutual contact.

49. A process of clause 48 which comprises:

moving the solid phase through a first solid phase port of an apparatus of any of clauses 1 to 17 into the lumen of the apparatus, though the lumen and out through a second solid phase port of the apparatus;

causing a fluid phase to enter the lumen of the apparatus through a first fluid phase port, flow through the lumen and leave through a second fluid phase port.

50. A process of clause 48 or clause 49 wherein the fluid phase is caused to flow through the lumen in an opposite direction to the movement of the solid phase.

51. A process of clause 49 or clause 50 wherein the elongate solid phase is in the form of a ribbon.

52. A process of any of clauses 48 to 51 wherein the elongate solid phase comprises a substrate and optionally a substance bonded thereto.

53. A process of clause 52 wherein the substrate comprises cotton or another cellulosic material, a synthetic polymer or glass.

54. A process of clause 52 or clause 53 wherein the substrate has a substance bonded thereto.

55. A process of any of clauses 51 to 54 wherein the fluid phase comprises a reagent which reacts with the substrate or with a substance bonded thereto.

56. A process of clause 55 wherein the fluid phase is a liquid phase and the process comprises solid phase synthesis, and the reagent reacts with the substrate to remove a protecting group, to activate a functional group or to add a synthetic building block to the substance by covalent bond formation.

57. A process of clause 53 wherein the fluid phase is a liquid phase which comprises a biological molecule or a specific binding partner for a biological molecule or another agent which, when it contacts an analyte having a predetermined property, undergoes a process specific to such analyte to create a detectable response.

58. A process of clause 57 which further comprises detecting for the detectable response.

59. A process of any of clauses 48 to 52 wherein the fluid phase is a liquid phase, and wherein the liquid phase washes the elongate solid phase.

60. A process of any of clauses 51 to 59 wherein the apparatus is a first said apparatus and which is in combination with a second said apparatus to provide a pathway along which the elongate solid phase is moved out of the second solid phase port of the first apparatus and into a first solid phase port of the second apparatus, and then through the lumen of the second apparatus and out of a second solid phase port of the second apparatus while a fluid is caused to flow through the second apparatus.

61. A process of clause 60 wherein a common fluid source supplies the fluid which flows through the first said apparatus and the second said apparatus.

62. A process of clause 60 wherein the fluid which flows through the first apparatus is supplied from a different fluid source to the fluid which flows through the second apparatus.

63. A process of clause 62 wherein the fluid which flows through the first apparatus comprises a reagent which reacts with the substrate or with a substance bonded thereto or comprises a labelled agent, and the fluid which flows through the second apparatus washes the elongate solid phase.

64. A process of any of clauses 60 to 62 which comprises a solid phase synthesis, wherein the elongate solid phase is moved through a plurality of said apparatuses in succession in carrying out the synthesis, the solid phase and the fluid phase in each of the apparatuses being contacted together to perform a respective step of the synthesis, each of said respective steps being performed either in a single said apparatus or in a plurality of said apparatuses arranged one after the other.

65. A process of any preceding clause which further comprises depositing an agent onto the elongate solid phase from a deposition device.

66. A process of clause 64 which further comprises spatially addressing a plurality of synthetic building blocks onto the elongate solid phase to cause them to react with the substrate or a substance bonded thereto, to form an array of different substances.

67. A process of clause 66 wherein the solid phase synthesis results in a post-synthetic solid phase which comprises an array of spatially distinct areas, each area containing end product molecules of a respective predetermined structure bonded to the substrate, the process further comprising:

exposing the post-synthetic solid phase to an agent which, when it contacts an analyte having a predetermined property, undergoes a process specific to such analyte to create a detectable response; and determining the presence and/or amount of the detectable response of each spatially distinct area.

68. A process of clause 67 wherein the exposing step comprises passing the post-synthetic solid phase through the conduit of an apparatus of any of clauses 1 to 12 whilst also passing through the conduit a liquid phase which comprises said agent.

69. A process of clause 67 or clause 68 which further comprises:

identifying an end product molecule structure resulting in a predetermined detectable response;

repeating the process of clause 67 or clause 68 to create modifications of the structure resulting in a predetermined detectable response, each modification occupying a said spatially distinct area; and determining the amount of the detectable response of the spatially distinct areas occupied by the modifications.

70. A process of any of clauses 64 to 69, which involves the use of an apparatus as defined in clause 17, and wherein the sensor determines a parameter indicative of the yield or purity of a substance bonded to the substrate, and the processor is programmed to control the at least one controllable device to improve the yield or purity.

71. A process for synthesising and screening molecules, comprising:

moving an elongate solid phase through sequential treatment stations, each for performing a respective stage of a solid phase synthesis, at least one of the treatment stations being adapted to spatially address synthetic building blocks onto the solid phase, whereby to form on the solid phase at the end of the synthesis an array of spatially distinct areas, each area occupied by end product molecules of a respective predetermined structure;

moving the solid phase on which the array is formed through a treatment station where it is contacted with an agent which, when it contacts an analyte having a predetermined property, undergoes a process specific to such analyte to create a measurable response;

measuring the amount of the measurable response of each spatially distinct area; and identifying an end product molecule structure resulting in a predetermined measurable response.

72. A process of clause 71 which further comprises the steps of:

repeating the process of clause 71 to create modifications of the structure resulting in a predetermined measurable response, each modification occupying a said spatially distinct area; and measuring the amount of the measurable response of the spatially distinct areas occupied by the modifications.

73. A process of clause 72 wherein the end product molecules comprise a polymer selected from a polysaccharide, a polypeptide and a polynucleotide, and the modification comprises changing the monomer sequence of the polymer.

74. A process of clause 72 wherein the end product molecules comprise small organic molecules and the modification comprises changing the structure of at least one part of the molecule.

75. A process of clause 72 wherein the end product molecules comprise small organic molecules and the structure resulting in a predetermined detectable response comprises a cyclic moiety having at least one substituent and the modification comprises changing the structure of the substituent.

76. A process of clause 72 wherein the end product molecules comprise small organic molecules and the structure resulting in a predetermined detectable response comprises at least one functional group, and the modification comprises reacting the functional group to form a plurality of different structures.

77. A process of any of clauses 72 to 76 wherein a computer programmed to identify the end product molecule structure resulting in the predetermined measurable response and to change at least one synthetic stage of the solid phase synthesis responsive to the identified structure causes the process of clause 71 to be repeated with a change of synthetic building block in at least one synthetic stage.

78. A process of any of clauses 71 to 78 wherein:

said agent comprises a labelled binding member and the measuring comprises washing the solid phase and then measuring a parameter indicative of the amount of label bound to the solid phase through the end product molecules; or said agent comprises an enzyme and an enzyme substrate, the enzyme substrate having a measurable parameter which is changed by the activity of the enzyme on the substrate, and the measuring comprising measuring said measurable parameter.

79. A process of clause 78, wherein the enzyme substrate is chromogenic or fluorogenic.

80. A process of clause 78 or clause 79, wherein the contacting with the agent comprises sequentially contacting the solid phase with the enzyme and then the enzyme substrate.

81. An apparatus for use in synthesising and screening molecules, the apparatus providing a pathway for an elongate solid phase to move along and comprising disposed along the pathway in a direction from upstream to downstream:

sequential treatment stations, each for performing a respective stage of a solid phase synthesis, at least one of the treatment stations comprising plural deposition devices for spatially addressed deposition of synthetic building blocks onto the solid phase;

a treatment station for contacting the solid phase with an agent which, when it contacts an analyte having a predetermined property, undergoes a process specific to such analyte to create a measurable response; and a measuring station for measuring the amount of the measurable response of each spatially distinct area, the apparatus further comprising a computer which is adapted to be in signal communication with, or which is in signal communication with, the measuring station and programmed to identify the predetermined measurable response and to determine the corresponding end product molecule structure from data available to the computer.

82. An apparatus for use in synthesising and screening molecules, the apparatus providing a pathway for an elongate solid phase to move along, the apparatus comprising disposed along the pathway in a downstream direction:

sequential treatment stations, each for performing a respective stage of a solid phase synthesis, at least one of the treatment stations comprising plural deposition devices for spatially addressed deposition of synthetic building blocks onto the solid phase and at least one of the treatment stations comprising the apparatus of any of clauses 1 to 22;

a treatment station for contacting the solid phase with an agent which, when it contacts an analyte having a predetermined property, undergoes a process specific to such analyte to create a measurable response; and a measuring station for measuring the amount of the measurable response of each spatially distinct area.

83. An organic semiconductor polymer attached to an elongate solid phase.

Subject Matter Disclosed in PCT/GB2008/002288

There will next be described aspects and embodiments of the disclosure which are described in PCT/GB2008/002288, to which priority is claimed.

According to a further aspect of the present invention, therefore, there is provided a solid phase reaction method comprising passing an elongate material with a substance provided thereon through at least one reaction zone and reacting said substance in said zone.

Using an elongate material enables a continuous process to be performed.

The elongate material may be passed through the at least one reaction zone continuously or intermittently.

Preferably said substance is reacted with a substance in solution, said solution being provided in said zone. Alternatively or additionally, said substance may be reacted with a liquid or gas provided in said zone.

Preferably said substance is provided on said material in one of said reaction zones.

Preferably said material is substantially insoluble in the contents of said at least one reaction zone. Preferably said material is a polymer. Said polymer may be natural or synthetic. Preferably said material comprises groups that allow for attachment to at least one linker species of said substance. Said at least one linker species may comprise free hydroxyl, amino, or amide groups, or any other suitable group. In one embodiment said material is cellulose. In said embodiment cotton may be used. The cellulose or cotton may be suitably pre-treated. For example the cotton may be soaked in a solution of coupling agent (diisopropylcarbodiimide), and a spacer (aminohexanoic acid). The spacer is a flexible molecule that improves access of the linker to the solvated species. The cord is washed, deprotected and next a linker (Rink) is coupled to the spacer using the coupling agent HATU.

Preferably the elongate material is in a form that maximises its surface area to volume ratio. For example the elongate material may be ribbon, cord, thread, tape or of any other suitable form. Maximising surface area to volume ratio maximises the extent of the reaction of between the reactants and the substance and maximises the use of reagents.

Using such an elongate material is much simpler and more convenient than with other forms of solid phase, for example beaded resins require the use of expensive fritted glass vessels.

The elongate material may be easily exposed to short path length energy sources, such as ultrasound, microwaves and other electromagnetic waves by virtue of its small cross section. With batch processes, due to their large size, it is much more difficult to expose all of the batch to such energy sources. These energy sources may accelerate chemical reactions and enhance yields and product purity when compared with an equivalent thermal energisation.

Preferably said at least one reaction zone is configured to optimise the exposure of reagents to said energy sources. The use of microwaves and/or ultrasound has been shown to improve the efficiency of some chemical reactions. These techniques are important in reducing the environmental cost of chemical processes through reducing the consumption of materials and energy.

Preferably said elongate material is passed through a plurality of said reaction zones. Said substance may be reacted in each reaction zone.

Preferably said elongate material is passed through at least one rinsing zone, wherein the elongate material and/or said substance is subject to rinsing by a rinsing agent.

The elongate material may be passed through the at least one rinsing zone continuously or intermittently.

Preferably said elongate material is passed through a plurality of rinsing zones.

The at least one reaction and/or rinsing zone may host at least one reagent in any phase suitable for the desired reactions. Preferably the reaction and rinsing zones host a plurality of said reagents. Preferably the at least one reaction zone is configured to ensure optimal reagent use through the control of the flow of the elongate material and of said at least one reagent.

The above method allows the reaction or reactions of said substance on the elongate material in said reaction zone or zones, as well as the rinsing of the material and/or said substance to be carried out continuously, as the elongate material passes from zone to zone.

The elongate material may be a tape form of insoluble solid phase matrix.

Preferably said elongate material is passed through reaction and rinsing zones alternately.

Preferably said at least one reaction zone is equipped with testing apparatus for the collection of data from said elongate material.

Preferably movement of the elongate material through the at least one reaction zone or, where applicable, through the reaction zones and/or the rinsing zones is effected by a drive means. The drive means may comprise at least one rotatable unit such as a roller, spool or any other suitable device. In one embodiment, the elongate material is magnetic and the drive means comprises at least one induction coil used to create a magnetic field such that said movement of the elongate material is effected.

Where the drive means comprises a plurality of rotatable units, a control means is preferably operatively connected to the drive means such that the rotatable units rotate in sychronisation with each other. This ensures that a constant tension is maintained in the elongate material. This may be achieved by connecting the rotatable units with a drive belt, preferably a toothed drive belt.

Similarly, where the drive means comprises a plurality of induction coils, a control means is preferably operatively connected to the induction coils to control a magnetic field created by the induction coils such that a constant tension is maintained in the elongate material.

Preferably said zones are connectable with each other and with said drive means. This connectability is preferably modular. In this way, a long chain of reaction and/or rinsing zones may be connected to each other and to one or a plurality of drive means in order to provide a long chain of reaction and rinsing stages. Such connectability allows combinations and sequences of said zones to be varied easily allowing a wide range of reactions to be produced using this method. Said zones may be manufactured and sold as "off the shelf units", allowing a process plant suitable for using such a method, to be assembled and disassembled quickly.

In one arrangement a number of substantially identical modules arranged to be connected together are provided.

A reaction product may remain attached to the elongate material as the elongate material is removed from said at least one reaction zone. The product may then be cleaved from said elongate material. Before the product is cleaved, a spectrometer may analyse the product.

Alternatively, the product may separate from the elongate material in the reaction zone.

Reactants and/or reagents which may be different reactors or reagents may be deposited onto defined areas of the elongate material. This allows for a large number of different compounds to be prepared on the elongate material and also allows each of these compounds to be subject to testing, for example biological or spectrographic testing.

The reacting of said substance may comprise the step of reacting the substance with a solution to form a product which is insoluble in the solution and may then be removed from the solution. This may comprise the step of forming a metal complex between the substance and a substance present in the solution. Alternatively or additionally this may comprise the step of forming a biological compound between the substance and a substance present in the solution. The substance present in the solution may be in any form, for example in suspension or solution.

In one embodiment of the invention, the substance is a reagent.

The method may comprise the step of testing said substance or the product of one or more reactions with said substance for biological activity.

The elongate material may be passed through a plurality of reaction zones sequentially wherein at least two of said zones contain differing reactions.

The elongate member may be endless. In this case, the elongate member may be in the form of a loop. Where the elongate member is endless, the elongate member may be continuously or intermittently passed through said at least one reaction zone and/or said at least one rinsing zone.

The method may be used independently or in conjunction with a traditional batch reactor.

According to a second aspect of the present invention there is provided apparatus for performing the method of the first aspect of the invention, said apparatus comprising an elongate material with a substance provided thereon and a reaction zone, arranged such that the elongate material is moveable through the reaction zone such that the substance may be reacted in the reaction zone.

Preferably the apparatus comprises a fluid source connected to an inlet to the reaction zone such that fluid may be supplied to the reaction zone from the fluid source and wherein the fluid comprises at least one reactant for reaction with said substance. Preferably the fluid is a liquid. More preferably the liquid is a solution. Preferably fluid supplied to the reaction zone flows through the zone and out of an outlet from the reaction zone.

Preferably the reaction zone is a conduit.

Preferably a drive means effects the movement of the elongate member through the reaction zone. The drive means may be a stepper motor, induction coil or any other suitable device.

Preferably the drive means is operatively connected to a control means. Where the drive means is a motor, the control means preferably comprises a computer connected to a motor controller.

The computer unit is preferably operatively connected to the stepper motor via the motor controller. The speed of rotation of the motor can preferably be set by appropriate inputs to the computer unit. The motor is preferably arranged to drive the elongate member through the reaction zone. A flexi drive is preferably used to couple the motor to the elongate member.

Preferably the conduit is provided in at least one block. Preferably the apparatus comprises at least three blocks and the conduit is formed within the blocks. Each of the blocks may be generally cuboidal, each having a front face, rear face, top face, bottom face and opposed side faces. The blocks are preferably formed from glass, poly(tetrafluoroethane) (PTFE), or any other suitable material. The blocks may occupy an upright orientation and be connected to each other such that the blocks occupy front, central and rear positions.

In this case, the rear face of the front block preferably is in contact with the front face of the central block and the rear face of the central block preferably is in contact with the front face of the rear block.

The blocks are preferably connected to each other by a fastening means. For example, a row of apertures may be provided along opposed side edges of each block extending in a direction substantially parallel to the side edges and indented inwardly of the side edges. Respective said apertures in the blocks are preferably aligned with each other, bolts are preferably passed through said apertures and nuts are preferably engaged with respective bolts so as to fix the blocks together.

Preferably a channel is provided along the rear face of the front block. In this case, the channel preferably has a U-section and extends from the top of the block, in a direction substantially parallel to the side edges of the block. The channel preferably terminates at a height above a bottom of the block. A front face of the central block is preferably in contact with the rear face of the front block such that it closes the channel, to form a conduit.

Preferably an inlet aperture is provided in the front face of the front block towards the top of the block. An inlet bore preferably extends from the inlet aperture, in a direction substantially perpendicular to the channel, and terminates at a point of intersection with the channel.

The central block is preferably provided with an aperture towards a bottom of and extending through the block. A roller is preferably rotatably mounted within the aperture.

In a similar arrangement as with the front block, a channel is preferably provided along the front face of the rear block. The channel preferably has a U-section and extends from the top of the block, in a direction substantially parallel to the side edges of the block. The channel preferably terminates at a height above the bottom of the block. A rear face of the central block is preferably in contact with the front face of the rear block such that it closes the channel, to form a conduit.

Such channels are preferably suitable to receive the elongate member.

An outlet aperture is preferably provided in the rear face of the rear block towards the top of the block. An outlet bore preferably extends from the outlet aperture, in a direction substantially perpendicular to the channel, and terminates at a point of intersection with the channel.

The aperture in the central block preferably intersects the channels in the front and rear blocks such that, in effect, a continuous conduit is created from the inlet aperture in the front block to the outlet aperture in the rear block. This continuous conduit preferably forms the reaction zone.

The elongate member is preferably fed into the top of the front block through the channel in the block. The elongate member preferably passes downwardly through the channel in the front block, is looped underneath the roller in the central block, passes upwardly through the channel in the rear block and out of the top of the rear block.

The fluid source is preferably connected to the inlet aperture in the front block via a fluid feed line. Fluid in the fluid source is preferably forced under pressure through the fluid feed line, into the inlet aperture, through the inlet bore, downwardly through the channel in the first block, from where it flows out through the cavity in the central block, upwardly through the channel in the rear block, through the outlet bore, through the outlet in the rear block and back into a return section of the fluid feed line.

A substance to be reacted is preferably provided on the elongate member. Alternatively the substance may be linked to the elongate member in the reaction zone. The elongate member preferably comprises a polymeric material suitable to host a solid phase reaction. For example the polymeric material is preferably substantially insoluble in the fluid present in the reaction zone and comprises groups that allow for attachment to at least one linker species of the substance. In the present embodiment the material is cellulose, or cotton. Any group that may act as a linker group may be appropriate.

The three blocks of the reactor may be disassembled. This provides a means of cleaning the apparatus and also an easy means of passing the solid phase ribbon through the channels in the blocks.

The inlet and outlet for the elongate member are preferably disposed above the inlet and outlet for the fluid. In this way, the elongate member may be easily separated from the fluid.

Since there are separate inlet and outlet points for the solid phase ribbon and the fluid, this allows for the solid phase ribbon and fluid to flow in the same direction or in reverse directions. Flowing in the reverse direction allows a concentration gradient to be established.

One way of increasing the time of the reaction and/or the amount of product produced by the reaction, under given conditions, is to increase the size of the reaction zone, for example by increasing the height of the channels and the length of the solid phase ribbon. However, due to obvious physical constraints, the height of the channels is limited and therefore the time of the reaction and/or the amount of product that may be produced under given conditions is limited.

The present embodiment of the invention seeks to overcome this issue. A number of said blocks may be connected together side by side to form a number of reaction zones. In such a configuration, the solid phase ribbon may be passed from the outlet of one block into the inlet of an adjacent block.

A single source of fluid may supply all of the reaction zones, with fluid feed lines connecting each of the blocks together.

The assembly of blocks may be such so as to replicate the synthetic pathway.

In order that the aspects and embodiments disclosed in PCT/GB2008/002288 may be more fully understood, embodiments thereof will now be described with reference to FIGS. 24 to 34.

Referring to FIGS. 24 to 34, a solid phase synthesis reaction according to the present invention comprises a cord 701, being passed through a series of zones 702. Cord 701 is fed from cord spool 703 in direction of arrow 707.

Cord 701 is a polymeric material suitable to host a solid phase reaction. In the present embodiment the material is cellulose, or cotton. However, a cord that comprises chemical groups that allow reaction with a suitable chemical species for the reaction to be undertaken may of course be used. Any group that may act as a linker group may be appropriate. The link may later be cleaved in any suitable manner, such as chemically, enzymatically or using radiation. Groups such as free hydroxyl, amino, or amide groups may be appropriate linker groups, although there are many hundreds of known alternatives which would also be suitable.

It is evident that cord 701 may be of varying diameters. Cord 701 may be substituted with any other suitable elongate form, such as a tape, ribbon or thread.

It is desirable to maximise surface area to volume ratio of the polymeric material. Maximising surface area to volume ratio maximises the extent of the reaction of between the reactants and the chemical species and maximises the use of reagents.

The cord 701 passes through a series of zones 702, which may involve reaction or rinsing. In the present embodiment the zones host reaction and rinsing phases alternately. Evidently the zones 702 may host appropriate phases for whatever reaction is to be performed; any combination of reaction or rinsing stages might be appropriate. The zones 702 may of course host reagents in any phase suitable for the desired reactions.

In passing the cord 701 through the reaction zones the cord 701 is fed through said zones 702, either continuously or intermittently. For the most part, when the methodology of the present invention is being used, at any one instant different parts of the cord 701 are passing through different reaction zones 702; this is in contrast to the traditional batch process method of reaction.

Figure 24:
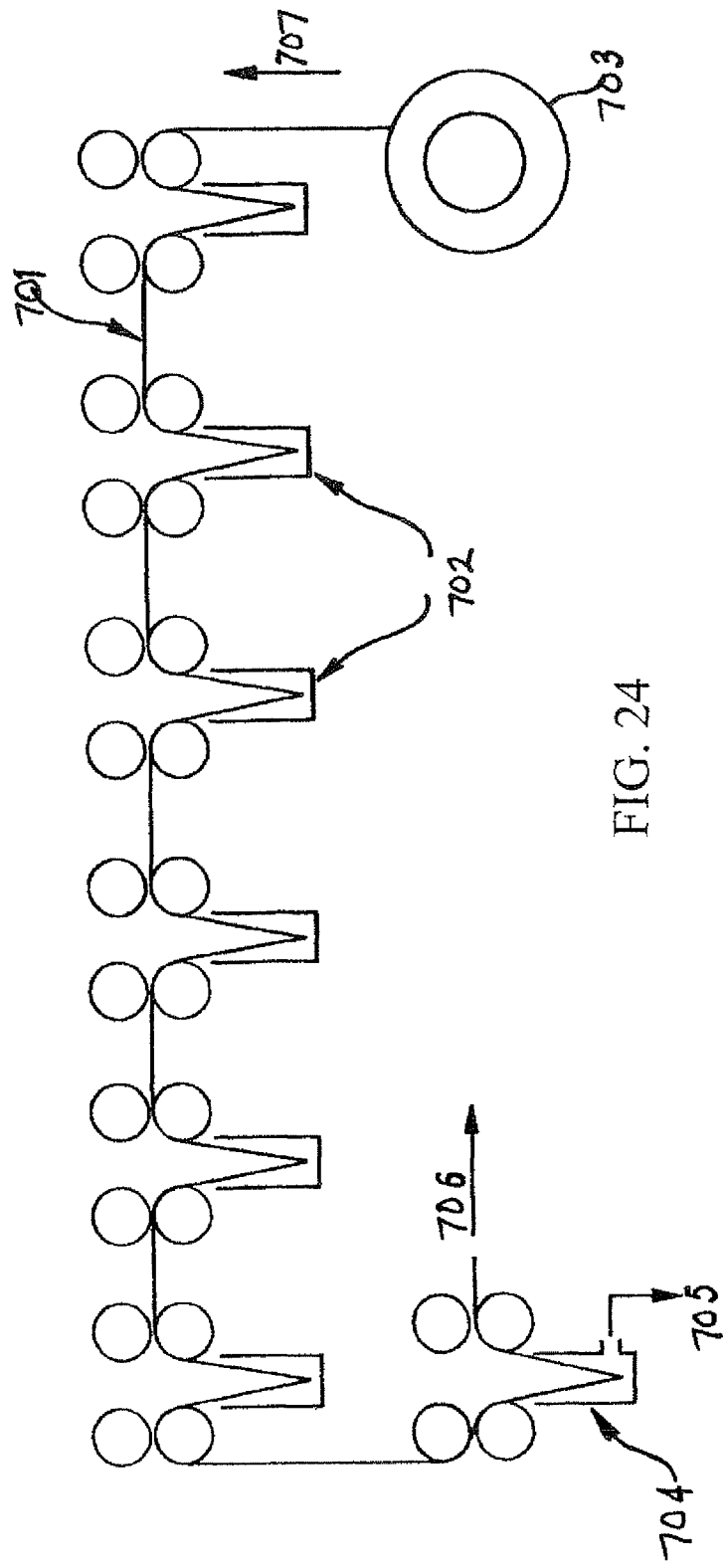
FIG. 24 is a schematic diagram of a multistep continuous synthesis reaction according to the present invention.

In the present embodiment a chemical species is linked to the cord 701 in one of the zones 702 that the cord 701 passes through, but evidently said species may be provided on said cord 701 before the reaction scheme of FIG. 24 is commenced.

The species then undergoes a reaction in the next reaction zone. The product of this reaction subsequently undergoes a further reaction in another reaction zone, and so on, until in zone 704 a product is cleaved from the cord and removed to storage 705. The cord 701 is removed with arrow 706, to be reused or to waste.

Figure 25:
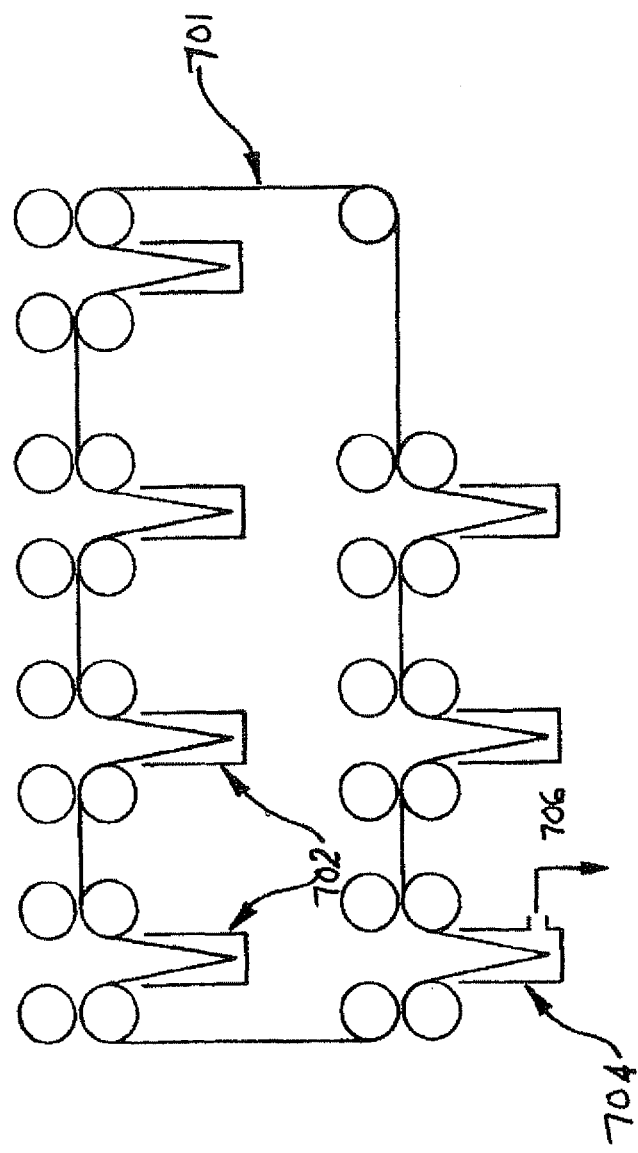
FIG. 25 is a schematic diagram of a multistep recycling synthesis reaction according to the present invention.

FIG. 25 shows a reaction scheme in accordance with the present invention arranged such that the cord 701 is continuously recycled.

Figure 26:
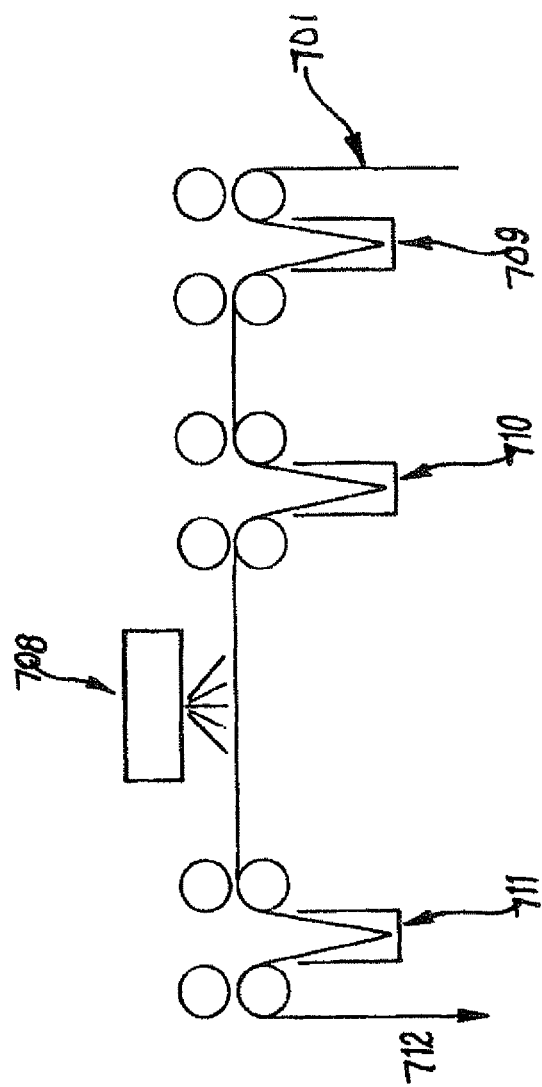
FIG. 26 is a schematic diagram of a multistep microwave assisted reaction according to the present invention.

FIG. 26 is a schematic diagram of a microwave assisted reaction. Zones 709 and 710 contain differing reagents, and cord 701 is passed sequentially through these. Cord 701 is then subjected to microwaves from microwave source 711 so as to assist a reaction between said reagents and a species provided on the surface of said cord. Cord 701 continues with arrow 712 for the species provided thereon to undergo further reactions or for cleavage of a product.

Figure 27:
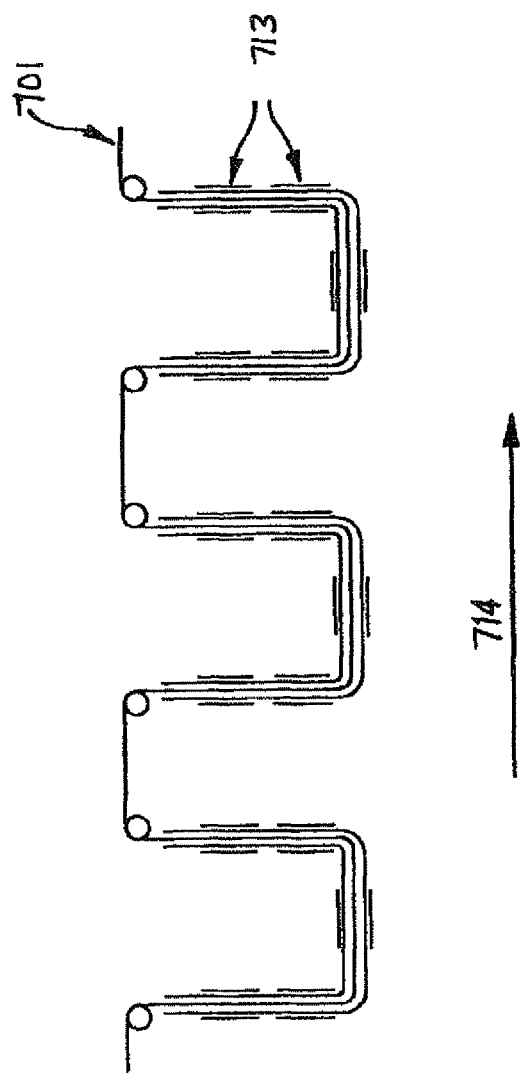
FIG. 27 is a schematic diagram of a magnetic cord being propelled through the reaction zones by magnetic fields.
Figure 28:
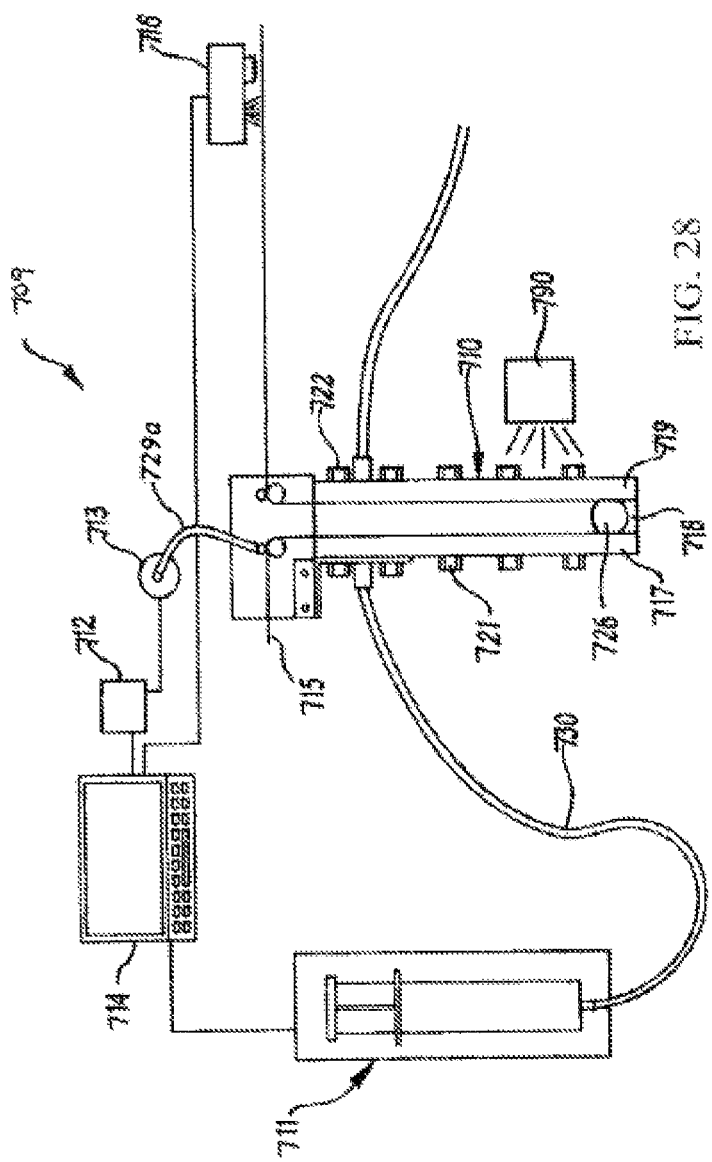
FIG. 28 is a schematic diagram of apparatus according to a further aspect of the present invention.
Figure 29:
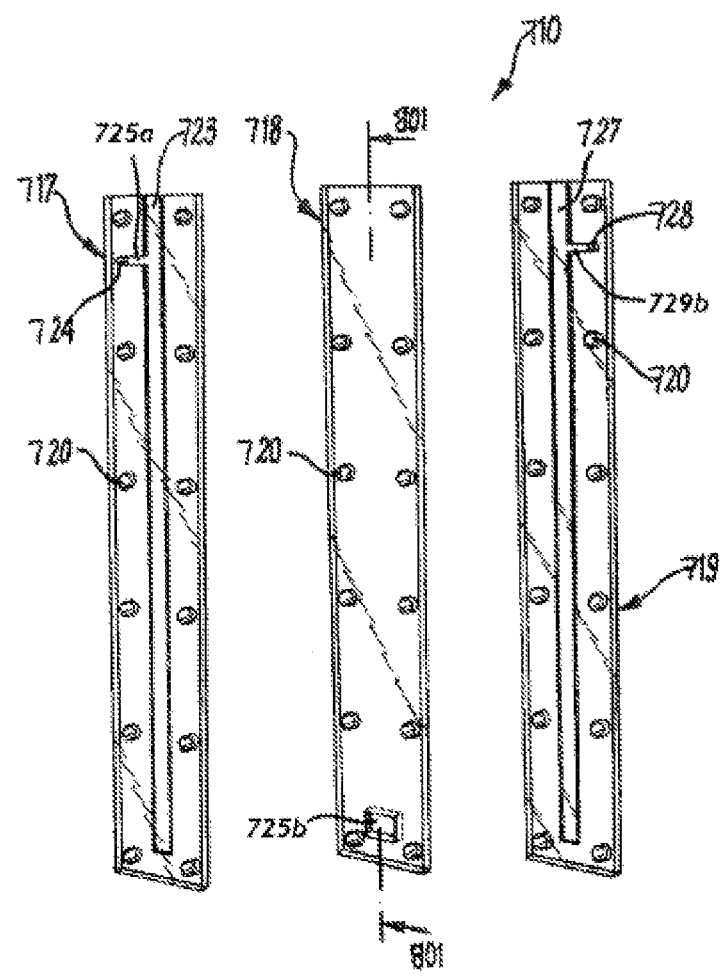
FIG. 29 is an enlarged exploded view of the reactor shown in FIG. 28.

FIG. 27 is a schematic diagram showing how movement of cord 701 in direction of arrow 714 is effected through magnetic fields generated by induction coils 713. In this instance cord 701 is itself magnetic. Cord 701 may be made magnetic through imbuing cord 701 with magnetic particles.

The method of the present invention has numerous applications, and may be used for various solid phase reactions, including solid phase synthesis as described above, wherein a product is removed from the cord.

Also possible is metal scavenging wherein species provided on the cord form a complex with metal in aqueous solution and thereby remove said metal from said solution. This application is, however, not limited to metal scavenging, as other species may be scavenged, for example biological compounds.

Further, there is the possibility of preparing chemical species on the cord and then testing said species for biological activity without cleaving said species from the cord.

The scheme of the present invention has several advantages over the prior art. Firstly the cord can be handled easily, using rollers and spools; whereas beaded resins, previously used, require expensive fritted glass vessels.

The cord may be easily exposed to energy sources, such as ultrasound, microwaves and other electromagnetic waves. This is by virtue of the small cross-section of the reactor (large batch reactors require large and expensive arrays of sources).

Furthermore, reagents/reactants can be deposited onto defined areas of the cord, these defined areas corresponding to a particular product. This allows for a plurality of and specifically a large number of different compounds to be prepared on the cord and these 'spatially addressed' compounds subjected to testing, for example biological or spectrographic testing.

In an alternative embodiment of the invention the cord can be used as a solid supported reagent. In this application a particular chemical entity is present on the cord and is moved through (a solution of) reactants, such that the spent cord is easily removed from the liquid once the desired reaction has occurred. Essentially this is the mirror image of the method of operation described above, as the desired product(s) remains in at least one of the reaction zones after the cord has been passed through them.

The inventive arrangement herein described allows for continuous multi-step production of complex chemicals; a continuous flow of product may be collected.

The cord may be moved counter-current to the reagent(s) used, such that fresh reagent enters one end and exhausted reagent leaves the other; thus efficiently using said reagent(s). The movement of the cord counter-current to the reagent(s) creates a concentration gradient such that the efficiency of said rinsing process is improved.

In this application, the elongate material is housed within a conduit as it is passed through said zones. The conduit has a cross-sectional area suitable to contain the flow of the (solution of) reactants and the cord. When too narrow a channel is used, the movement of the cord causes unwanted movement of the (solution of) reactants. When too wide a channel is used, too much of the (solution of) reactants is wasted.

A further embodiment of the invention is shown in FIGS. 28 to 34. Apparatus 709 comprises a reactor 710, a syringe and syringe drive 711, a motor controller 712, a stepper motor 713, a computer unit 714, a solid phase ribbon 715 and a spectrometer 716.

The reactor 710 comprises a front block 717, a central block 718 and a rear block 719. Each of the blocks are generally cuboidal and formed from glass. Alternatively the blocks may be formed from poly(tetrafluoroethane) (PTFE), which is cheaper to machine. A row of apertures 720 is provided along opposed side edges of each block 717,718,719 extending in a direction substantially parallel to the side edges and indented inwardly of the side edges. Respective apertures 720 in the blocks 717,718,719 are aligned with each other. Bolts 721 pass through respective aligned apertures and nuts 722 are engaged with respective bolts 721 so as to fix the glass blocks 717,718,719 together.

A channel 723 is provided along a rear face of the front block 717. The channel 723 has a U-section and extends from a top side of the block 717, in a direction substantially parallel to the side edges of the block 717. The channel 723 terminates at a height above a bottom edge of the block 717. A front face of the central block 718 is in contact with a rear face of the front block 717 such that it closes the channel 723 to form a conduit. The channel 723 is of suitable dimensions to receive a solid phase ribbon 715.

An inlet aperture 724 is provided in the front face of the front block 717 towards a top of the block 717 and disposed to one side of the block 717. An inlet bore 725a extends from the inlet aperture 724 in a direction substantially perpendicular to the channel 723 and terminates at a point of intersection with the channel 723.

The central block 718 is provided with an aperture 725b towards a bottom of the block 718, within which a roller 726 is rotatably mounted relative to the block.

In a similar arrangement as with the front block 718, a channel 727 is provided along a front face of the rear block 719. The channel 727 has a U-section and extends from a top side of the block 719 in a direction substantially parallel to the side edges of the block 719. The channel 727 terminates at a height above a bottom edge of the block 719. A rear face of the central block 718 is in contact with the front face of the rear block 719 such that it closes the channel 727 to form a conduit. The channel 727 is of suitable dimensions to receive a solid phase ribbon 715.

An outlet aperture 728 is provided in a rear face of the rear block 719 towards the top of the block 719 and disposed to one side of the block 719. An outlet bore 729b extends from the outlet aperture 728 in a direction substantially perpendicular to the channel 727 and terminates at a point of intersection with the channel 727.

The cavity 725b in the central block 718 intersects the channels 723,727 in the front and rear blocks 717,719 such that, in effect, a continuous conduit is created from the inlet aperture 724 in the front block 717 to the outlet aperture 728 in the rear block 719. This continuous conduit forms a reaction zone.

The solid phase ribbon 715 is fed into the top of the front block 717 through the channel 723 in the block 717. The ribbon 715 passes downwardly through the channel 723 in the front block 717, is looped underneath the roller 726 in the central block 718, passes upwardly through the channel 727 in the rear block 719 and out of the top of the rear block 719.

The computer unit 714 is operatively connected to the stepper motor 713 via the motor controller 712. The speed of rotation of the motor 713 can be set by appropriate inputs to the computer unit 714. The motor 713 is arranged to drive the solid phase ribbon 715 through the reaction zone. A flexi drive 729a is used to couple the motor 713 to the solid phase ribbon 715.

The syringe and syringe driver 711 is controlled by the computer unit 714 and is connected to the inlet aperture 724 in the front block 717 via a fluid feed line 730. Fluid in the syringe 711 is forced under pressure through the fluid feed line 730 into the inlet aperture 724 through the inlet bore 725a, downwardly through the channel 723 in the front block 717, through the aperture 725b in the central block 718, upwardly through the channel 727 in the rear block 719, through the outlet bore 729b through the outlet aperture 728 in the rear block 719 and back into a return section of the fluid feed line 730. In the present embodiment the fluid is a liquid solution, although obviously a gas may be used.

A substance to be reacted is provided on the solid phase ribbon 715. Alternatively the substance may be linked to the solid phase ribbon 715 in the reaction zone. The solid phase ribbon 715 comprises a polymeric material suitable to host a solid phase reaction. For example the polymeric material is substantially insoluble in the solution present in the reaction zone and comprises groups that allow for attachment to at least one linker species of the substance. In the present embodiment the material is cellulose, or cotton. Any group that may act as a linker group may be appropriate.

As the solid phase ribbon 715 passes through the solution in the reaction zone, the substance reacts with the solution to form a product. A microwave energy source 90 exposes the solid phase ribbon 715 in the reaction zone, to microwave radiation. This improves the efficiency of the reaction.

In this case, the use of PTFE blocks instead of glass blocks, provides an advantage in that PTFE is more transparent to microwaves than glass.

The product remains attached to the solid phase ribbon 715 upon exit from the reactor 710 and may be cleaved at a later stage. Before the product is cleaved, the spectrometer 716 analyses the product.

The reactor 710 may be disassembled. Specifically, each of the three blocks of the reactor 710 may be disassembled. This provides a means of cleaning the apparatus 717,718,719 and also an easy means of passing the solid phase ribbon 715 through the channels 723,727 in the blocks 717,718,719.

Since there are separate entry and exit points for the solid phase ribbon 715 and the solution, this allows the solid phase ribbon 715 and solution to flow in the same direction or in reverse directions. Flowing in the reverse direction allows a concentration gradient to be established.

One way of increasing the time of the reaction and/or the amount of product produced by the reaction, under given conditions, is to increase the size of the reaction zone, for example by increasing the height of the channels 723,727 and the length of the solid phase ribbon 715. However, due to obvious physical constraints, the height of the channels 723, 727 is limited and therefore the time of the reaction and/or the amount of the product that may be produced under given conditions is limited.

The present embodiment of the invention seeks to overcome this issue. A number of reactors 710 may be connected together side by side to form a number of reaction zones. In such a configuration, the solid phase ribbon 715 may be passed from the outlet of one reactor into the inlet of an adjacent reactor.

A single source of fluid may supply all of the reaction zones, with fluid feed lines connecting each of the reactors together.

The above embodiments are by way of example only; many variations are possible without departing from the scope of the invention as defined by the appended claims.

EXAMPLES

The following Examples 1 to 8 serve to illustrate the chemistry of pretreating cotton ribbon ready for use in continuous solid phase peptide synthesis using Fmoc chemistry. The Examples illustrate the chemistry using batch methodology but the chemistry may be applied in a continuous process using an apparatus and method of the invention.

Example 1

Pretreatment of Cotton Tape Prior to Chemical Derivatisation

1 Record the Dry Mass of Cotton to nearest 0.01 g.
2 Run a domestic washing machine without detergent or textiles to clear any residues.
3 Unspool the cotton tape and place it into the washing machine with 10 ml of detergent.
4 Note the make and model of washing machine, along with the detergent.
5 Set the machine for a hot cycle (65 C).
6 Once the machine is finished remove the tape and dry at room temperature overnight.
7 Record the mass of the tape.
8 Place the tape in a glass beaker containing 1125 ml distilled water and heat until boiling.
9 Continue to boil the cotton for 5 minutes and then turn off heat.
10 Once cooled remove the cotton from the water and place in 200 ml of 99% ethanol. Allow it to stand overnight.
11 Remove the cotton from the alcohol and suck dry on a vacuum filter funnel.
12 Record the mass of cotton, and return it to the filter funnel and suck for another 2 minutes.

13 Record the mass of cotton, if it is within 10% of the mass of the value recorded in step 12 then finish, if not repeat until the mass is within the acceptable limit.
14 Take two 1.5 cm samples of the ribbon, one from each end. Record the masses of the samples to 0.001 g and store them in labelled airtight containers in a freezer.

Example 2

Acid Activation of Cotton

1 Divide the cotton into three approximately equal batches, and record the mass of each. Identify each (A, B, and C).
2 Add the masses of the three batches together and use this to calculate the volume of TFA/DCM needed using the formula: V=10 ml×M, where V is the volume of 25% v/v TFA/DCM needed, and M is the mass of cotton in grams.
3 Prepare the acid solution by adding the calculated volume of TFA (0.25V) dropwise to a stirred vessel containing the calculated volume of DCM (to the nearest 1 ml)
4 Place the three batches of cotton tape into three labelled glass conical flasks.
5 Pour the required volumes of TFA/DCM into each flask, and stopper the flasks with cotton wool.
6 Leave the flasks for approximately 60 minutes (+ or −5 minutes).
7 Remove each batch of cotton from the acid, and place into a beaker containing 6 ml per gram of cotton of DCM and leave for 5 minutes.
8 Wash each batch of cotton with DCM using the procedure of Example 4.
9 Wash each batch of cotton with 5% DIPEA/DCM using the procedure of Example 4.
10 Wash each batch of cotton with DCM using the procedure of Example 4.
11 Suck dry on vacuum funnel.
12 Place each batch of cotton into a labelled conical flask containing 1.3 ml per gram of cotton of DMF.
13 Leave for approximately 2 hours and proceed directly to Example 3.

Example 3

Attachment of Aminohexanoic Acid Spacer to Cotton

1 Calculate the volume of reagent needed at 1.3 ml of solution per gram of cotton.
2 Place the calculated volume of DMF into a conical flask. Then add the calculated masses of HOBt and Fmoc-aminohexanoic acid to the DMF so that their concentration is 0.6M. Add sufficient volume of N-methylimidazole to give a 1.2M concentration.
3 Stir until all the solids are dissolved, and then add dropwise over 15 minutes the required volume of DIC to give a 0.6M concentration.
4 Leave the solution to stir for a 15 further minutes.
5 Place each batch of cotton into a labelled conical flask and add the solution as prepared in steps 2, 3 and 4. Plug the top of the flask with cotton wool.
6 Place the conical flasks into a sonicator for one hour.
7 Leave the flasks at room temperature (record to nearest 1 C) for approximately 16 hours (+ or −1 hour).
8 Wash with DMF using the procedure of Example 4.
9 Wash with ethanol using the procedure of Example 4.
10 Wash with DCM using the procedure of Example 4.
11 Take two 1.5 cm samples from each of the batches (one from each end) and place them in labelled vials and store in a freezer.

Example 4

Washing

1 Place the cotton or ribbon into a flask.
2 Add the correct volume of solvent (6 ml per g of material).
3 Leave for 10 minutes.
4 Remove the cotton or ribbon from the solvent and suck dry on the vacuum funnel for 30 seconds.
5 Repeat steps 1, 2, 3 and 4 twice more.

Example 5

Loading Determination

Determination of Loading Using procedure described in Biotechnology and Bioengineering, Vol 61, No. 1, 2000, pgs 55-60.
1 Take 6×10 mg samples from each batch of ribbon and place them in individually labelled glass vials.
2 Accurately record the mass of each sample to 0.00001 g.
3 Into each vial place using a finnipipette 1000 µl of 20% v/v piperidine in DMF.
4 Cap the vials and leave to soak for 24 hours at room temperature.
5 From each of the vials take a 50 µl aliquot and transfer it to another labelled vial and make it up to 5000 µl with the addition of 4950 µl DMF.
6 Make up a blank using 50 µl of 20% piperidine/DMF and 4950 µl DMF.
7 Set the peak absorbance for the UV-vis spectrometer to 301 nm.
8 Record the absorbance for each sample against the blank.
9 The loading is determined using the following formula:

$$FS = (1000A)/(M(7800D))$$

Where:
FS is loading in mmolg$^{-1}$
A is absorbance
M is mass of sample in mg
D is dilution factor of 0.01 and
7800 is the extinction coefficient in lmol$^{-1}$ cm$^{-1}$

Example 6

Capping

1 Record the mass of each batch of ribbon.
2 Mix up a 1:2:3 v/v/v acetic anhydride/N-methylimidazole/DMF solution by adding dropwise the acetic anhydride to the DMF and N-methylimidazole.
3 Place each batch into a conical flask and add 1.3 ml per g of ribbon of the solution from step 2 to each.
4 Leave the flasks for 1 hour.
5 Remove each batch of ribbon and suck on the vacuum funnel for 30 seconds.
6 Wash with DMF using the procedure of Example 4.
7 Wash with ethanol using the procedure of Example 4.
8 Wash with DCM using the procedure of Example 4.

9 Take two 1.5 cm samples from each batch and place in labelled vials and store in freezer.

Example 7

Deprotection

Procedure
1 Prepare a solution of 20% v/v diethylamine in DMF.
2 Place each batch of ribbon into a labelled conical flask.
3 Add 2 ml per g of ribbon of the 20% diethylamine/DMF solution to each flask.
4 Leave the flasks at room temperature (record) for 15 minutes.
5 Remove each batch of ribbon and suck dry on the vacuum funnel.
6 Wash with DMF using the procedure of Example 4.
7 Wash with ethanol using the procedure of Example 4.
8 Wash with DCM using the procedure of Example 4.
9 Dry to constant mass.
10 Record the mass of each batch.

Example 8

Attachment of Rink Linker to Ribbon

1 Record the mass of each batch of ribbon.
2 Deprotect each batch of ribbon using the procedure of Example 7.
3 Place each batch of ribbon into a flask containing 1.3 ml per g of ribbon of DMF and leave to swell for two hours.
4 Calculate the amount of reactants needed to give 3 equivalents of HATU and Rink acid per active group on the ribbon assuming a loading of 140 $\mu molg^{-1}$.
5 Calculate the mass of DIPEA needed to give 6 equivalents.
6 Dissolve the HATU and Rink acid in 1.3 ml of DMF per gram of ribbon. Add the DIPEA and stir for 1 minute.
7 Remove each piece of ribbon and suck on the vacuum funnel for 30 seconds.
8 Place each of the batches of ribbon into a flask containing the solution prepared in step 5.
9 Place the flasks into the sonicator and sonicate for 1 hour.
10 Leave the flasks to stand at room temperature for 30 minutes.
11 Remove each of the batches of ribbon from the reactants and suck dry on the vacuum funnel.
12 Wash with DMF using the procedure of Example 4.
13 Wash with ethanol using the procedure of Example 4.
14 Wash with DCM using the procedure of Example 4.
15 Take two 1.5 cm samples from each of the batches (one from each end) and place them in labelled vials and store in a freezer.

What is claimed:

1. A process for performing a solid phase synthesis, wherein the process comprises the stages of the solid phase synthesis, in each of which stages a mobile elongate solid phase is treated with a flowing fluid phase and the solid phase and the fluid phase are moved through a lumen of a conduit in which the two phases come into mutual contact, and the process comprising a stage of a solid phase synthesis, wherein said solid phase synthesis comprises at least two synthesis stages in which the solid phase is contacted with a synthetic building block, the synthetic building block being added to the solid phase by covalent bond formation and at least one of said stages comprises cleavage of a covalent bond.

2. The process of claim 1 wherein each said stage comprises:
moving the solid phase through an apparatus, wherein the apparatus comprises:
a conduit which is of circular or non-circular transverse cross section and which defines a lumen to contain both the flowing fluid phase and the mobile elongate solid phase;
fluid phase ports in communication with the lumen to allow the fluid phase to enter the lumen, flow through it and exit it; and
solid phase ports in communication with the lumen to allow the mobile solid phase to enter the lumen, move through it and exit it, the apparatus being adapted to prevent fluid egress from its interior through the solid phase ports
the process comprising:
moving the solid phase through a first solid phase port of the apparatus into the lumen of the apparatus, though the lumen and out through a second solid phase port of the apparatus;
causing the fluid phase to enter the lumen of the apparatus through a first fluid phase port, flow through the lumen and leave through a second fluid phase port.

3. The process of claim 2 wherein the elongate solid phase is in the form of a ribbon.

4. The process of claim 2 wherein the elongate solid phase comprises a substrate and optionally a substance bonded thereto.

5. The process of claim 2, wherein the conduit is defined by a plurality of releasably interconnected plates, the plates comprising a pair of plates in opposed face-to-face relationship and the opposed faces having defined between them a length of the conduit extending in a direction parallel with the pair of plates.

6. The process of claim 2, wherein the conduit comprises an upper region adjacent to the solid phase port having an increased cross-sectional area relative to the remainder of the conduit.

7. The process of claim 2 wherein the apparatus is a first said apparatus and is in combination with a second said apparatus to provide a pathway along which the elongate solid phase is moved out of the second solid phase port of the first apparatus and into a first solid phase port of the second apparatus, and then through the lumen of the second apparatus and out of a second solid phase port of the second apparatus while a fluid is caused to flow through the second apparatus.

8. The process of claim 7 wherein the fluid which flows through the first apparatus is supplied from a different fluid source to the fluid which flows through the second apparatus, and wherein the fluid which flows through the first apparatus comprises a reagent which reacts with the substrate or with a substance bonded thereto or comprises a labelled agent, and the fluid which flows through the second apparatus washes the elongate solid phase.

9. The process of claim 7 which comprises a solid phase synthesis of a polymer, wherein the elongate solid phase is moved through a plurality of said apparatuses in succession in carrying out the synthesis, the solid phase and the fluid phase in each of the apparatuses being contacted together to perform a respective step of the synthesis, each of said respective steps being performed either in a single said apparatus or in a plurality of said apparatuses arranged one after the other.

10. The process of claim 9 which further comprises spatially addressing a plurality of synthetic building blocks onto the elongate solid phase to cause them to react with the substrate or a substance bonded thereto, to form an array of different substances.

11. The process of claim 10 wherein the solid phase synthesis results in a post-synthetic solid phase which comprises an array of spatially distinct areas, each area containing end product molecules of a respective predetermined structure bonded to the substrate, the process further comprising:
exposing the post-synthetic solid phase to an agent which, when it contacts an analyte having a predetermined property, undergoes a process specific to such analyte to create a detectable response; and
determining the presence and/or amount of the detectable response of each spatially distinct area.

12. The process of claim 1 that comprises a stage wherein the fluid phase flows through the lumen in an opposite direction to the movement of the solid phase.

13. The process of claim 12 wherein the process comprises moving the solid phase through a solid phase synthesis system that includes treatment zones to perform, on the solid phase as it is moved through the system, all the stages of a solid phase synthesis of a polymer.

14. The process of claim 13 wherein the polymer is a poly(amino acid).

15. The process of claim 13 wherein the polymer is a polynucleotide.

16. The process of claim 13 wherein the polymer is a polysaccharide.

17. The process of claim 1 wherein the fluid phase of each stage is a liquid phase, and wherein the process comprises
a said stage in which the liquid phase comprises a reagent that reacts with the substrate or with a substance bonded thereto to remove a protecting group,
a said stage in which the liquid phase comprises a reagent that reacts with the substrate or with a substance bonded thereto to activate a functional group, and
said at least two synthesis stages in which a synthetic building block is added to the solid phase by covalent bond formation, the liquid phase comprising a reagent that reacts with the substrate or with a substance bonded thereto to add the synthetic building block to the substrate or the substance by the covalent bond formation.

18. The process of claim 17 wherein the process comprises a stage wherein the fluid phase is a liquid phase, and wherein the liquid phase washes the elongate solid phase.

19. The process of claim 1 wherein the process comprises moving the solid phase through a solid phase synthesis system that includes treatment zones to perform, on the solid phase as it is moved through the system, all the stages of a solid phase synthesis of a polymer.

20. The process of claim 19 wherein the polymer is a poly(amino acid).

21. The process of claim 19 wherein the polymer is a polynucleotide.

22. The process of claim 19 wherein the polymer is a polysaccharide.

23. The process of claim 19, wherein the at least one stage of a solid phase synthesis that involves cleavage of a covalent bond is the cleavage of the polymer from the solid phase.

24. The process of claim 1 wherein the solid phase synthesis forms an end product that is a polymer.

25. The process of claim 1 wherein the solid phase comprises a material selected from celluloses, glass fiber webs and glass fiber ribbons.

26. The process of claim 1, wherein the fluid phase flow is controllable by a controllable fluid metering device and the movement of the solid phase is controllable by a controllable drive device.

27. The process of claim 1, wherein the conduit is generally rectangular in cross section, the length of the lumen in which the solid and fluid phases are in contact is from about 25 cm to about 500 cm and it has a height (shortest cross sectional dimension) of between about 1 mm and about 3 mm.

28. The process of claim 1, wherein the at least one stage of a solid phase synthesis that involves cleavage of a covalent bond is the removal of a protecting group.

29. A process for solid phase synthesis, comprising moving an elongate solid phase through an apparatus for contacting the elongate solid phase with a flowing liquid phase, the elongate solid phase comprising a substrate and optionally a substance bonded thereto and the apparatus comprising:
a conduit which is of circular or non-circular transverse cross section and which defines a lumen to contain both the flowing fluid phase and the mobile elongate solid phase;
liquid phase ports in communication with the lumen to allow the fluid phase to enter the lumen, flow through it and exit it;
solid phase ports in communication with the lumen to allow the mobile solid phase to enter the lumen, move through it and exit it;
a controllable drive device for moving the solid phase through the conduit, the drive device comprising a drive motor coupled to a drive roller; and
a fluid metering device for providing a fluid phase flow to the conduit,
wherein the solid phase ports are spaced above the fluid phase ports, whereby in use the liquid phase does not contact the solid phase ports, and wherein a guide roller is arranged to guide the solid phase before it enters or, as the case may be, after it exits a said solid phase port, the apparatus being a first said apparatus and being in combination with a second said apparatus to provide a pathway along which the elongate solid phase moves out of a solid phase port of the first apparatus and into a solid phase port of the second apparatus via the roller, and wherein the solid phase pathway includes a plurality of guide rollers for guiding the solid phase along the pathway, wherein a said guide roller is the drive roller,
the process comprising moving the solid phase through:
at least two synthesis zones in which the solid phase is contacted with a synthetic building block that, when so contacted, reacts with a reactive group to become bound to the substrate or with a moiety already formed by one or more previous synthetic building blocks, the synthetic building blocks being contacted with the solid phase by contacting the solid phase with a flowing liquid phase using a said apparatus, the liquid phase flowing through the lumen of each apparatus in an opposite direction to the movement of the solid phase;
a washing zone in which the solid phase is washed after being contacted with a reagent, in order to remove unreacted reagent, the solid phase being contacted with a flowing liquid phase using a said apparatus;
a deprotection zone in which the solid phase is contacted with a flowing liquid phase using an apparatus of the invention to deprotect a protected functional group of a moiety bound to the substrate prior to a synthesis step; and
a cleaving zone for cleaving attached molecules from the solid phase using an apparatus of the invention.

* * * * *